(12) United States Patent
Bethel et al.

(10) Patent No.: US 12,024,520 B2
(45) Date of Patent: Jul. 2, 2024

(54) PROCESSES FOR THE PREPARATION OF 4-{8-AMINO-3-[(2S)-1-(BUT-2-YNOYL)-PYRROLIDIN-2-YL]IMIDAZO[1,5-A]-PYRAZIN-1-YL}N-(PYRIDIN-2-YL)-BENZAMIDE

(71) Applicant: Acerta Pharma B.V., Oss (NL)

(72) Inventors: Paul Allen Bethel, Cambridge (GB); Lai Chun Chan, Cambridge (GB); Katie Grace Cooper, Cambridge (GB); Robert John Cox, Cambridge (GB); Michael David Golden, Cambridge (GB); Shaun Alan Hughes, Cambridge (GB); Lucinda Victoria Jackson, Cambridge (GB); Kirsty Jane Millard, Cambridge (GB); Andrew John Phillips, Cambridge (GB); Alexander James Telford, Cambridge (GB); Jerry Evarts, Seattle, WA (US); Michael Joseph Lawler, Waunakee, WI (US); Remy E. J. N. Litjens, NM Weert (NL); Peter Johannes Servaas Savio Van Eijk, NM Weert (NL); Mathilda Maria Henrica Verstappen, NM Weert (NL); Frank L. M. Vos, NM Weert (NL); Eric Jurriën Zijp, NM Weert (NL); Qiu Junying, Tianjin (CN); Rustam Ferdinand Garrey, Salem, OR (US); David Allen Short, Springfield, OR (US); Angang Wang, Dalian (CN)

(73) Assignee: ACERTA PHARMA B.V., Oss (NL)

( * ) Notice: Subject to any disclaimer, the term of this patent is extended or adjusted under 35 U.S.C. 154(b) by 650 days.

(21) Appl. No.: 17/271,750

(22) PCT Filed: Aug. 28, 2019

(86) PCT No.: PCT/EP2019/072991
§ 371 (c)(1),
(2) Date: Feb. 26, 2021

(87) PCT Pub. No.: WO2020/043787
PCT Pub. Date: Mar. 5, 2020

(65) Prior Publication Data
US 2022/0127270 A1   Apr. 28, 2022

Related U.S. Application Data

(60) Provisional application No. 62/724,228, filed on Aug. 29, 2018.

(51) Int. Cl.
*C07D 487/04* (2006.01)
*C07B 63/00* (2006.01)

(52) U.S. Cl.
CPC ............ *C07D 487/04* (2013.01); *C07B 63/00* (2013.01); *C07B 2200/13* (2013.01)

(58) Field of Classification Search
CPC ............................ C07D 487/04; C07B 63/00
See application file for complete search history.

(56) References Cited

U.S. PATENT DOCUMENTS

| 7,459,554 B2 | 12/2008 | Dong et al. |
| 9,290,504 B2 | 3/2016 | Barf et al. |
| 11,161,851 B2 | 11/2021 | Wang et al. |
| 2014/0155385 A1 | 6/2014 | Barf et al. |
| 2019/0367524 A1 | 12/2019 | Cai et al. |
| 2019/0375755 A1 | 12/2019 | Sheng et al. |

FOREIGN PATENT DOCUMENTS

| CN | 107056786 A | 8/2017 |
| CN | 107522701 A | 12/2017 |
| CN | 108250186 A | 7/2018 |
| JP | 2014-520870 A | 8/2014 |
| WO | 2008/121742 A2 | 10/2008 |
| WO | 2010/126960 A1 | 11/2010 |
| WO | 2011/095556 A1 | 8/2011 |
| WO | 2013-010868 A1 | 1/2013 |
| WO | 2016/128912 A1 | 8/2016 |
| WO | 2017/002095 A1 | 1/2017 |
| WO | 2017/077507 A1 | 5/2017 |
| WO | 2018-115965 A1 | 6/2018 |
| WO | 2018/116259 A1 | 6/2018 |
| WO | 2018/130213 A1 | 7/2018 |
| WO | 2018/191815 A1 | 10/2018 |
| WO | 2019/090269 A1 | 5/2019 |

OTHER PUBLICATIONS

Anonymous, Use of 1-bromo-3-[(2S)-pyrrolidin-2-yl]imidazo[1,5-a]pyrazin-8-amine as an intermediate for making acalabrutinib, Research Disclosure database No. 631028, 2016.
Ashton et al., Thermal Stability of 2-Butynoic Acid (Tetrolic Acid), OPR&D, 2019, 23, pp. 1101-1104.
Barf, et al., Acalabrutinib (ACP-196): A Covalent Bruton Tyrosine Kinase Inhibitor with a Differentiated Selectivity and In Vivo Potency Profile, J. Pharmacol. Exp. Ther. 363:240-252, Nov. 2017 (including Supplemental Information pp. 1-20).
Bethel et al., Development of Commercial Manufacturing Processes for Acalabrutinib, OPR&D, 2022, 26, pp. 3303-3311.
Chen et al., A Manufacturing Process to an Intermediate in the Synthesis of Acalabrutinib, OPR&D, 2018, 22, pp. 1458-1460.
Flick, et al., Synthetic Approaches to the New Drugs Approved During 2017, J. Med. Chem. 2019, 62, 7340-7382.

(Continued)

*Primary Examiner* — Kamal A Saeed

(57) ABSTRACT

The present disclosure relates, in general, to improved processes for the preparation of 4-{8-amino-3-[(2S)-1-(but-2-ynoyl)pyrrolidin-2-yl]imidazo[1,5-a]pyrazin-1-yl}-N-(pyridin-2-yl)-benzamide, particularly large-scale processes for manufacturing 4-{8-amino-3-[(2S)-1-(but-2-ynoyl)pyrrolidin-2-yl]imidazo[1,5-a]pyrazin-1-yl}-N-(pyridin-2-yl) benzamide and intermediates used in such processes.

29 Claims, 4 Drawing Sheets

(56) References Cited

OTHER PUBLICATIONS

Inglesby, et al., Diethanolamine Boronic Esters: Development of a Simple and Standard Process for Boronic Ester Synthesis, Organic Process Research & Development 2020 24 (9), 1683-1689.
Liu, et al., Ibrutinib (Imbruvica): The First-in-Class Btk Inhibitor for Mantle Cell Lymphoma, Chronic Lymphocytic Leukemia, and Waldenstrom's Macroglobulinemia, Innovative Drug Synthesis, Chap. 8, pp. 157-164 (1st Ed. 2016).
Natural Product Chemistry for Pharmaceutical Students, Nankodo Co., Ltd., 2004, pp. 139-141 (Japanese textbook).
Caira, Clystalline Polymorphism of Organic Compounds, Top. Curr. Chem, 1988, pp. 164-208, vol. 198.
Zheng, et al., From atylureas to bialylamides to aminoquinazolines: Discovely of a novel, potent TRPV1 antagonist, Bioorg. Med. Chem. Lett. 2006, pp. 5217-5221, vol. 16
PCT/IB2019/072991 International Search Report and Written Opinion dated Jan. 23, 2020.

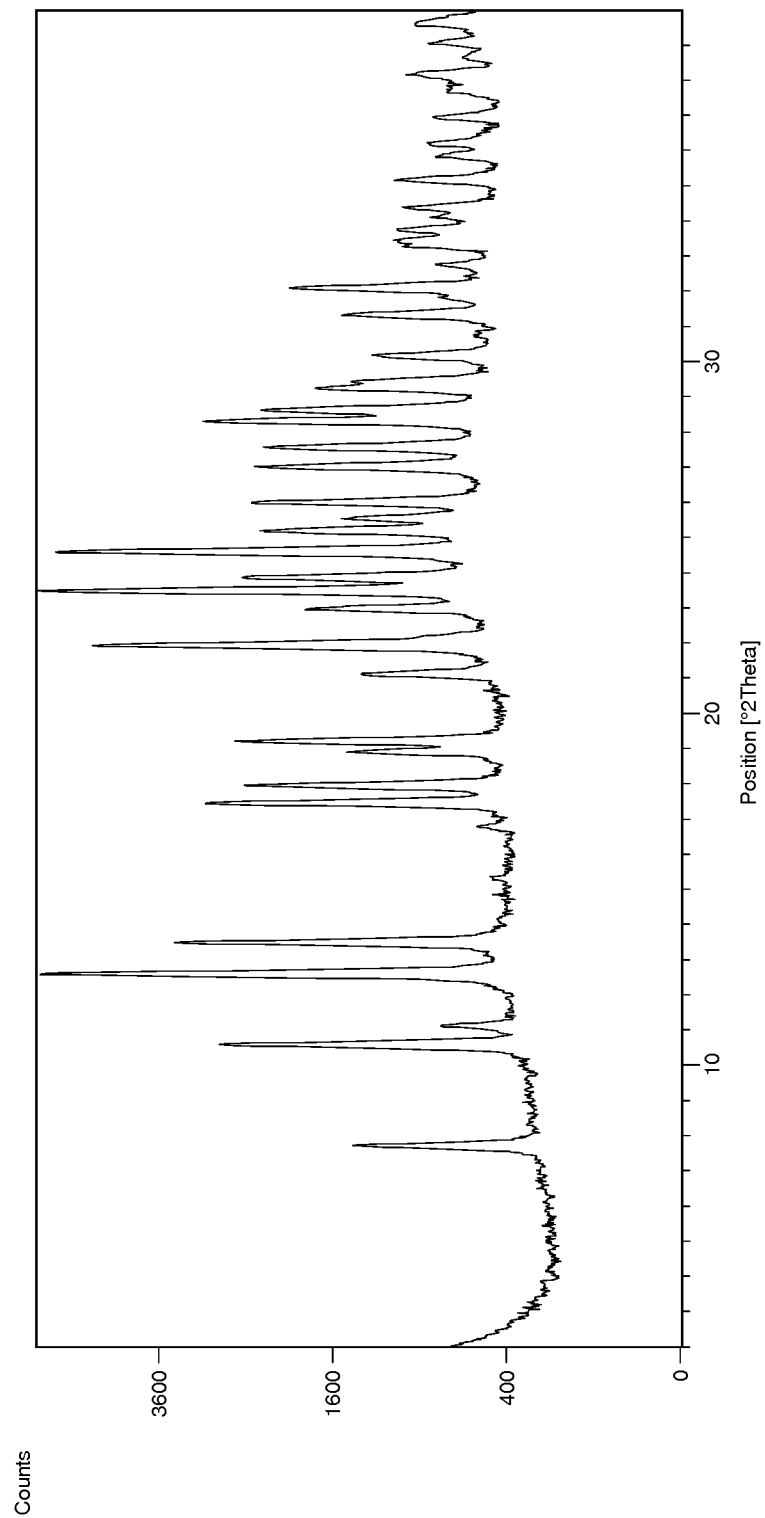
Fig. 1: Sulfate Salt (2/3) of Compound (IV)

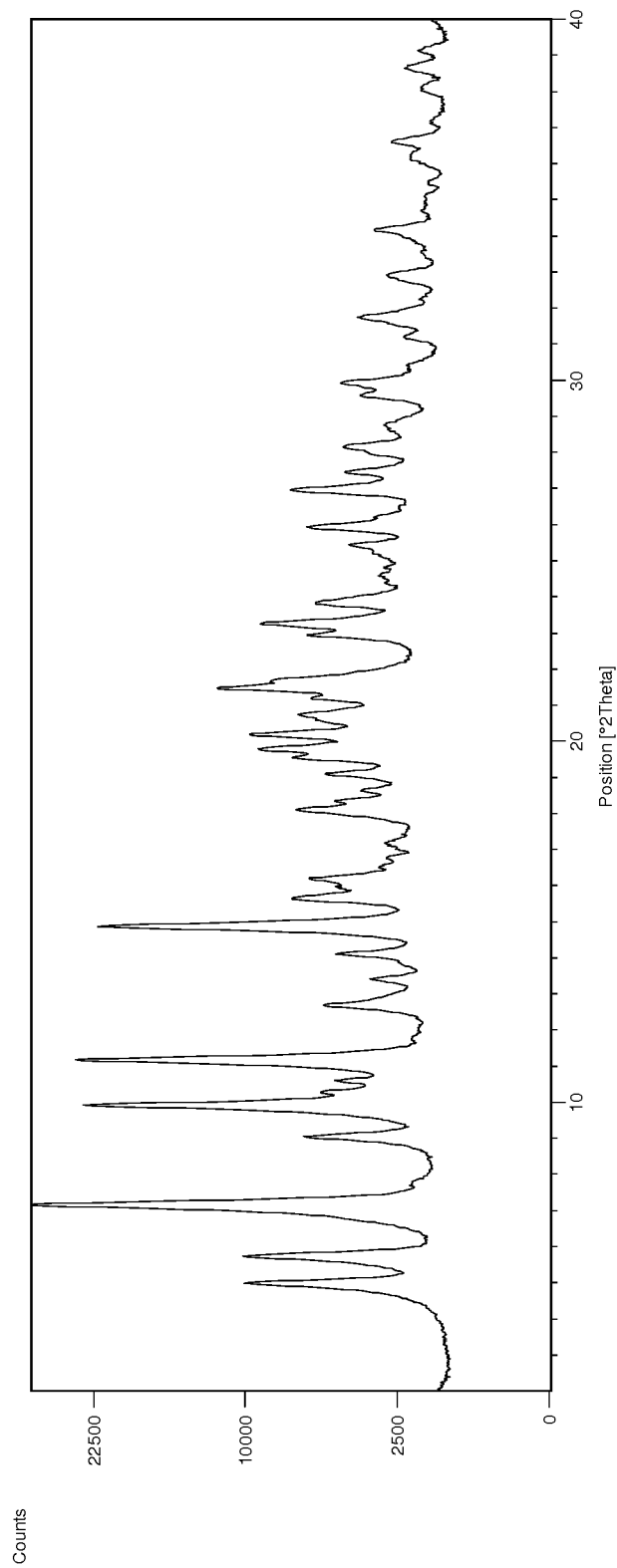
Fig. 2: Type 2 Crystalline Form of Compound (VII)

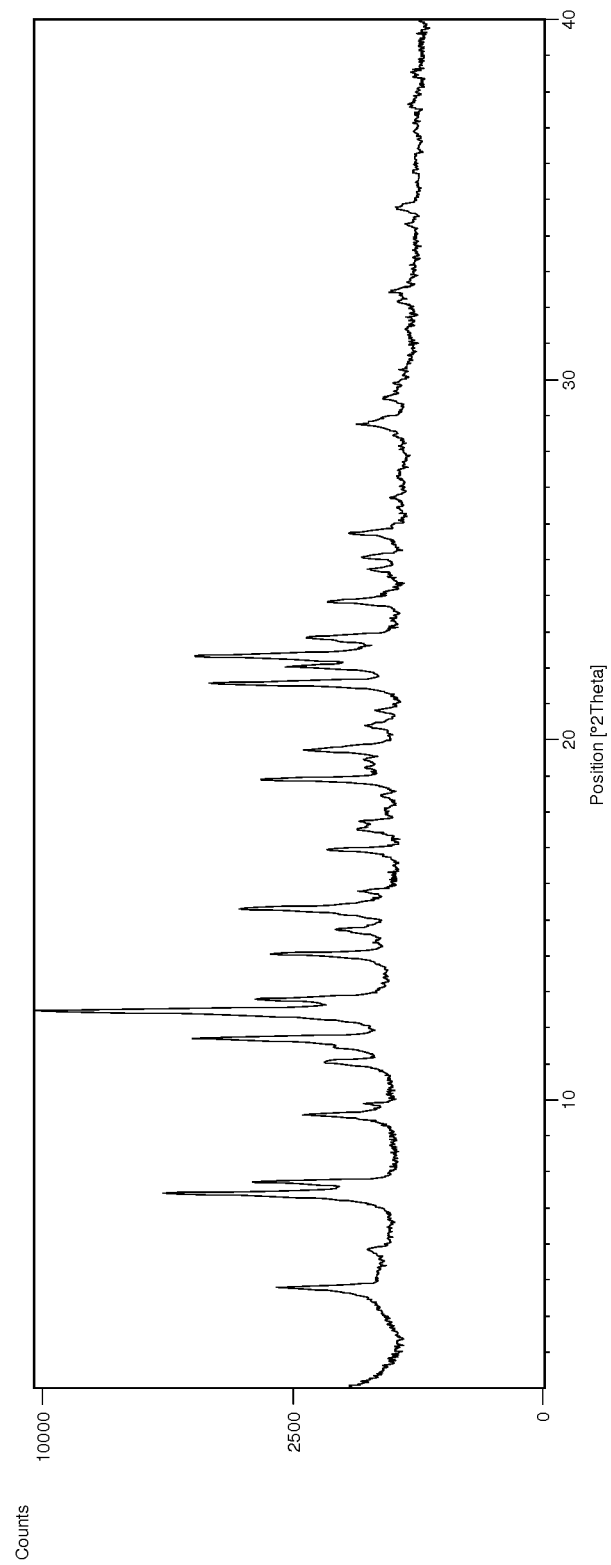
Fig. 3: Type 3 Crystalline Form of Compound (VII)

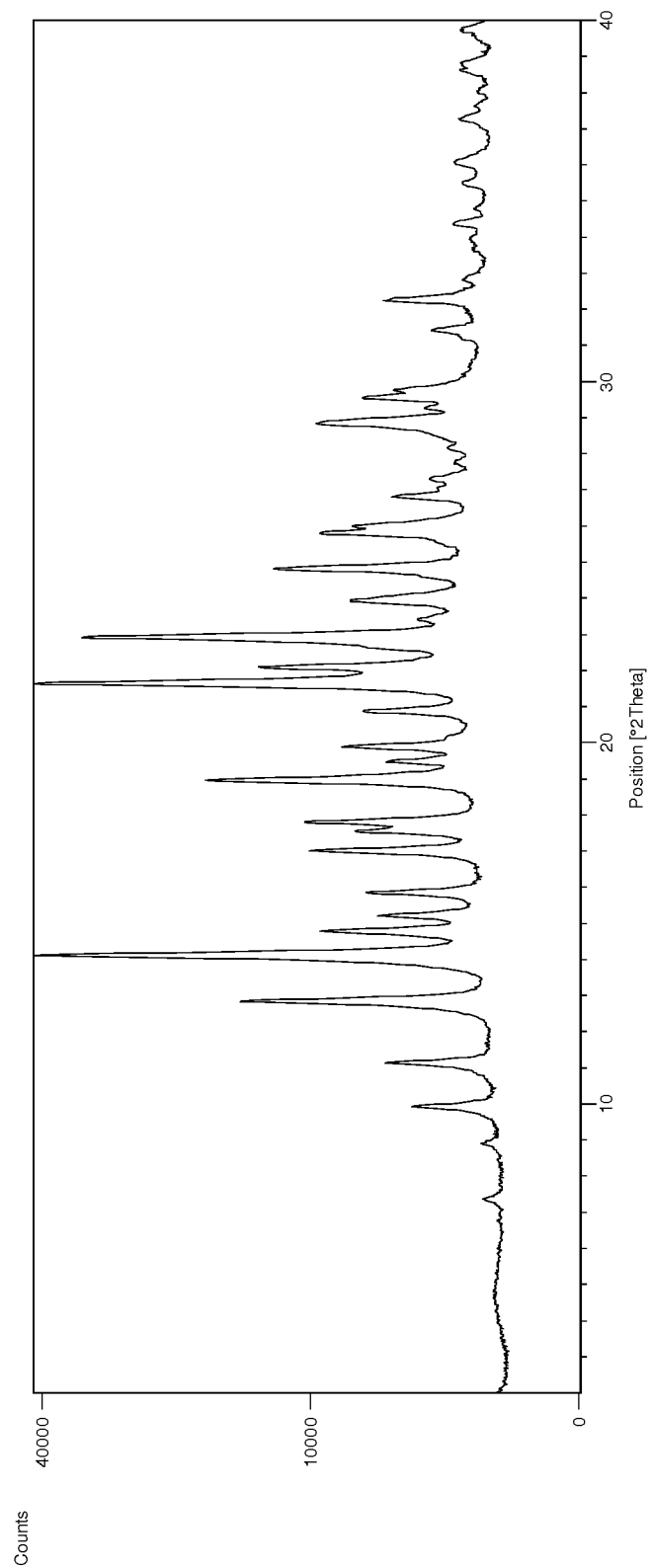
Fig. 4: Form C Crystalline Form of Compound (VII)

PROCESSES FOR THE PREPARATION OF 4-{8-AMINO-3-[(2S)-1-(BUT-2-YNOYL)-PYRROLIDIN-2-YL]IMIDAZO[1,5-A]-PYRAZIN-1-YL}N-(PYRIDIN-2-YL)-BENZAMIDE

CROSS-REFERENCE TO RELATED APPLICATION

This application is a U.S. National Phase Application of International Application No. PCT/EP2019/072991, filed on Aug. 28, 2019, which claims the benefit under 35 U.S.C. § 119(e) of U.S. Provisional Application No. 62/724,228, filed on Aug. 29, 2018. Each of the above-listed applications is incorporated by reference herein in its entirety.

FIELD OF THE INVENTION

The present disclosure relates, in general, to improved processes for the preparation of 4-{8-amino-3-[(2S)-1-(but-2-ynoyl)pyrrolidin-2-yl]imidazo[1,5-a]pyrazin-1-yl}-N-(pyridin-2-yl)-benzamide, particularly large-scale processes for manufacturing 4-{8-amino-3-[(2S)-1-(but-2-ynoyl)pyrrolidin-2-yl]imidazo[1,5-a]pyrazin-1-yl}-N-(pyridin-2-yl)benzamide and/or intermediates employed in such processes.

BACKGROUND OF THE INVENTION

4-{8-amino-3-[(2S)-1-(but-2-ynoyl)pyrrolidin-2-yl]imidazo[1,5-a]pyrazin-1-yl}-N-(pyridin-2-yl)benzamide (also known by the International Nonproprietary Name of acalabrutinib) is the active pharmaceutical ingredient in the drug product CALQUENCE®. In 2017, the United States Food and Drug Administration granted marketing approval to CALQUENCE® for the treatment of mantle cell lymphoma in adult patients who have received at least one prior therapy. Clinical trials evaluating the use of CALQUENCE® to treat additional indications, including chronic lymphocytic leukemia and Waldenström's macroglobulinemia, are ongoing.

Example 6 of U.S. Pat. No. 9,290,504 discloses acalabrutinib and reports the synthesis shown in Scheme 1 below:

SCHEME 1

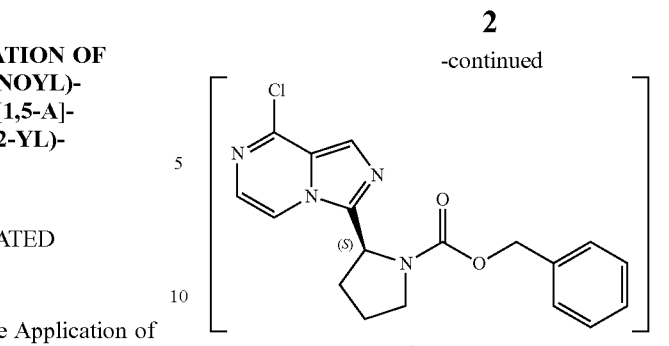

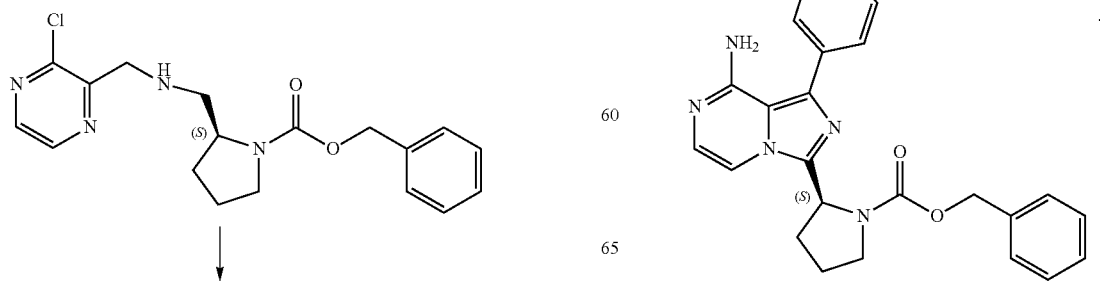

3
-continued
4
-continued
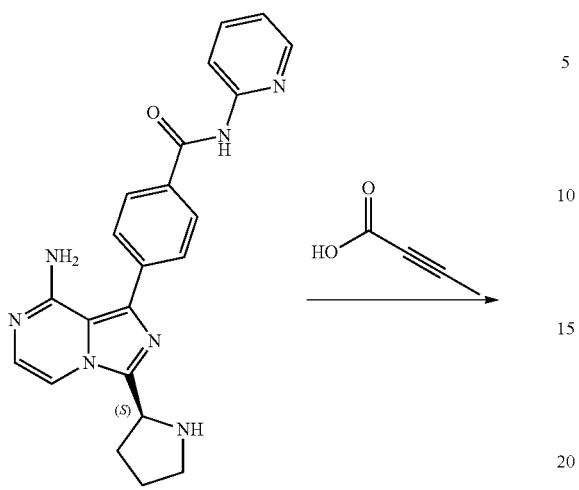
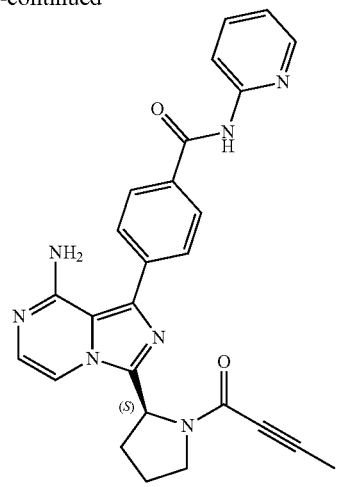
Research Disclosure Database No. 631028 (published digitally on Oct. 6, 2016) reports the synthesis of acalabrutinib shown in Scheme 2 below:
SCHEME 2
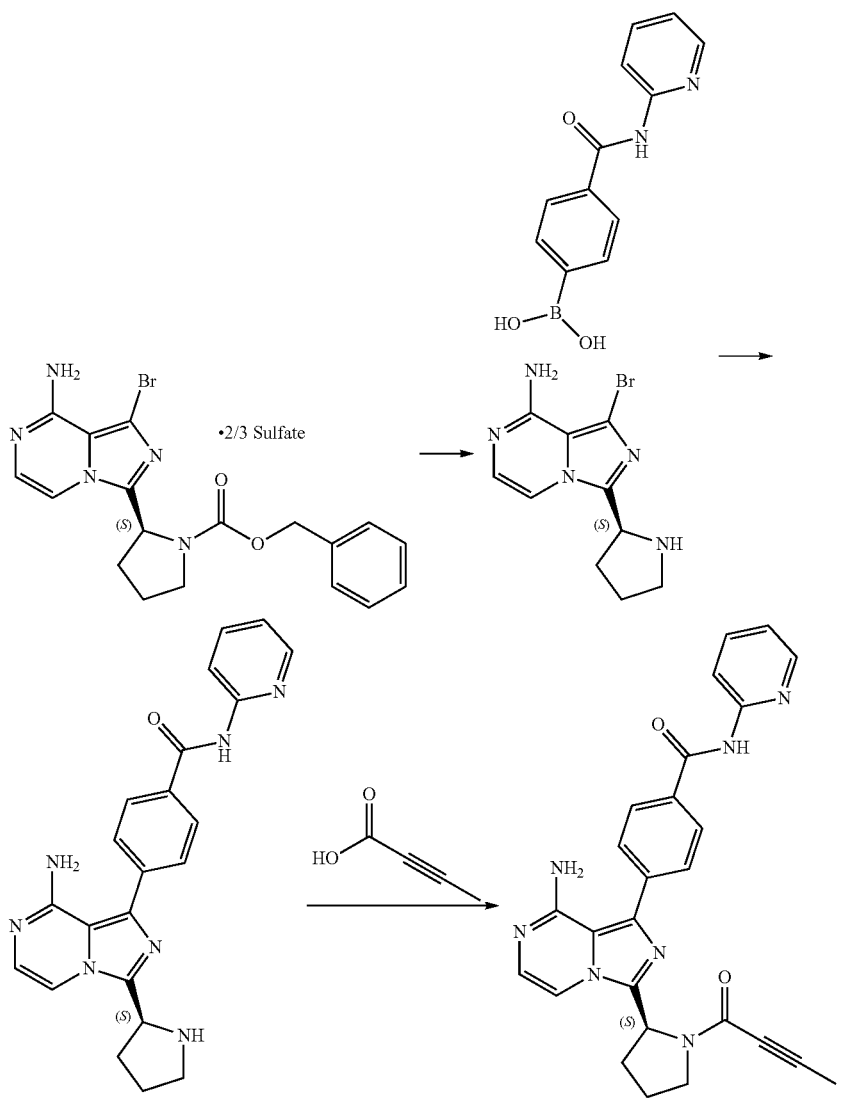

The previously reported synthetic methods, however, are not suitable for the large-scale, particularly commercial scale, manufacture of acalabrutinib. The present disclosure provides improved processes that can be operated at large scale and provide one or more advantages relative to the previously reported synthetic methods, such as improved compound purity, improved compound isolation (e.g., filterability), reduced cycle time, less stringent process control requirements, higher yield, reduced cost, improved compliance with regulatory requirements for pharmaceutical starting materials, intermediates, and products, and the like.

BRIEF DESCRIPTION OF THE INVENTION

As noted above, the present disclosure relates to improved large-scale processes for preparing acalabrutinib and/or intermediates employed in preparing acalabrutinib.

In one aspect, the present disclosure relates to a process for preparing a compound having the structure of Formula (VIII):

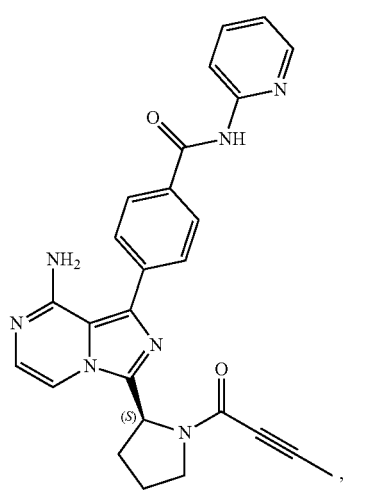

(VIII)

or a salt thereof, wherein the process comprises:
contacting a compound having the structure of Formula (VII):

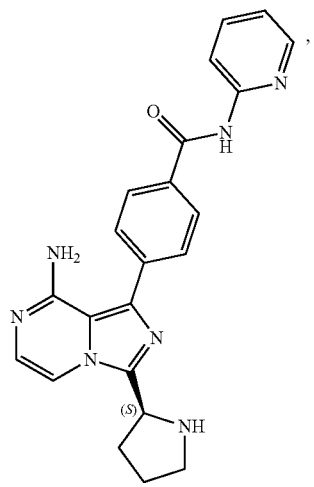

(VII)

or a salt thereof, with 2-butynoic acid, or a salt thereof, in the presence of 1-propylphosphonic anhydride and a base in a reaction medium to form a reaction mixture comprising the compound of Formula (VIII), or salt thereof, and one or more reaction by-products; and
selectively isolating the compound of Formula (VIII), or salt thereof, from the reaction mixture relative to the one or more reaction by-products.

In another aspect, the present disclosure relates to a process for preparing a compound having the structure of Formula (VII):

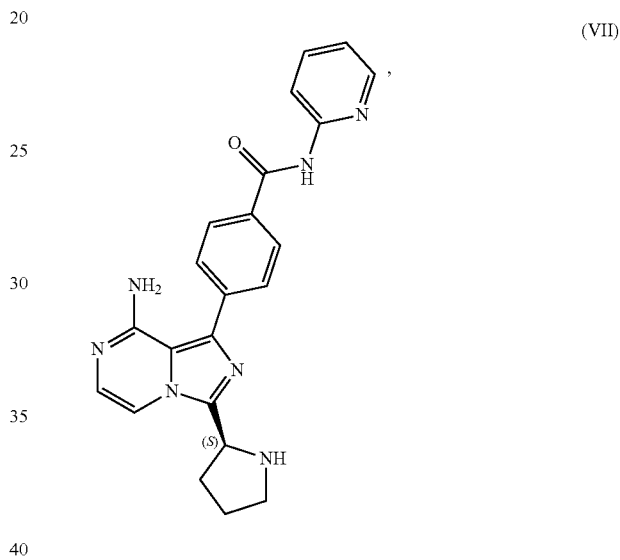

(VII)

or a salt thereof, wherein the process comprises:
contacting a compound having the structure of Formula (V):

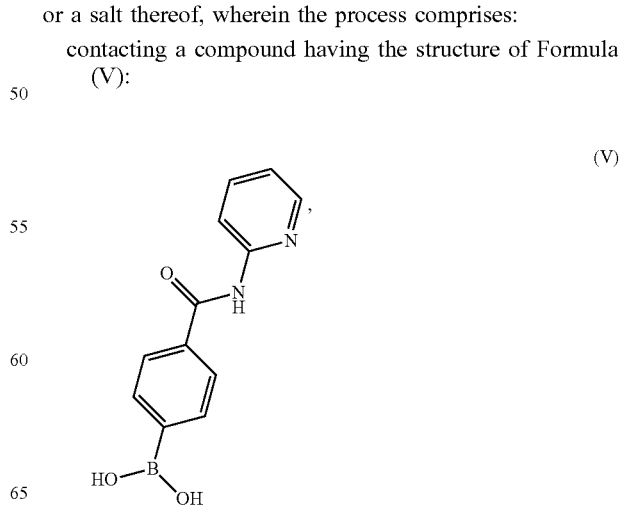

(V)

or a salt thereof, with a compound having the structure of Formula (VI):

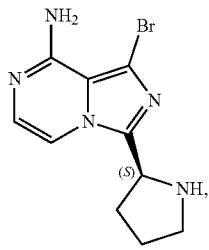

(VI)

or a salt thereof, in the presence of a base and a palladium catalyst in an aqueous reaction medium comprising an organic solvent to form a reaction mixture comprising the compound of Formula (VII), or salt thereof;
decreasing the amount of water present in the reaction mixture to form a substantially anhydrous mixture comprising the compound of Formula (VII), or salt thereof; and
isolating the compound of Formula (VII), or salt thereof, from the substantially anhydrous mixture.

In another aspect, the present disclosure relates to a process for preparing a compound having the structure of Formula (VI):

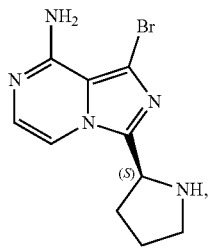

(VI)

or a salt thereof, wherein the process comprises:
contacting a compound of Formula (IV):

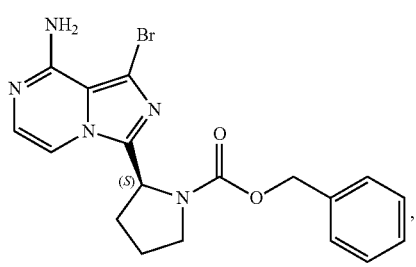

(IV)

or a salt thereof, with an acidic medium under conditions sufficient to deprotect the compound of Formula (IV) and form a reaction mixture comprising the compound of Formula (VI), or a salt thereof, and a benzyl halide by-product; and
isolating the compound of Formula (VI), or salt thereof, from the reaction mixture under conditions sufficient to substantially avoid the formation of an aminal impurity.

In another aspect, the present disclosure relates to a process for preparing a compound having the structure of Formula (V):

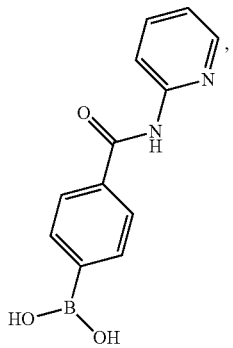

(V)

or a salt thereof, wherein the process comprises contacting 4-carboxyphenylboronic acid, or a salt thereof, with thionyl chloride and a catalyst in a reaction medium comprising an organic solvent to form an acyl chloride intermediate which is then contacted in situ with 2-aminopyridine to form a reaction mixture comprising the compound of Formula (V), or salt thereof.

In another aspect, the present disclosure relates to a process for preparing a sulfate salt of a compound having the structure of Formula (IV):

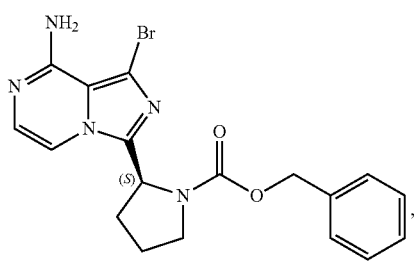

(IV)

wherein the process comprises:
contacting a compound having the structure of Formula (III):

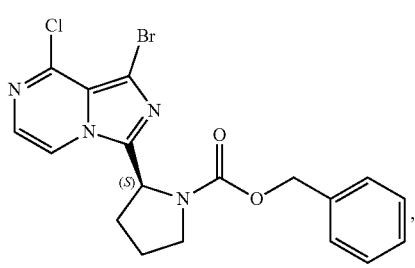

(III)

or a salt thereof, with an aminating agent in a reaction medium to form a reaction mixture comprising the compound of Formula (IV);
forming a sulfate salt of the compound of Formula (IV); and
isolating the sulfate salt.

In another aspect, the present disclosure relates to a process for preparing a compound having the structure of Formula (III):

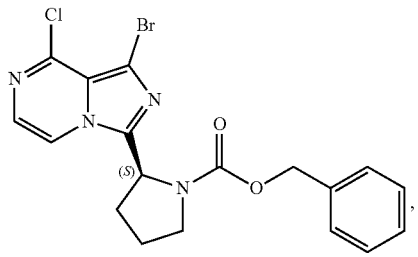

(III)

or a salt thereof, wherein the process comprises:

contacting a compound having the structure of Formula (I):

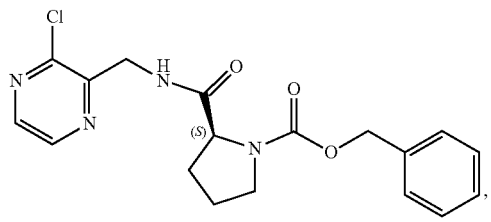

(I)

or a salt thereof, with a cyclizing agent in the presence of a catalyst in a reaction medium to form a compound of Formula (II):

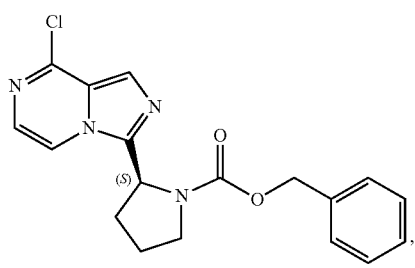

(II)

or salt thereof; and brominating the compound of Formula (II), or salt thereof, with a brominating agent to provide a compound having the structure of Formula (III):

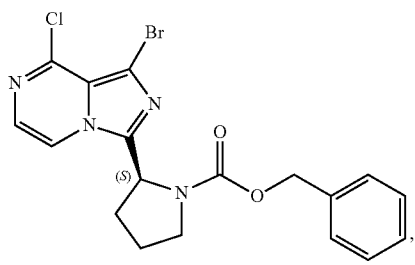

(III)

or a salt thereof;

wherein the temperature of the reaction medium is controlled during the contacting step in a manner sufficient to maintain a chiral purity of at least about 80% for the compound of Formula (II), or salt thereof.

In another aspect, the present disclosure relates to a process for preparing a compound having the structure of Formula (II):

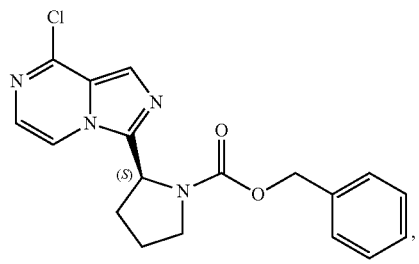

(II)

or a salt thereof, wherein the process comprises:

contacting a compound having the structure of Formula (I):

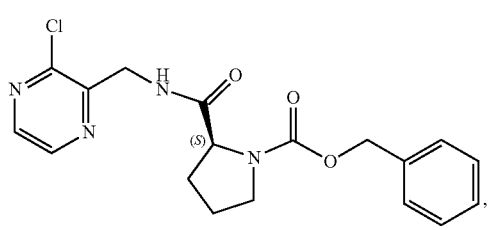

(I)

or a salt thereof, with a cyclizing agent in the presence of a catalyst in a reaction medium to form the compound of Formula (II), or salt thereof;

wherein the temperature of the reaction medium is controlled during the contacting step in a manner sufficient to maintain a chiral purity of at least about 80% for the compound of Formula (II), or salt thereof.

In another aspect, the present disclosure relates to a crystalline form of a compound having the structure of Formula (VII):

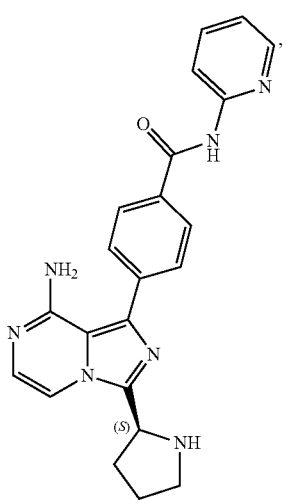

(VII)

wherein the crystalline form is characterized by a reflection X-ray powder diffraction pattern selected from:
a reflection X-ray powder diffraction pattern comprising at least three peaks selected from the group consisting of 9.9±0.2 °2θ, 11.1±0.2 °2θ, 12.8±0.2 °2θ, 14.1±0.2 °2θ, and 19.0±0.2 °2θ, and
a reflection X-ray powder diffraction pattern comprising at least three peaks selected from the group consisting of 7.4±0.2 °2θ, 11.7±0.2 °2θ, 12.5±0.2 °2θ, 22.3±0.2 °2θ, and 21.6±0.2 °2θ.

In another aspect, the present disclosure relates to a crystalline form of a compound having the structure of Formula (VII):

(VII)

wherein the crystalline form is characterized by a reflection X-ray powder diffraction pattern comprising at least three peaks selected from the group consisting of 9.9±0.2 °2θ, 11.1±0.2 °2θ, 12.8±0.2 °2θ, 14.1±0.2 °2θ, and 19.0±0.2 °2θ.

In another aspect, the present disclosure relates to a crystalline sulfate salt of a compound having the structure of Formula (IV):

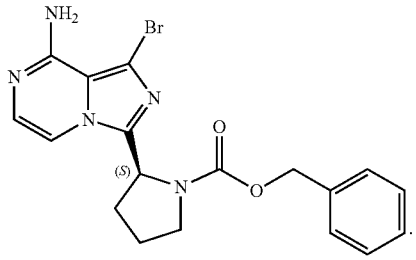

(IV)

BRIEF DESCRIPTION OF THE DRAWINGS

FIG. 1 illustrates an X-ray powder diffraction (PXRD) pattern measured in reflection mode from a sample of a crystalline sulfate salt of benzyl (2S)-2-(8-amino-1-bromo-imidazo[1,5-a]pyrazin-3-yl)-1-pyrrolidinecarboxylate having a stoichiometric ratio of about one sulfate molecule and one hydrogen sulfate molecule for every three freebase molecules.

FIG. 2 illustrates an X-ray powder diffraction (PXRD) pattern measured in reflection mode from a sample of the Type 2 crystalline form of 4-{8-amino-3-[(2S)-2-pyrrolidinyl]imidazo[1,5-a]pyrazin-1-yl}-N-(2-pyridinyl)benzamide.

FIG. 3 illustrates an X-ray powder diffraction (PXRD) pattern measured in reflection mode from a sample of the Type 3 crystalline form of 4-{8-amino-3-[(2S)-2-pyrrolidinyl]imidazo[1,5-a]pyrazin-1-yl}-N-(2-pyridinyl)benzamide.

FIG. 4 illustrates an X-ray powder diffraction (PXRD) pattern measured in reflection mode from a sample of the Form C crystalline form of 4-{8-amino-3-[(2S)-2-pyrrolidinyl]-imidazo[1,5-a]pyrazin-1-yl}-N-(2-pyridinyl)benzamide.

DETAILED DESCRIPTION OF THE INVENTION

This written description uses examples to disclose the invention and also to enable any person skilled in the art to practice the invention, including making and using any of the disclosed salts, substances, or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

I. DEFINITIONS

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "sulfate salt (2:3)" refers to a sulfate salt having a sulfate to freebase stoichiometric ratio of about 2:3, including a sulfate salt having one sulfate molecule and one hydrogen sulfate molecule for every three freebase molecules.

The term "crystalline purity," when used in reference to a crystalline form of a compound, refers to the percentage of the crystalline form relative to another crystalline form or an amorphous form of the compound in the referenced composition.

The abbreviations used throughout this disclosure have the meanings indicated in Table 1 below.

TABLE 1

| ABBREVIATION | MEANING |
|---|---|
| 2-BuOH | 2-butanol |
| DCM | dichloromethane |
| DMCC | dimethylcarbamoyl chloride |
| DMF | N,N-dimethylformamide |
| EtOH | ethanol |
| HCl | hydrochloric acid |
| HPLC | high-performance liquid chromatography |
| $H_2SO_4$ | sulfuric acid |
| IPA | isopropanol |
| kg | kilogram(s) |
| KI | potassium iodide |
| mbar | millibar |
| MeCN | acetonitrile |
| MeTHF | 2-methyltetrahydrofuran |
| mol. eq. | molar equivalent(s) |
| MTBE | methyl tert-butyl ether |

TABLE 1-continued

| ABBREVIATION | MEANING |
|---|---|
| NaCl | sodium chloride |
| $NaHCO_3$ | sodium bicarbonate |
| NaOH | sodium hydroxide |
| NBS | N-bromosuccinimide |
| $NEt_3$ | triethylamine |
| $NH_3$ | ammonia |
| NMP | N-methyl-2-pyrrolidone |
| $POCl_3$ | phosphoryl chloride |
| rel. vol. | relative volume(s) |
| $SOCl_3$ | thionyl chloride |
| TBA-Cl | tetramethylammonium chloride |
| T3P | 1-propylphosphonic acid anhydride |
| v/v | volume/volume |
| w/w | weight/weight |

For clarity, Table 2 below summarizes the compound identifier, chemical name, and structure used interchangeably throughout this application with respect to each compound discussed.

TABLE 2

| COMPOUND IDENTIFIER | NAME | STRUCTURE |
|---|---|---|
| Compound I | Benzyl (2S)-2-[(3-chloropyrazin-2-yl)methylcarbamoyl]pyrrolidine-1-carboxylate | 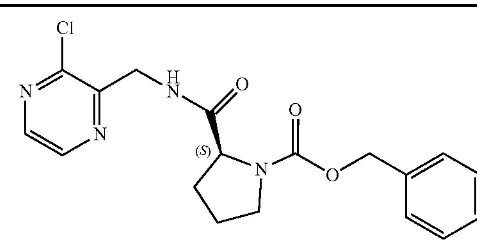 |
| Compound II | Benzyl (2S)-2-(8-chloro-imidazo-[1,5-a]pyrazin-3-yl)pyrrolidine-1-carboxylate | 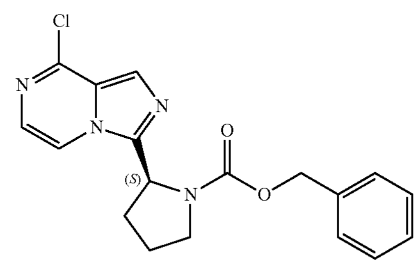 |
| Compound III | Benzyl (2S)-2-(1-bromo-8-chloro-imidazo[1,5-a]pyrazin-3-yl)-pyrrolidine-1-carboxylate | 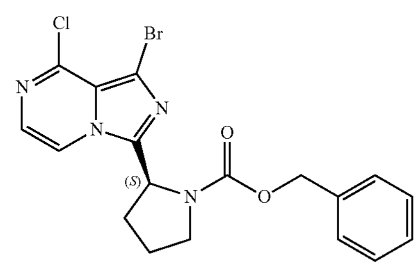 |
| Compound IV | Benzyl (2S)-2-(8-amino-1-bromo-imidazo[1,5-a]pyrazin-3-yl)-1-pyrrolidinecarboxylate | 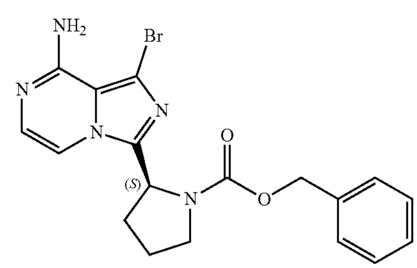 |

TABLE 2-continued

| COMPOUND IDENTIFIER | NAME | STRUCTURE |
|---|---|---|
| Compound V | [4-(2-Pyridylcarbamoyl)phenyl]-boronic acid | 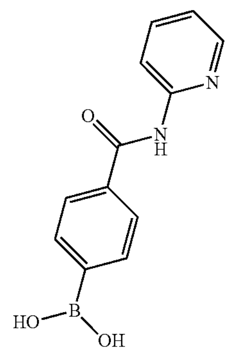 [SMILES: O=C(Nc1ccccn1)c1ccc(B(O)O)cc1] |
| Compound VI | 1-Bromo-3-[(2S)-pyrrolidin-2-yl]imidazo[1,5-a]pyrazin-8-amine | 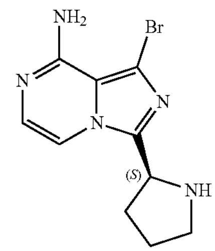 |
| Compound VII | 4-{8-Amino-3-[(2S)-2-pyrrolidinyl]-imidazo[1,5-a]-pyrazin-1-yl}-N-(2-pyridinyl)benzamide | 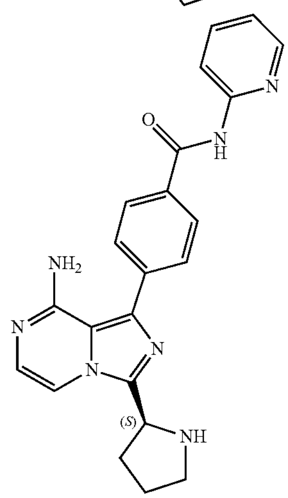 |
| Compound VIII | 4-{8-amino-3-[(2S)-1-(but-2-ynoyl)-pyrrolidin-2-yl]-imidazo[1,5-a]pyrazin-1-yl}-N-(pyridin-2-yl)benzamide (i.e., Acalabrutinib) | 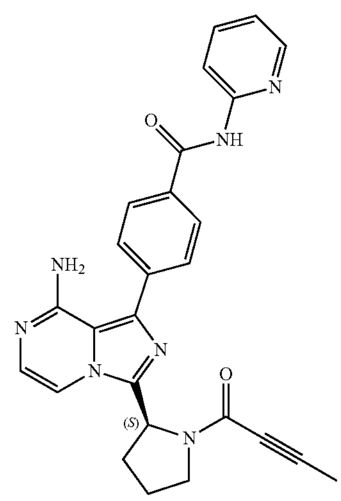 |

TABLE 2-continued

| COMPOUND IDENTIFIER | NAME | STRUCTURE |
|---|---|---|
| Compound IX | 3-[(2S)-1-benzylpyrrolidin-2-yl]-1-bromo-imidazo[1,5-a]-pyrazin-8-amine | 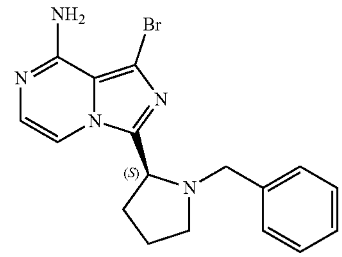 |
| Compound X | 3-[(2S)-1-[[(2S)-2(8-amino-1-bromo-imidazo[1,5-a]pyrazin-3-yl)pyrrolidin-1-yl]methyl]-pyrrolidin-2-yl]-1-bromo-imidazo[1,5-a]pyrazin-8-amine | 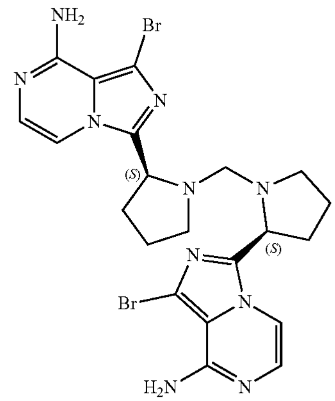 |
| Compound XI | 1-bromo-3-(3,4-dihydro-2H-pyrrol-5-yl)imidazo[1,5-a]-pyrazin-8-amine | 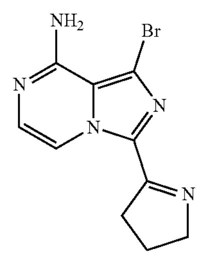 [SMILES: Nc1nccn2c(C3=NCCC3)nc(Br)c12] |
| Compound XII | 4-[8-amino-3-[(2S)-pyrrolidin-2-yl]imidazo[1,5-a]pyrazin-1-yl]-benzoic acid | 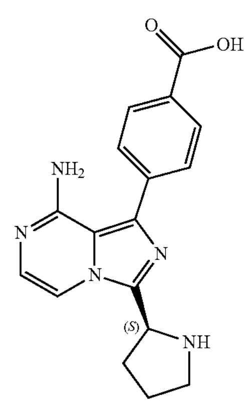 |

TABLE 2-continued

| COMPOUND IDENTIFIER | NAME | STRUCTURE |
|---|---|---|
| Compound XIII | 4-[8-amino-3-[(2S)-1-[4-[8-amino-3-[(2S)-pyrrolidin-2-yl]-imidazo[1,5-a]pyrazin-1-yl]-benzoyl]pyrrolidin-2-yl]-imidazo[1,5-a]pyrazin-1-yl]-N-(2-pyridyl)benzamide | 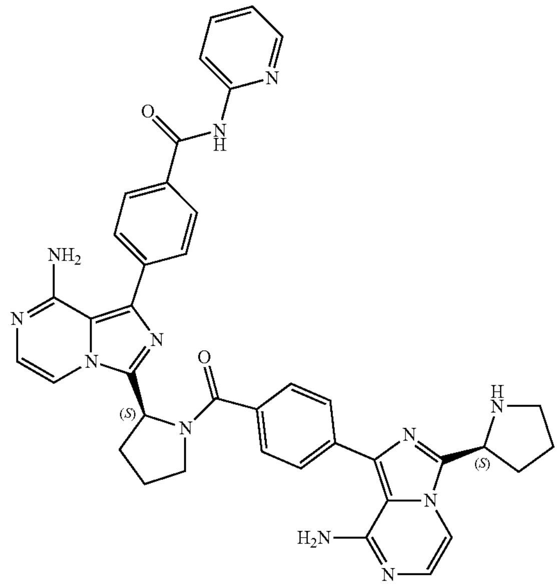 |
| Compound XIV | 4-[9-[(2S)-1-but-2-ynoyl-pyrrolidin-2-yl]-2-methyl-4-oxo-imidazo-[2,3]pyrazino[2,6-a]-pyrimidin-11-yl]-N-(2-pyridyl)benzamide | 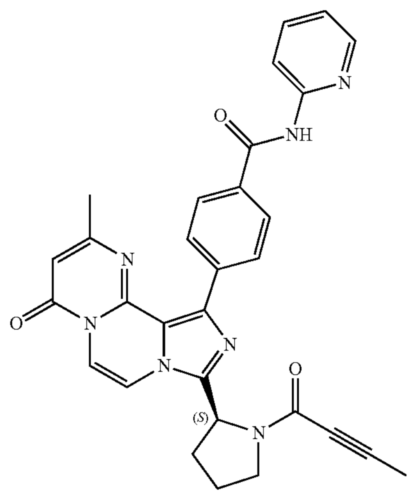 |

The present disclosure also discusses crystalline forms of certain compounds listed in Table 2, including the X-ray powder diffraction patterns characterizing such crystalline forms. It is known in the art that an X-ray powder diffraction pattern may be obtained that has one or more measurement errors depending on the measurement conditions (such as equipment, sample preparation, or the machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a powder diffraction pattern substantially identical to those disclosed herein falls within the scope of the present disclosure (for further information see Jenkins, R & Snyder, R. L. 'Introduction to X-Ray Powder Diffractometry' John Wiley & Sons, 1996).

II. U.S. Pat. No. 9,290,504 SYNTHESIS

As previously noted, the synthesis reported in Example 6 of U.S. Pat. No. 9,290,504 is not suitable for the large-scale manufacturing of acalabrutinib. Among other limitations, the reported process provides no information on the chiral or achiral purity of intermediates, employs chromatography to isolate intermediates at various points in the process, and results in milligram amounts of the final product. Overall yield of acalabrutinib from this bench scale synthesis starting from Compound I was approximately 5%.

III. CLINICAL TRIAL SUPPLY PROCESS

Scheme 3 below illustrates a process subsequently developed to manufacture supplies of acalabrutinib for clinical trials. The individual steps of Scheme 3 are discussed in further detail throughout this disclosure.

Although this process was used to produce approximately 100 to 150 kilograms of acalabrutinib for use in clinical trials, the process lacks robustness, is difficult to operate, and has a lengthy cycle time. Consequently, this process was deemed unsuitable for large-scale manufacture of acalabrutinib.

SCHEME 3

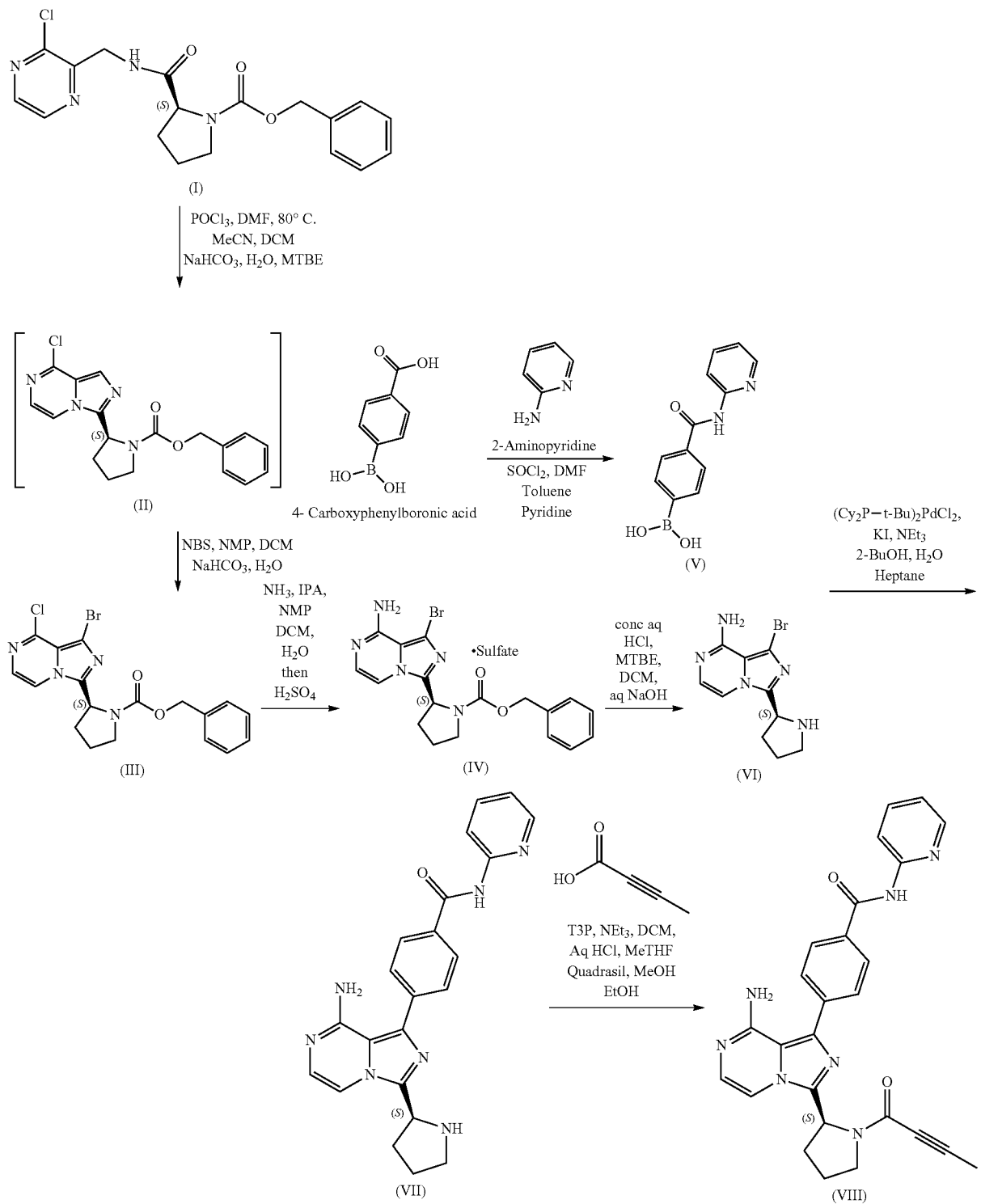

More specifically, the process of Scheme 3 has a number of limitations, including the following:

(1) Racemization of the chiral center during the step to produce Compound (II) is difficult to control and caused several batch failures.

(2) A number of environmentally undesirable solvents are employed in several of the steps.

(3) One of the more problematic solvents employed is dichloromethane. In addition to the environmental concerns, the use of dichloromethane in steps involving amines has the further disadvantage of generating aminal impurities from the reaction of the amine with dichloromethane, at times even leading to batch failures. During the step to produce Compound (VI), for instance, methylene bridged dimers can be formed. Further, the acid-based liquid chromatography analytical method used in connection with the step to produce Compound (VI) was not able to detect the aminal impurities.

(4) The use of the N,N-dimethylformamide and thionyl chloride combination used to produce Compound (V) potentially can result in the formation of toxic dimethylcarbamoyl chloride.

(5) The coupling reaction in the step to produce Compound (VII) is prone to stalling. The addition of more palladium catalyst increases the burden on the scavenging step during the final step to produce acalabrutinib, which already requires excessive repeat cycles with the silica-based scavenger.

(6) The isolation of Compound (VII) by filtration is difficult and unsuitable for large-scale manufacturing. The use of two pressure filters and multiple manual discharges of the product as a wet paste was required on 50 kg scale, and only with a significant time penalty.

(7) Multiple batch failures occurred through a variety of different failure modes for the acylation to produce acalabrutinib.

(8) The isolation of acalabrutinib using distillative precipitation provides no control over the particle properties of the isolated product.

IV. LARGE-SCALE PROCESS

In view of the limitations associated with the clinical trial supply process, an improved process that overcame those limitations and was suitable for the large-scale manufacture of acalabrutinib was developed. Scheme 4 below illustrates one representative embodiment of this large-scale process for manufacturing acalabrutinib. The individual steps of Scheme 4 are discussed in further detail throughout this disclosure.

SCHEME 4

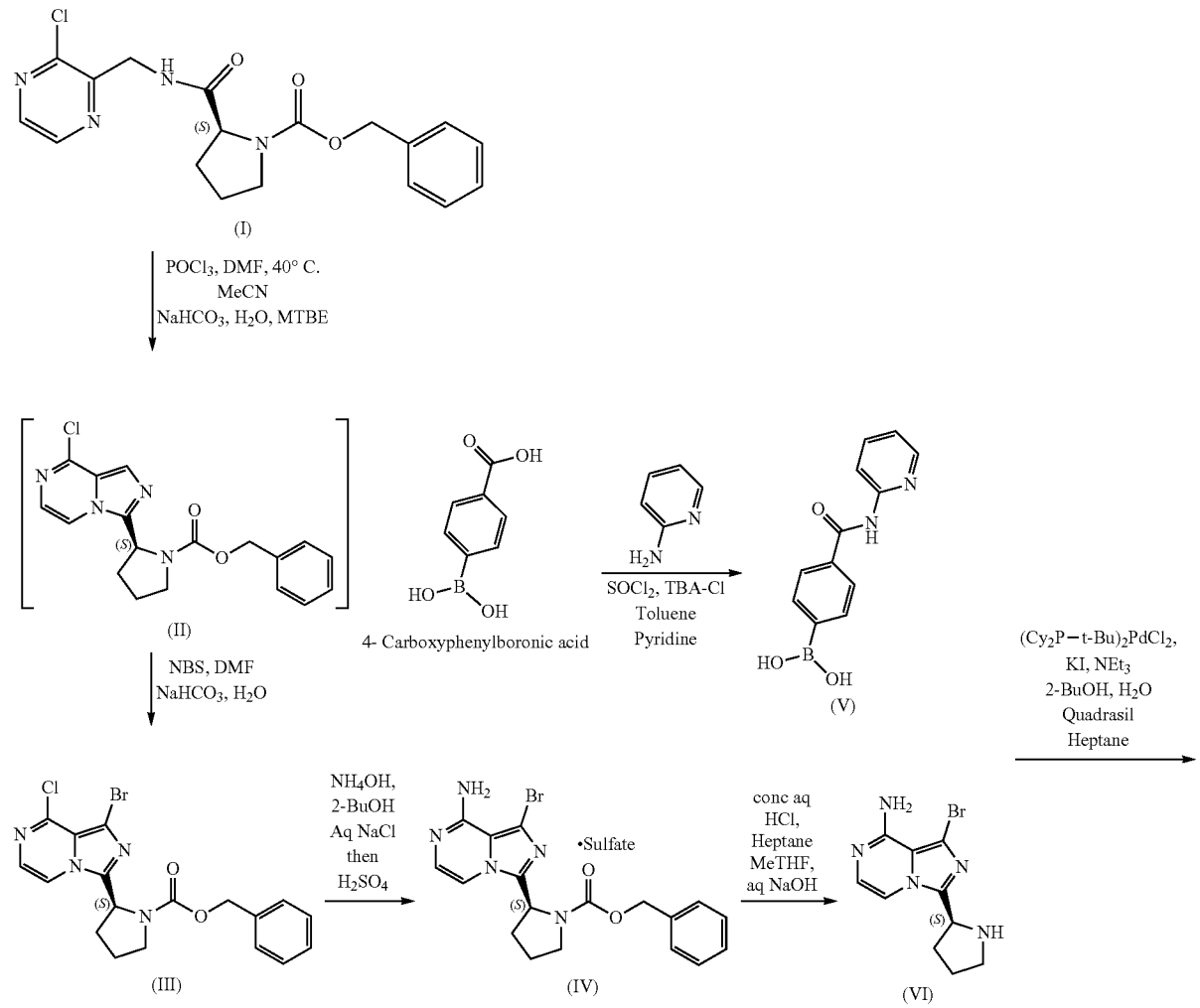

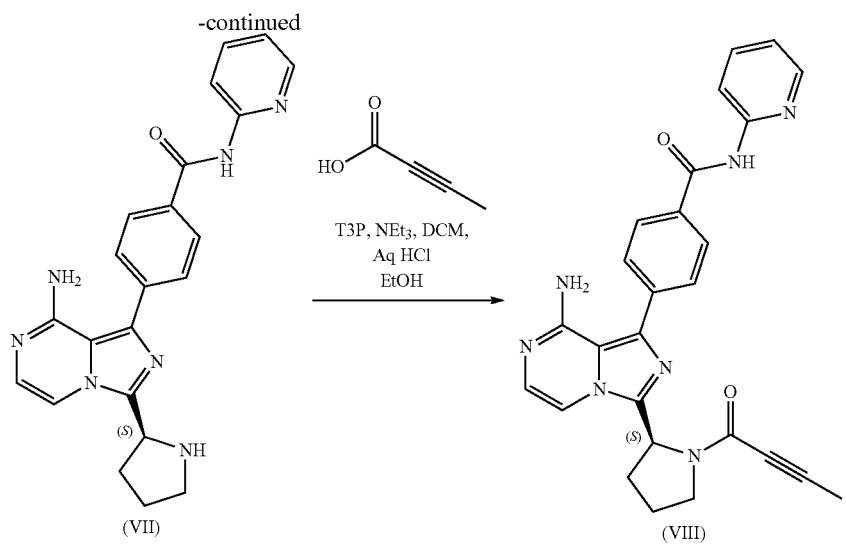

V. PREPARATION of Benzyl (2S)-2-(8-chloro-imidazo[1,5-a]pyrazin-3-yl)pyrrolidine-1-carboxylate (COMPOUND II)

The present disclosure relates, in part, to processes for preparing benzyl (2S)-2-(8-chloro-imidazo[1,5-a]pyrazin-3-yl)pyrrolidine-1-carboxylate (Compound II), or a salt thereof, from benzyl (2S)-2-[(3-chloropyrazin-2-yl)methyl-carbamoyl]pyrrolidine-1-carboxylate (Compound I), or a salt thereof. Scheme 5 below illustrates the general process:

SCHEME 5

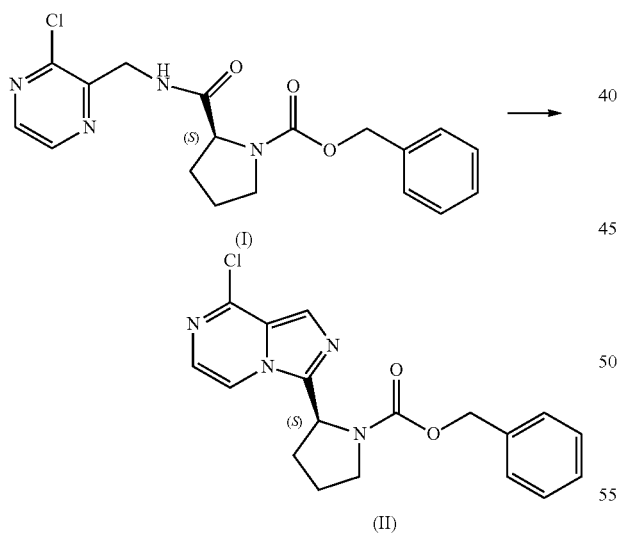

The cyclization of Compound (I) to form the imidazole ring present in Compound (II) is advantageous because it imparts stability to the chiral center of the subsequent intermediates employed in the manufacture of acalabrutinib. The clinical trial supply process, however, is problematic because uncyclized Compound (I) readily racemizes under the acidic conditions of the cyclization reaction. This undesired racemization reaction is difficult to control and has resulted in several batch failures. Use of a nitrogen sweep to remove the evolved hydrochloric acid limits to some extent the chiral erosion that occurs, but the extent of chiral erosion is still highly variable.

The clinical trial supply process employed a reaction temperature around 80° C. with an N,N-dimethylformamide catalytic charge around 0.2 molar equivalents. It has now been determined that increasing the N,N-dimethylformamide charge (e.g., to about 0.6 molar equivalents) and reducing the reaction temperature (e.g., to about 40° C.) limits the chiral degradation observed and routinely results in the production of chirally pure Compound (II). The lower N,N-dimethylformamide catalytic charge employed in the clinical trial supply process resulted in a reaction rate that required a higher temperature for reaction completion which then lead to the chiral degradation observed. In contrast, the increased N,N-dimethylformamide catalytic charge of the improved process results in a faster reaction rate and allows the reaction to be carried out at a lower temperature which suppresses the racemization. The chiral degradation is reduced, the chiral integrity is maintained, and the yield is therefore improved.

Accordingly, in one embodiment, the present disclosure relates to a process for preparing a compound having the structure of Formula (II):

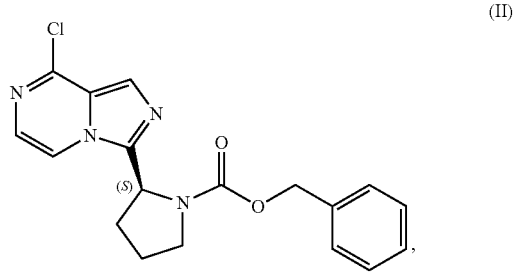

(II)

or a salt thereof, wherein the process comprises:
  contacting a compound having the structure of Formula (I):

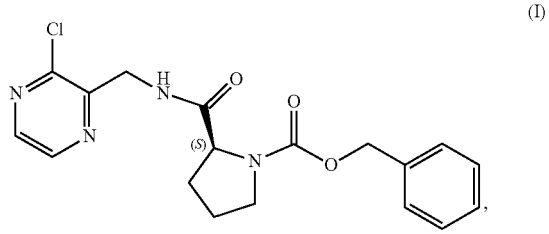

or a salt thereof, with a cyclizing agent in the presence of a catalyst in a reaction medium to form the compound of Formula (II), or salt thereof;
  wherein the temperature of the reaction medium is controlled during the contacting step in a manner sufficient to maintain a chiral purity of at least about 80% for the compound of Formula (II), or salt thereof.

As noted above, appropriate control of the reaction temperature during the cyclizing reaction is important for maintaining suitable chiral purity of the product. In general, the temperature of the reaction medium is controlled during the cyclizing reaction in a manner sufficient to maintain a chiral purity of at least about 85% for the compound of Formula (II), or salt thereof. In one aspect, the temperature of the reaction medium is controlled during the contacting step in a manner sufficient to maintain a chiral purity of at least about 90% for the compound of Formula (II), or salt thereof. In another aspect, the temperature of the reaction medium is controlled during the contacting step in a manner sufficient to maintain a chiral purity of at least about 95% for the compound of Formula (II), or salt thereof. In another aspect, the temperature of the reaction medium is controlled during the contacting step in a manner sufficient to maintain a chiral purity of at least about 99% for the compound of Formula (II), or salt thereof.

Maintaining the reaction medium at a temperature less than about 80° C. during the contacting step generally improves the chiral purity of the compound of Formula (II), or salt thereof. In one aspect, the reaction medium is maintained at a temperature less than about 70° C. during the contacting step. In another aspect, the reaction medium is maintained at a temperature less than about 60° C. during the contacting step. In another aspect, the reaction medium is maintained at a temperature less than about 50° C. during the contacting step. In another aspect, the reaction medium is maintained at a temperature from about 30° C. to about 50° C. during the contacting step. In another aspect, the reaction medium is maintained at a temperature of about 40° C. during the contacting step.

The catalyst can comprise any suitable catalyst, particularly a catalyst selected from the group consisting of N,N-dimethylformamide and N-methylformanilide. In one aspect, the catalyst comprises N,N-dimethylformamide. In another aspect, the catalyst comprises N-methylformanilide. As noted above, the amount of catalyst charged to the reaction medium also can affect the chiral purity of the product. At least about 0.1 molar equivalents of the catalyst generally are charged to the reaction medium relative to the compound of Formula (I), or salt thereof. In one aspect, at least about 0.4 molar equivalents of the catalyst are charged to the reaction medium relative to the compound of Formula (I), or salt thereof. In a further aspect, at least about 0.6 molar equivalents of the catalyst are charged to the reaction medium relative to the compound of Formula (I), or salt thereof. In a further aspect, about 0.1 to about 1.0 molar equivalents of the catalyst are charged to the reaction medium relative to the compound of Formula (I), or salt thereof. In a further aspect, about 0.4 to about 1.0 molar equivalents of the catalyst are charged to the reaction medium relative to the compound of Formula (I), or salt thereof. In a further aspect, the catalyst comprises N,N-dimethylformamide, and from about 0.1 to about 1.0 molar equivalents of the catalyst are charged to the reaction medium relative to the compound of Formula (I), or salt thereof. In a further aspect, the catalyst comprises N,N-dimethylformamide, and about 0.4 to about 1.0 molar equivalents of the catalyst are charged to the reaction medium relative to the compound of Formula (I), or salt thereof. In a further aspect, the catalyst comprises N,N-dimethylformamide, and about 0.6 molar equivalents of the catalyst are charged to the reaction medium relative to the compound of Formula (I), or salt thereof.

The cyclizing agent can be any suitable cyclizing agent, particularly phosphorus oxychloride. The compound of Formula (I), or salt thereof, generally is contacted with about 0.7 to about 10 molar equivalents of the cyclizing agent relative to the compound of Formula (I), or salt thereof. In one aspect, the compound of Formula (I), or salt thereof, is contacted with about 1.5 to about 2.5 molar equivalents of the cyclizing agent relative to the compound of Formula (I), or salt thereof. In another aspect, the compound of Formula (I), or salt thereof, is contacted with about 2.0 molar equivalents of the cyclizing agent relative to the compound of Formula (I), or salt thereof.

The reaction medium can be any suitable reaction medium, particularly one comprising at least one solvent selected from the group consisting of aromatic hydrocarbons, chlorinated hydrocarbons, ethers, and nitriles. In one aspect, the reaction medium comprises at least one compound selected from the group consisting of acetonitrile, butyronitrile, dichloromethane, toluene, anisole, tetrahydrofuran, and 2-methyltetrahydrofuran. In another aspect, the reaction medium comprises acetonitrile. The volume of reaction medium generally is about 2 liters to about 20 liters of reaction medium per kilogram of the compound of Formula (I), or salt thereof, charged to the reaction medium. In one aspect, the volume of reaction medium is about 3 liters to about 10 liters of reaction medium per kilogram of the compound of Formula (I), or salt thereof, charged to the reaction medium.

The contacting step generally is carried out as a batch reaction, particularly one where at least about 50 kilograms of the compound of Formula (I), or salt thereof, are charged to the batch reaction. In one aspect, at least about 100 kilograms of the compound of Formula (I), or salt thereof, are charged to the batch reaction. In another aspect, at least about 200 kilograms of the compound of Formula (I), or salt thereof, are charged to the batch reaction. In another aspect, at least about 300 kilograms of the compound of Formula (I), or salt thereof, are charged to the batch reaction.

The process generally provides at least about a 50% stoichiometric process yield of the compound of Formula (II), or salt thereof. In one aspect, the stoichiometric process yield of the compound of Formula (II), or salt thereof, is at least about 65%. In another aspect, the stoichiometric process yield of the compound of Formula (II), or salt thereof, is at least about 80%. In another aspect, the stoichiometric process yield of the compound of Formula (II), or salt thereof, is at least about 90%. In fact, the improved process has been able to deliver an approximately 95% yield of good quality material at over 300 kg (input) scale.

In another representative embodiment, the present disclosure relates to a process for preparing a compound having the structure of Formula (II):

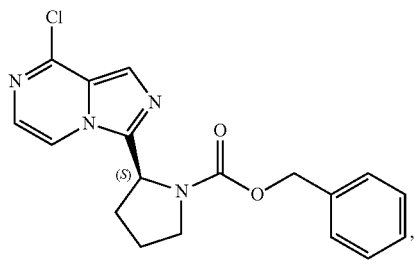
(II)

or a salt thereof, wherein the process comprises:
contacting a compound having the structure of Formula (I):

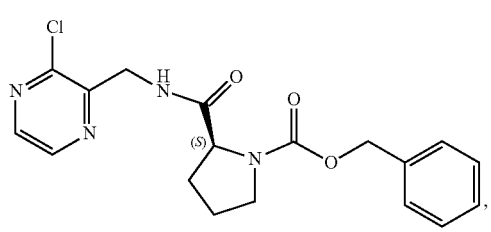
(I)

or a salt thereof, with phosphorus oxychloride in the presence of a catalyst in a reaction medium to form the compound of Formula (II), or salt thereof;
wherein the reaction medium is maintained at a temperature less than about 80° C. during the contacting step;
wherein at least about 0.4 molar equivalents of the catalyst are charged to the reaction medium relative to the compound of Formula (I), or salt thereof; and
wherein the chiral purity of the compound of Formula (II), or salt thereof, is at least about 80%.

In one aspect, the reaction medium is maintained at a temperature less than about 70° C. during the contacting step; at least about 0.4 to about 1.0 molar equivalents of the catalyst are charged to the reaction medium relative to the compound of Formula (I), or salt thereof; and the chiral purity of the compound of Formula (II), or salt thereof, is at least about 85%. In another aspect, the reaction medium is maintained at a temperature less than about 60° C. during the contacting step; at least about 0.4 to about 1.0 molar equivalents of the catalyst are charged to the reaction medium relative to the compound of Formula (I), or salt thereof; and the chiral purity of the compound of Formula (II), or salt thereof, is at least about 90%. In another aspect, the reaction medium is maintained at a temperature from about 30° C. to about 50° C. during the contacting step; at least about 0.4 to about 1.0 molar equivalents of the catalyst are charged to the reaction medium relative to the compound of Formula (I), or salt thereof; and the chiral purity of the compound of Formula (II), or salt thereof, is at least about 90%. In another aspect, the reaction medium is maintained at a temperature of about 40° C. during the contacting step; about 0.6 molar equivalents of the catalyst are charged to the reaction medium relative to the compound of Formula (I), or salt thereof; and the chiral purity of the compound of Formula (II), or salt thereof, is at least about 90%. In a further aspect, the catalyst comprises N,N-dimethylformamide.

Scheme 6 below corresponds to the process described in Example 3 and illustrates one representative embodiment of the improved process for preparing Compound (II).

SCHEME 6

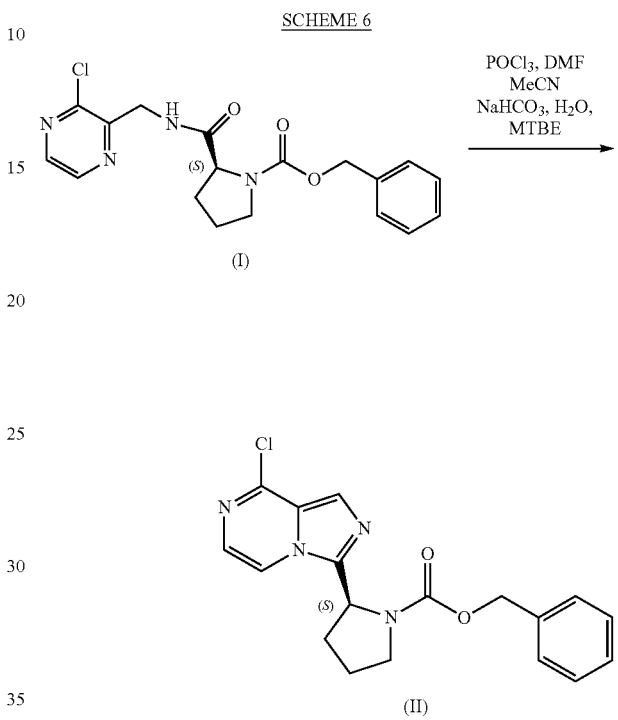

VI. PREPARATION of Benzyl (2S)-2-(1-bromo-8-chloro-imidazo[1,5-a]pyrazin-3-yl)-pyrrolidine-1-carboxylate (COMPOUND III)

The present disclosure relates, in part, to processes for preparing benzyl (2S)-2-(1-bromo-8-chloro-imidazo[1,5-a]pyrazin-3-yl)pyrrolidine-1-carboxylate (Compound III), or a salt thereof, from benzyl (2S)-2-[(3-chloropyrazin-2-yl)methylcarbamoyl]pyrrolidine-1-carboxylate (Compound I), or a salt thereof. Compound (II), or a salt thereof, is prepared from Compound (I), or a salt thereof, as previously discussed and then is brominated to produce Compound (III), or a salt thereof. Scheme 7 below illustrates the general process:

SCHEME 7

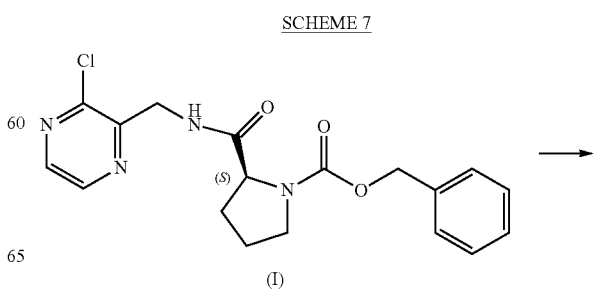

-continued

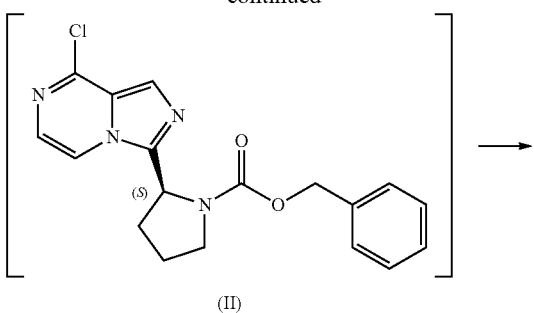

(II)

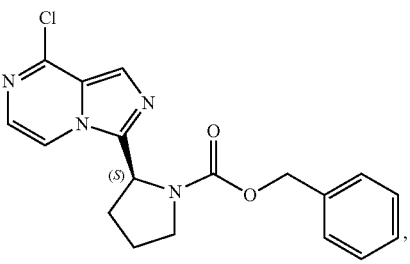

(II)

or salt thereof; and
brominating the compound of Formula (II), or salt thereof, with a brominating agent to provide a compound having the structure of Formula (III):

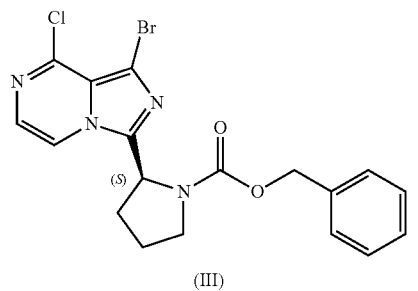

(III)

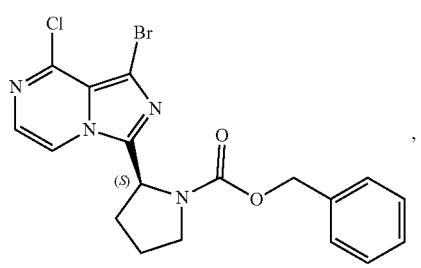

(III)

or a salt thereof;
wherein the temperature of the reaction medium is controlled during the contacting step in a manner sufficient to maintain a chiral purity of at least about 80% for the compound of Formula (II), or salt thereof.

Accordingly, in one embodiment, the present disclosure relates to a process for preparing a compound having the structure of Formula (III):

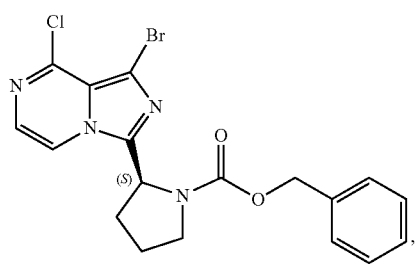

(III)

or a salt thereof, wherein the process comprises:
contacting a compound having the structure of Formula (I):

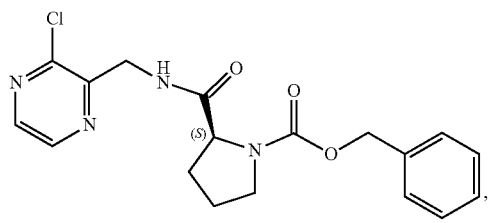

(I)

or a salt thereof, with a cyclizing agent in the presence of a catalyst in a reaction medium to form a compound of Formula (II):

The brominating agent can be any suitable brominating agent, particularly N-bromosuccinimide. The compound of Formula (III), or salt thereof, can be prepared from the compound of Formula (II), or salt thereof, without first isolating the compound of Formula (II), or salt thereof, from the reaction mixture (i.e., in situ bromination which can include a solvent exchange step), or, alternatively, the compound of Formula (II), or salt thereof, can be isolated from the reaction medium and then brominated to provide the compound of Formula (III), or salt thereof. In one aspect, the compound of Formula (III), or salt thereof, is prepared from the compound of Formula (II), or salt thereof, without first isolating the compound of Formula (II), or salt thereof, from the reaction mixture (i.e., in situ bromination). In another aspect, the compound of Formula (II), or salt thereof, is isolated from the reaction medium (e.g., a solvent exchange process comprising the isolation of an oil comprising the compound of Formula (II), or salt thereof) and then brominated to provide the compound of Formula (III), or salt thereof.

Where the compound of Formula (II), or a salt thereof, is isolated from the reaction mixture and then contacted with the brominating agent in a bromination medium, the bromination medium can be any suitable bromination medium, particularly one comprising at least one solvent selected from the group consisting of chlorinated hydrocarbons and polar aprotic solvents. In one aspect, the bromination medium comprises at least one solvent selected from the group consisting of N,N-dimethylformamide, N-methylpyrrolidinone, N-butylpyrrolidinone, dimethylsulphoxide, dimethylacetamide, and dichloromethane. In another aspect, the bromination medium comprises N,N-dimethylformamide. In another aspect, the bromination medium comprises N-methylpyrrolidinone.

The compound of Formula (II), or salt thereof, is contacted with an effective amount of the brominating agent, for example, about 0.8 to about 1.2 molar equivalents of the brominating agent relative to the compound of Formula (II), or salt thereof. To avoid over-reaction, it may be beneficial to "titrate in" the brominating agent, control the temperature of the reaction medium/bromination medium during the addition of the brominating agent, and/or conduct repeat in-process control measurements during the addition of the brominating agent. In one aspect, the reaction medium/bromination medium is maintained at a temperature from about 5° C. to about 40° C. during the brominating step. In another aspect, the reaction medium/bromination medium is maintained at a temperature of about 20° C. during the brominating step. In another aspect, the brominating agent is titrated into the reaction medium/bromination medium.

The process may further comprise isolating the compound of Formula (III), or salt thereof, from the final reaction mixture. In one aspect, an aqueous solution is added to the final reaction mixture to precipitate the compound of Formula (III), or salt thereof. In another aspect, an aqueous solution having a basic pH is added to the final reaction mixture to precipitate the compound of Formula (III), or salt thereof. In another aspect, an aqueous sodium bicarbonate solution is added to the final reaction mixture to precipitate the compound of Formula (III), or salt thereof. In another aspect, the sodium bicarbonate solution is about 1 weight % to 10 weight % sodium bicarbonate. In another aspect, the sodium bicarbonate solution is about 2 weight % sodium bicarbonate.

Where Compound (II), or a salt thereof, is isolated from the reaction mixture and then brominated, the bromination generally is carried out as a batch reaction, particularly one where at least about 50 kilograms of the compound of Formula (II), or salt thereof, are charged to the batch reaction. In one aspect, at least about 100 kilograms of the compound of Formula (II), or salt thereof, are charged to the batch reaction. In another aspect, at least about 200 kilograms of the compound of Formula (II), or salt thereof, are charged to the batch reaction. In another aspect, at least about 300 kilograms of the compound of Formula (II), or salt thereof, are charged to the batch reaction.

Where Compound (II), or a salt thereof, is brominated in situ, the in situ reaction generally is carried out as a batch reaction, particularly one where at least about 50 kilograms of the compound of Formula (I), or salt thereof, are initially charged to the reaction. In one aspect, at least about 100 kilograms of the compound of Formula (I), or salt thereof, are initially charged to the reaction. In another aspect, at least about 200 kilograms of the compound of Formula (I), or salt thereof, are initially charged to the reaction. In another aspect, at least about 300 kilograms of the compound of Formula (I), or salt thereof, are initially charged to the reaction.

Reacting Compound (II), or a salt thereof, with a brominating agent (e.g., N-bromosuccinimide) to produce Compound (III), or a salt thereof, generally works well and delivers good quality material in high yield. The process generally provides at least about a 50% stoichiometric process yield of the compound of Formula (III), or salt thereof. In one aspect, the stoichiometric process yield of the compound of Formula (III), or salt thereof, is at least about 65%. In another aspect, the stoichiometric process yield of the compound of Formula (III), or salt thereof, is at least about 80%. In another aspect, the stoichiometric process yield of the compound of Formula (III), or salt thereof, is at least about 90%. In fact, the improved process has been able to deliver approximately 95% yield of good quality material at over 300 kg (input) scale.

In another representative embodiment, the present disclosure relates to a process for preparing a compound having the structure of Formula (III):

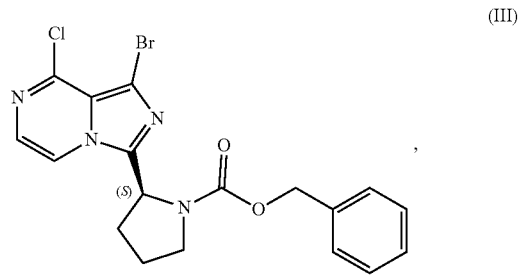

(III)

or a salt thereof, wherein the process comprises:

contacting a compound having the structure of Formula (I):

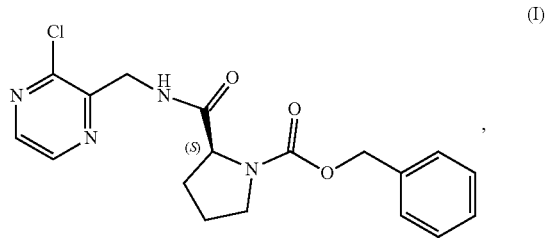

(I)

or a salt thereof, with phosphorus oxychloride in the presence of a catalyst in a reaction medium to form a compound of Formula (II):

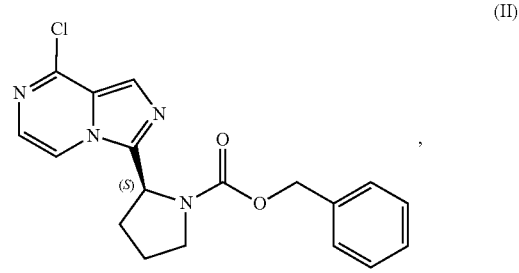

(II)

or salt thereof; and brominating the compound of Formula (II), or salt thereof, with N-bromosuccinimide to provide a compound having the structure of Formula (III):

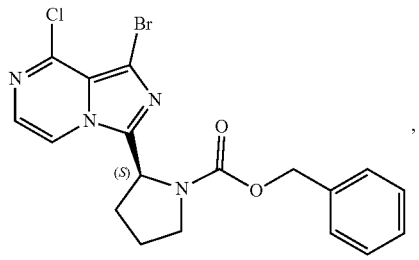

(III)

or a salt thereof;
wherein the reaction medium is maintained at a temperature less than about 80° C. during the contacting step;
wherein at least about 0.4 molar equivalents of the catalyst are charged to the reaction medium relative to the compound of Formula (I), or salt thereof; and
wherein the chiral purity of the compound of Formula (II), or salt thereof, is at least about 80%.

In one aspect, the reaction medium is maintained at a temperature less than about 70° C. during the contacting step; at least about 0.4 to about 1.0 molar equivalents of the catalyst are charged to the reaction medium relative to the compound of Formula (I), or salt thereof; and the chiral purity of the compound of Formula (II), or salt thereof, is at least about 85%. In another aspect, the reaction medium is maintained at a temperature less than about 60° C. during the contacting step; at least about 0.4 to about 1.0 molar equivalents of the catalyst are charged to the reaction medium relative to the compound of Formula (I), or salt thereof; and the chiral purity of the compound of Formula (II), or salt thereof, is at least about 90%. In another aspect, the reaction medium is maintained at a temperature from about 30° C. to about 50° C. during the contacting step; at least about 0.4 to about 1.0 molar equivalents of the catalyst are charged to the reaction medium relative to the compound of Formula (I), or salt thereof; and the chiral purity of the compound of Formula (II), or salt thereof, is at least about 90%. In another aspect, the reaction medium is maintained at a temperature of about 40° C. during the contacting step; about 0.6 molar equivalents of the catalyst are charged to the reaction medium relative to the compound of Formula (I), or salt thereof; and the chiral purity of the compound of Formula (II), or salt thereof, is at least about 90%. In a further aspect, the catalyst comprises N,N-dimethylformamide.

Scheme 8 below corresponds to the process described in Example 3 and illustrates one representative embodiment of the improved process for preparing Compound (III), or a salt thereof.

SCHEME 8

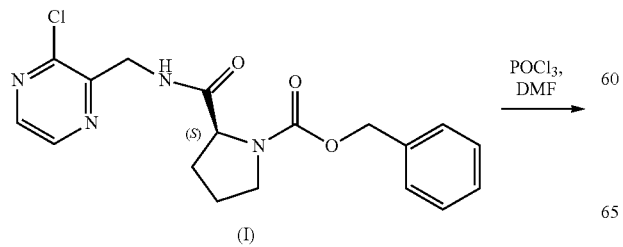

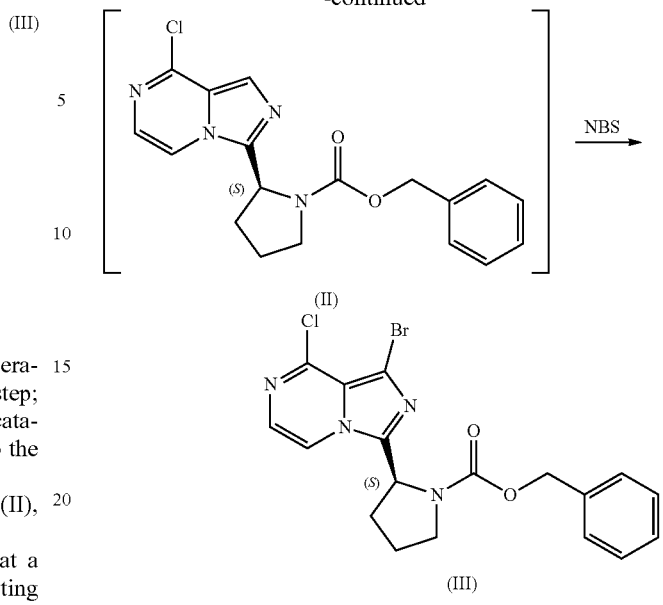

VII. PREPARATION of Benzyl (2S)-2-(8-amino-1-bromoimidazo[1,5-a]pyrazin-3-yl)-1-pyrrolidinecarboxylate (Compound IV) AND CORRESPONDING SULFATE SALT (2:3)

The present disclosure relates, in part, to processes for preparing benzyl (2S)-2-(8-amino-1-bromoimidazo[1,5-a]pyrazin-3-yl)-1-pyrrolidinecarboxylate (Compound IV), or a salt thereof, from benzyl (2S)-2-(1-bromo-8-chloro-imidazo[1,5-a]pyrazin-3-yl)pyrrolidine-1-carboxylate (Compound III), or a salt thereof. Scheme 9 below illustrates the general process:

SCHEME 9

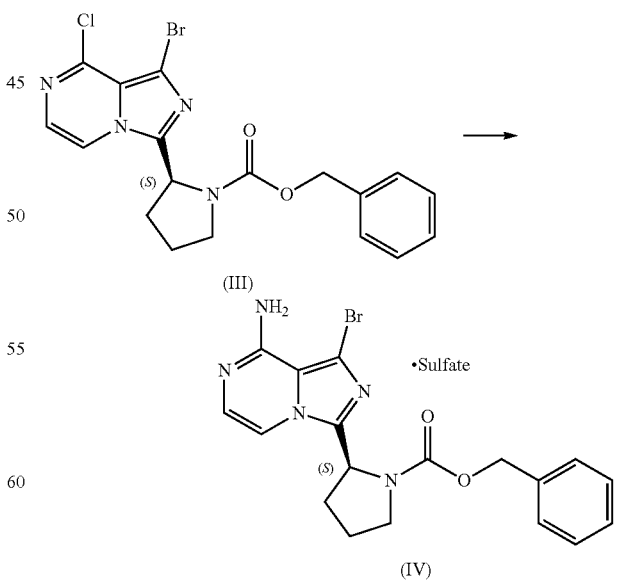

As reflected in Scheme 9 above, Compound (III), or a salt thereof, is aminated with an aminating agent (e.g., ammonia, ammonium hydroxide, etc.) to produce Compound (IV) which optionally can be converted to a salt, particularly a sulfate salt of Compound (IV), as discussed further below. Because the amination reaction can result in the presence of residual ammonia, it can be beneficial (particularly where a sulfate salt of Compound (IV) is desired) to reduce the amount of residual ammonia present prior to forming a salt of Compound (IV) (e.g., through distillation of the crude Compound (IV) product). If residual ammonia present with Compound (IV) has not been sufficiently removed when a sulfate salt is generated, for example, inorganic ammonium sulfate may be produced in addition to the sulfate salt of Compound (IV) and cause difficulty in determining the exact stoichiometry of the sulfate salt produced. From a regulatory perspective, an understanding of the exact stoichiometry of the sulfate salt produced may be needed (e.g., where the sulfate salt is a registered starting material for regulatory purposes).

Accordingly, in one embodiment, the present disclosure relates to a process for preparing a sulfate salt of a compound having the structure of Formula (IV):

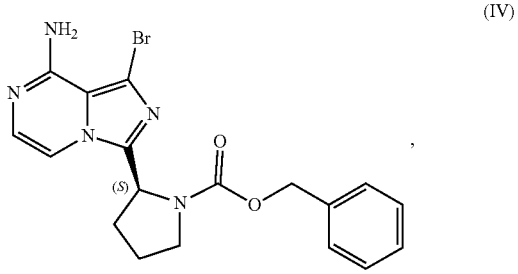

(IV)

wherein the process comprises:
contacting a compound having the structure of Formula (III):

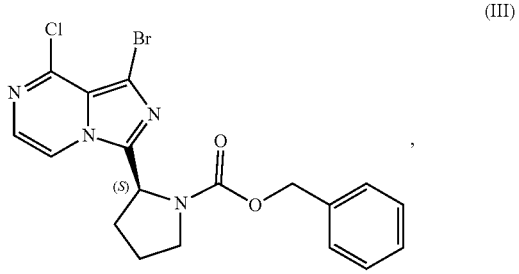

(III)

or a salt thereof, with an aminating agent in a reaction medium to form a reaction mixture comprising the compound of Formula (IV);
forming a sulfate salt of the compound of Formula (IV); and
isolating the sulfate salt.

In general, the sulfate salt of the compound having the structure of Formula (IV) has a stoichiometric ratio of one sulfate molecule and one hydrogen sulfate molecule to three freebase molecules. In one aspect, the sulfate salt is a crystalline salt. In another aspect, the crystalline sulfate salt is characterized by a reflection X-ray powder diffraction pattern comprising at least three peaks selected from the group consisting of 7.7±0.2 °2θ, 10.6±0.2 °2θ, 11.1±0.2 °2θ, 12.6±0.2 °2θ, and 13.5±0.2 °2θ. In another aspect, the crystalline sulfate salt is characterized by a reflection X-ray powder diffraction pattern comprising at least three peaks selected from the group consisting of 7.7±0.2 °2θ, 10.6±0.2 °2θ, 11.1±0.2 °2θ, 12.6±0.2 °2θ, 13.5±0.2 °2θ, 17.4±0.2 °2θ, 18.0±0.2 °2θ, 18.9±0.2 °2θ, 19.2±0.2 °2θ, and 21.9±0.2 °2θ.

The isolated crystalline sulfate salt generally has a crystalline purity of at least 50%. In one aspect, the isolated crystalline sulfate salt has a crystalline purity of at least 60%. In another aspect, the isolated crystalline sulfate salt has a crystalline purity of at least 70%. In another aspect, the isolated crystalline sulfate salt has a crystalline purity of at least 80%. In another aspect, the isolated crystalline sulfate salt has a crystalline purity of at least 90%. In another aspect, the isolated crystalline sulfate salt has a crystalline purity of at least 95%. In another aspect, the isolated crystalline sulfate salt has a crystalline purity of at least 96%. In another aspect, the isolated crystalline sulfate salt has a crystalline purity of at least 97%. In another aspect, the isolated crystalline sulfate salt has a crystalline purity of at least 98%. In another aspect, the isolated crystalline sulfate salt has a crystalline purity of at least 99%. In another aspect, the isolated crystalline sulfate salt is substantially phase pure.

The aminating agent can be any suitable aminating agent, particularly ammonia or ammonium hydroxide. In one aspect, the aminating agent is gaseous ammonia. In another aspect, the aminating agent is ammonium hydroxide. The compound of Formula (III), or salt thereof, generally is contacted with an effective amount of the aminating agent, for example, about 5 to about 20 molar equivalents of the aminating agent relative to the compound of Formula (III), or salt thereof.

The reaction medium can be any suitable reaction medium, particularly one comprising at least one solvent selected from the group consisting of alkyl hydrocarbons, aromatic hydrocarbons, chlorinated hydrocarbons, aromatic heterocycles, alcohols, ethers, and dipolar aprotic solvents. In one aspect, the reaction medium comprises at least one compound selected from the group consisting of methanol, ethanol, propanol, butanol, pentanol, N-methylpyrrolidinone, and N,N-dimethylformamide. In another aspect, the reaction medium comprises an aliphatic alcohol. In another aspect, the reaction medium comprises butanol. In another aspect, the reaction medium comprises 2-butanol. The volume of reaction medium generally is about 1.5 liters to about 40 liters of reaction medium per kilogram of the compound of Formula (III), or salt thereof, charged to the reaction medium. In one aspect, the volume of reaction medium is about 2.0 liters to about 30 liters of reaction medium per kilogram of the compound of Formula (III), or salt thereof, charged to the reaction medium.

During the contacting step, the reaction medium generally is maintained at a temperature above 70° C. In one aspect, the reaction medium is maintained at a temperature above 90° C. during the contacting step. In another aspect, the reaction medium is maintained at a temperature from about 50° C. to about 100° C. during the contacting step. In another aspect, the reaction medium is maintained at a temperature from about 60° C. to about 95° C. during the contacting step.

The contacting step generally is carried out as a batch reaction, particularly one where at least about 50 kilograms of the compound of Formula (III), or salt thereof, are charged to the batch reaction. In one aspect, at least about 100 kilograms of the compound of Formula (III), or salt thereof, are charged to the batch reaction. In another aspect, at least about 200 kilograms of the compound of Formula (II), or salt thereof, are charged to the batch reaction. In another aspect, at least about 300 kilograms of the compound of Formula (III), or salt thereof, are charged to the batch reaction.

Where a sulfate salt of Compound (IV) is desired, the forming step generally comprises contacting the compound of Formula (IV) with sulfuric acid to form a sulfate salt mixture comprising the sulfate salt. In one aspect, the compound of Formula (IV) is contacted with at least about 0.8 molar equivalents of sulfuric acid relative to the compound of Formula (III). In another aspect, the compound of Formula (IV) is contacted with about 1.25 to about 1.75 molar equivalents of sulfuric acid relative to the compound of Formula (III).

The process optionally comprises isolating the compound of Formula (IV) from the reaction mixture as a freebase prior to the forming step. Isolation of the freebase prior to the salt conversion may be beneficial in reducing the amount of residual ammonia present and avoiding potential problems associated with the presence of residual ammonia. In one aspect, the process comprises isolating the compound of Formula (IV) from the reaction medium as a freebase; contacting the freebase with sulfuric acid to form a sulfate salt; and isolating the sulfate salt. In another aspect, the process comprises washing the reaction mixture to reduce the amount of ammonia present in the reaction mixture; isolating the compound of Formula (IV) from the washed reaction medium as a freebase; contacting the freebase with sulfuric acid to form a sulfate salt; and isolating the sulfate salt. In another aspect, the process comprises washing the reaction mixture with a brine solution; distilling the washed reaction mixture to reduce the amount of ammonia present in the washed reaction mixture; isolating the compound of Formula (IV) from the distilled reaction medium as a freebase; contacting the freebase with sulfuric acid to form a sulfate salt; and isolating the sulfate salt. In another aspect, the sulfate salt is isolated by filtration.

The process generally provides at least about a 50% stoichiometric process yield of the sulfate salt of Formula (IV). In one aspect, the stoichiometric process yield of the compound of sulfate salt of Formula (IV) is at least about 65%. In another aspect, the stoichiometric process yield of the sulfate salt of Formula (IV) is at least about 75%. In fact, the improved process has been able to deliver an approximately 85% yield of good quality material at over 300 kg (input) scale.

In another representative embodiment, the present disclosure relates to a process for preparing a sulfate salt of a compound having the structure of Formula (IV):

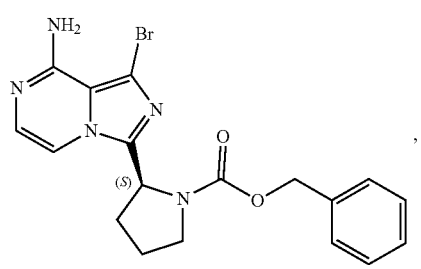

(IV)

wherein the process comprises:
contacting a compound having the structure of Formula (III):

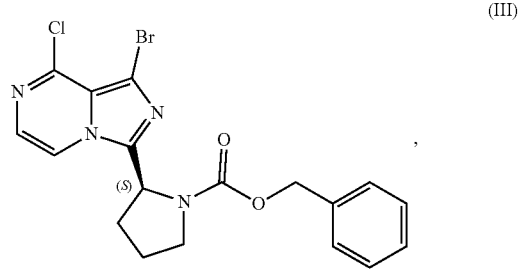

(III)

or a salt thereof, with an aminating agent in a reaction medium to form a reaction mixture comprising the compound of Formula (IV);
isolating the compound of Formula (IV) from the reaction mixture as a freebase;
contacting the freebase with sulfuric acid to form a sulfate salt of the compound of Formula (IV); and
isolating the sulfate salt; wherein the sulfate salt has a stoichiometric ratio of one sulfate molecule and one hydrogen sulfate molecule to three freebase molecules.

In one aspect, the sulfate salt is a crystalline salt. In another aspect, the crystalline sulfate salt is characterized by a reflection X-ray powder diffraction pattern comprising at least three peaks selected from the group consisting of 7.7±0.2 °2θ, 10.6±0.2 °2θ, 11.1±0.2 °2θ, 12.6±0.2 °2θ, and 13.5±0.2 °2θ. In another aspect, the crystalline sulfate salt is characterized by a reflection X-ray powder diffraction pattern comprising at least three peaks selected from the group consisting of 7.7±0.2 °2θ, 10.6±0.2 °2θ, 11.1±0.2 °2θ, 12.6±0.2 °2θ, 13.5±0.2 °2θ, 17.4±0.2 °2θ, 18.0±0.2 °2θ, 18.9±0.2 °2θ, 19.2±0.2 °2θ, and 21.9±0.2 °2θ. In another aspect, the crystalline sulfate salt is characterized by a reflection X-ray powder diffraction pattern comprising at least five peaks selected from the group of peaks.

Scheme 10 below corresponds to the process described in Example 5 and illustrates one representative embodiment of the improved process for preparing Compound (II).

SCHEME 10

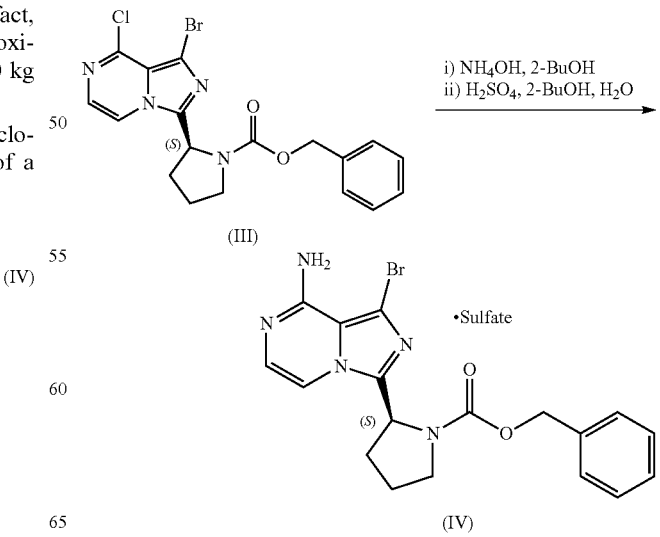

VIII. PREPARATION of 4-(2-Pyridylcarbamoyl)phenyl]boronic acid (COMPOUND V)

The present disclosure relates, in part, to processes for preparing 4-(2-pyridyl-carbamoyl)phenyl]boronic acid (Compound V), or a salt thereof, from 4-carboxyphenylboronic acid, or a salt thereof, and 2-aminopyridine. Scheme 11 below illustrates the general process:

SCHEME 11

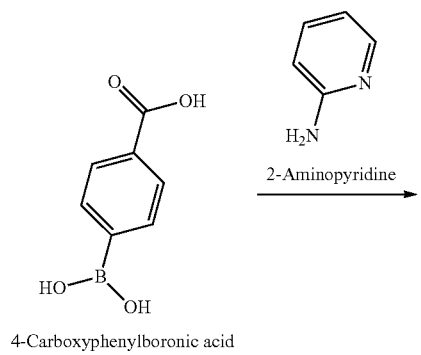

4-Carboxyphenylboronic acid

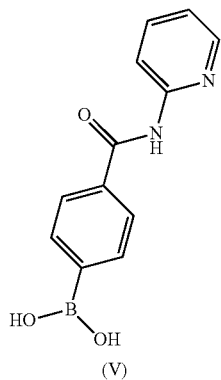

(V)

The clinical trial supply process reacts 4-carboxyphenylboronic acid with 2-aminopyridine to produce Compound (V). This coupling reaction is carried out in the presence of thionyl chloride and N,N-dimethylformamide. Thionyl chloride and N,N-dimethylformamide, however, potentially can react to produce toxic dimethylcarbamoyl chloride. To avoid this problem, the improved process replaces N,N-dimethylformamide with a compound (e.g., tetrabutylammonium chloride) that does not generate this toxic by-product and provides improved safety during this step.

Accordingly, in one embodiment, the present disclosure relates to a process for preparing a compound having the structure of Formula (V):

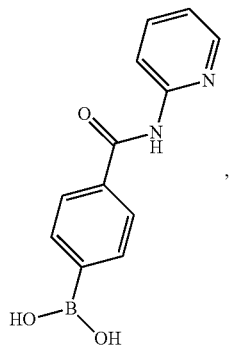

(V)

or a salt thereof, wherein the process comprises contacting 4-carboxyphenylboronic acid, or a salt thereof, with thionyl chloride and a catalyst in a reaction medium comprising an organic solvent to form an acyl chloride intermediate which is then contacted in situ with 2-aminopyridine to form a reaction mixture comprising the compound of Formula (V), or salt thereof. In one aspect, the process further comprises isolating the compound of Formula (V), or salt thereof, from the reaction mixture.

A molar excess of 2-aminopyridine generally is charged to the reaction medium relative to the 4-carboxyphenylboronic acid, or salt thereof. In one aspect, about 1.5 to about 5 molar equivalents of 2-aminopyridine are charged to the reaction medium relative to the 4-carboxyphenylboronic acid, or salt thereof. In another aspect, about 1.5 to about 3.5 molar equivalents of 2-aminopyridine are charged to the reaction medium relative to the 4-carboxyphenylboronic acid, or salt thereof. In another aspect, about 2 molar equivalents of 2-aminopyridine are charged to the reaction medium relative to the 4-carboxyphenylboronic acid, or salt thereof.

A molar excess of the thionyl chloride generally is charged to the reaction medium relative to the 4-carboxyphenylboronic acid, or salt thereof. In one aspect, 4-carboxyphenylboronic acid, or salt thereof, is contacted with about 2 to about 5 molar equivalents of thionyl chloride relative to the 4-carboxyphenylboronic acid, or salt thereof. In another aspect, 4-carboxyphenylboronic acid, or salt thereof, is contacted with about 2 to about 3.5 molar equivalents of thionyl chloride relative to the 4-carboxyphenylboronic acid, or salt thereof. In another aspect, 4-carboxyphenylboronic acid, or salt thereof, is contacted with about 2.75 molar equivalents of thionyl chloride relative to the 4-carboxyphenylboronic acid, or salt thereof.

The catalyst can comprise any suitable catalyst, particularly a catalyst selected from the group consisting of tetrabutylammonium chloride and N-methylformanilide. In one aspect, the catalyst comprises tetrabutylammonium chloride. In another aspect, the catalyst comprises N-methylformanilide. In another aspect, the catalyst does not comprise N,N-dimethylformamide. About 0.01 to about 0.1 molar equivalents of the catalyst generally are charged to the reaction medium relative to the 4-carboxyphenylboronic acid, or salt thereof.

The reaction medium can be any suitable reaction medium, particularly one comprising at least one solvent selected from the group consisting of aromatic hydrocarbons, aromatic heterocycles, and nitriles. In one aspect, the reaction medium comprises a compound selected from the group consisting of toluene, acetonitrile, and pyridine. In another aspect, the reaction medium comprises toluene. In another aspect, the reaction medium does not comprise N,N-dimethylformamide. In another aspect, neither the reaction medium nor the catalyst comprises N,N-dimethylformamide. The volume of reaction medium generally is about 3 liters to about 30 liters of reaction medium per kilogram of the 4-carboxyphenylboronic acid, or salt thereof, charged to the reaction medium. In one aspect, the volume of reaction medium is about 5 liters to about 15 liters of reaction medium per kilogram of the 4-carboxyphenylboronic acid, or salt thereof, charged to the reaction medium.

The reaction medium generally is maintained at a temperature from about 50° C. to about 90° C. during the contacting step. In one aspect, the reaction medium is maintained at a temperature from about 60° C. to about 80° C. during the contacting step.

The contacting step generally is carried out as a batch reaction, particularly one where at least about 50 kilograms of the 4-carboxyphenylboronic acid, or salt thereof, are charged to the batch reaction. In one aspect, at least about 100 kilograms of the 4-carboxyphenylboronic acid, or salt thereof, are charged to the batch reaction.

The process generally provides at least about a 50% stoichiometric process yield of the compound of Formula (V), or salt thereof. In one aspect, the stoichiometric process yield of the compound of Formula (V), or salt thereof, is at least about 60%. In another aspect, the stoichiometric process yield of the compound of Formula (V), or salt thereof, is at least about 65%. In another aspect, the stoichiometric process yield of the compound of Formula (V), or salt thereof, is at least about 70%.

In another representative embodiment, the present disclosure relates to a process for preparing a compound having the structure of Formula (V):

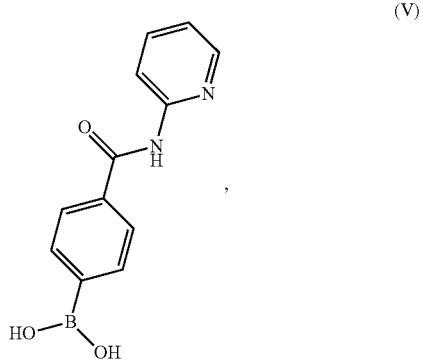 [SMILES: O=C(Nc1ccccn1)c1ccc(B(O)O)cc1]

(V)

or a salt thereof, wherein the process comprises contacting 4-carboxyphenylboronic acid, or a salt thereof, with thionyl chloride and a catalyst in a reaction medium comprising an organic solvent to form an acyl chloride intermediate which is then contacted in situ with 2-aminopyridine to form a reaction mixture comprising the compound of Formula (V), or salt thereof; wherein neither the reaction medium nor the catalyst comprises N,N-dimethylformamide.

In one aspect, the catalyst comprises a catalyst selected from the group consisting of tetrabutylammonium chloride and N-methylformanilide. In one aspect, the catalyst comprises tetrabutylammonium chloride. In another aspect, the catalyst comprises N-methylformanilide. In another aspect, the reaction medium is maintained at a temperature from about 50° C. to about 90° C. during the contacting step. In another aspect, the process further comprises isolating the compound of Formula (V), or salt thereof, from the reaction mixture.

Scheme 12 below corresponds to the process described in Example 11 and illustrates one representative embodiment of the improved process for preparing Compound (V).

SCHEME 12

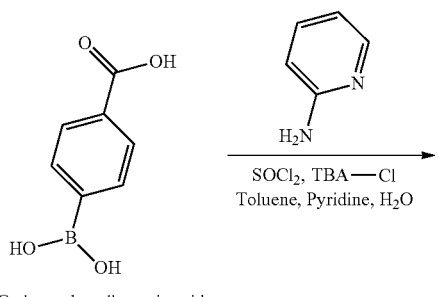

4-Carboxyphenylboronic acid

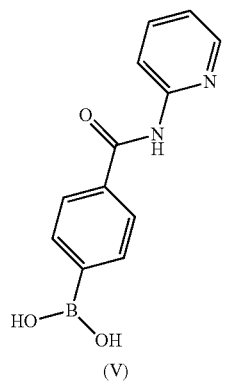

(V)

IX. PREPARATION of 1-Bromo-3-[(2S)-2-pyrrolidinyl]imidazo[1,5-a]pyrazin-8-amine (COMPOUND VI)

The present disclosure relates, in part, to processes for preparing 1-bromo-3-[(2S)-2-pyrrolidinyl]imidazo[1,5-a]pyrazin-8-amine (Compound VI), or a salt thereof, from benzyl (2S)-2-(8-amino-1-bromoimidazo[1,5-a]pyrazin-3-yl)-1-pyrrolidinecarboxylate (Compound IV), or a salt thereof. Scheme 13 below illustrates the general process:

SCHEME 13

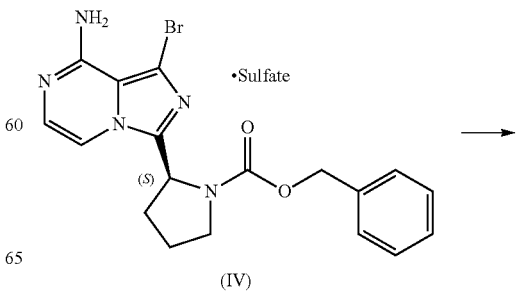

(IV)

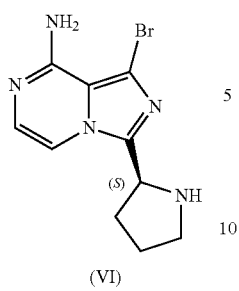

(VI)

Initial development efforts to avoid aggressive acidic conditions by employing hydrogenation to deprotect Compound (IV), or a salt thereof, and provide Compound (VI), or a salt thereof, were unsuccessful due to the presence of the labile bromide on the imidazole ring. Further development efforts encountered challenges involving the generation and/or removal of several impurities.

First, the deprotection reaction generates a benzyl halide (e.g., benzyl chloride) that potentially can react further with Compound (VI), or a salt thereof, to produce an N-benzyl impurity having the structure of Compound (IX):

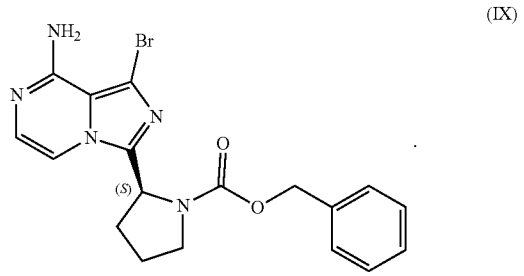

(IX)

Second, the use of dichloromethane in the deprotection reaction can generate an aminal impurity having the structure of Compound (X):

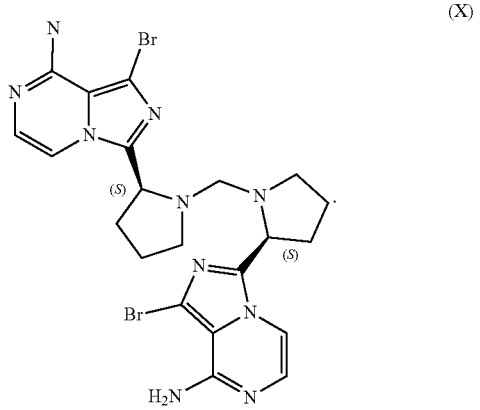

(X)

Third, an oxidation impurity having the structure of Compound (XI) below was observed in several batches for this process step:

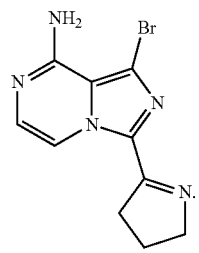

(XI)

The improved process addresses the N-benzyl impurity by removing the benzyl halide from the reaction mixture containing the crude Compound (VI) product (e.g., by extraction with heptane) prior to isolating Compound (VI), or salt thereof, from the reaction mixture. The improved process addresses the aminal impurity by selecting a solvent that does not generate an aminal impurity (e.g., replacing dichloromethane with 2-methyltetrahydrofuran). The improved process addresses the oxidation impurity through appropriate control of oxygen levels in the reaction vessel during the process. Proper control of the inerting regime (e.g., nitrogen sweep) and materials of vessel construction improve product quality by substantially preventing product discoloration and formation of the oxidation impurity observed in prior campaigns and eliminating the prior need for carbon treatment.

Accordingly, in one embodiment, the present disclosure relates to a process for preparing a compound having the structure of Formula (VI):

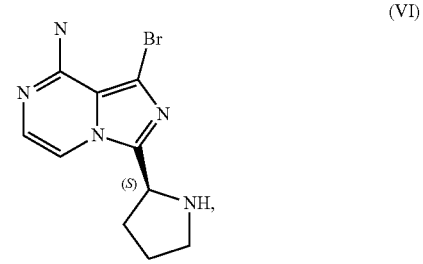

(VI)

or a salt thereof, wherein the process comprises:
contacting a compound of Formula (IV):

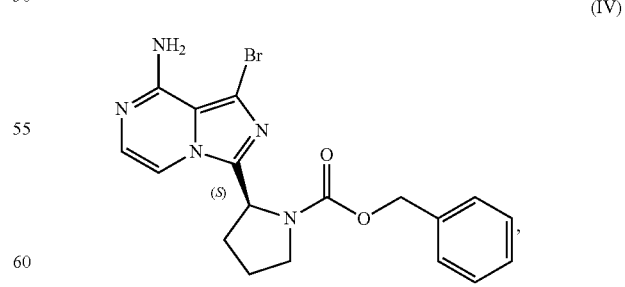

(IV)

or a salt thereof, with an acidic medium under conditions sufficient to deprotect the compound of Formula (IV), or salt thereof, and form a reaction mixture comprising the compound of Formula (VI), or a salt thereof, and a benzyl halide by-product;

removing at least a portion of the benzyl halide by-product from the reaction mixture; and isolating the compound of Formula (VI), or salt thereof, from the reaction mixture under conditions sufficient to substantially avoid the formation of an aminal impurity.

In one aspect, a sulfate salt of the compound of Formula (IV) is contacted with the acidic medium.

The aminal impurity generally comprises a compound having the structure of Formula (X):

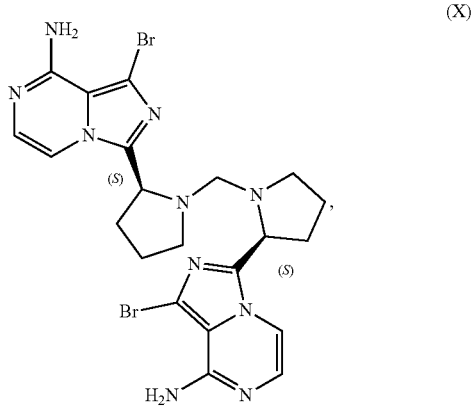

or a salt thereof. In one aspect, the isolated compound of Formula (VI), or salt thereof, comprises less than 5 weight % of the aminal impurity. In another aspect, the isolated compound of Formula (VI), or salt thereof, comprises less than 3 weight % of the aminal impurity. In another aspect, the isolated compound of Formula (VI), or salt thereof, comprises less than 1 weight % of the aminal impurity.

In one aspect, the acidic medium is an aqueous acidic medium. The aqueous acidic medium generally comprises a mineral acid, particularly hydrochloric acid, and at least about 10 molar equivalents of the acid relative to the compound of Formula (IV), or salt thereof. In one aspect, the aqueous acidic medium comprises from about 10 to about 40 molar equivalents of the acid relative to the compound of Formula (IV), or salt thereof. In another aspect, the aqueous acidic medium comprises from about 10 to about 25 molar equivalents of the acid relative to the compound of Formula (IV), or salt thereof. The volume of aqueous acidic medium generally is about 2 liters to about 10 liters of aqueous acidic medium per kilogram of the compound of Formula (IV), or salt thereof, charged to the acidic medium. In one aspect, the volume of aqueous acidic medium is about 3 liters to about 4 liters of aqueous acidic medium per kilogram of the compound of Formula (IV), or salt thereof, charged to the aqueous acidic medium. During the contacting step, the aqueous acidic medium generally is maintained at a temperature from about 25° C. to about 70° C. In one aspect, the aqueous acidic medium is maintained at a temperature from about 40° C. to about 50° C. during the contacting step.

In another embodiment, the process comprises removing at least a portion of the benzyl halide by-product from the reaction mixture; increasing the pH of the resulting reaction mixture to a basic pH to form a basic reaction medium comprising the compound of Formula (VI), or salt thereof; and isolating the compound of Formula (VI), or salt thereof, from the basic reaction mixture.

In another embodiment, the process comprises removing at least a portion of the benzyl halide by-product from the reaction mixture by selectively extracting the benzyl halide by-product from the reaction mixture prior to isolating the compound of Formula (VI), or salt thereof. In one aspect, the benzyl halide by-product from the reaction mixture is selectively extracted into a discard organic phase relative to the compound of Formula (VI), or salt thereof. In another aspect, at least about 80 weight % of the benzyl halide by-product present in the reaction mixture is extracted into the discard organic phase. In another aspect, less than about 20 weight % of the compound of Formula (VI), or salt thereof, present in the reaction mixture is extracted into the discard organic phase. In another aspect, at least about 80 weight % of the benzyl halide by-product present in the reaction mixture and less than about 20 weight % of the compound of Formula (VI), or salt thereof, present in the reaction mixture is extracted into the discard organic phase. In another aspect, at least about 90 weight % of the benzyl halide by-product present in the reaction mixture and less than about 10 weight % of the compound of Formula (VI), or salt thereof, present in the reaction mixture is extracted into the discard organic phase. In another aspect, at least about 95 weight % of the benzyl halide by-product present in the reaction mixture and less than about 5 weight % of the compound of Formula (VI), or salt thereof, present in the reaction mixture is extracted into the discard organic phase.

The discard organic phase generally comprises at least one solvent selected from the group consisting of alkyl hydrocarbons, aromatic hydrocarbons, chlorinated hydrocarbons, and ethers. In one aspect, the discard organic phase comprises at least one compound selected from the group consisting of pentane, hexane, heptane, octane, nonane, toluene, dichloromethane, methyl tert-butyl ether, and 2-methyltetrahydrofuran. In another aspect, the discard organic phase comprises heptane.

In further embodiments, the process comprises increasing the pH of the reaction mixture after the benzyl halide by-product extraction to form a basic reaction medium comprising the compound of Formula (VI), or salt thereof; and extracting the compound of Formula (VI), or salt thereof, from the basic reaction medium into a product organic phase. In one aspect, the process comprises extracting at least a portion of the benzyl halide by-product from the reaction mixture into a discard organic phase; increasing the pH of the resulting reaction mixture (e.g., through addition of sodium hydroxide) to a basic pH to form a basic reaction medium comprising the compound of Formula (VI), or salt thereof; extracting the compound of Formula (VI), or salt thereof, from the basic reaction medium into a product organic phase; and isolating the compound of Formula (VI), or salt thereof, from the product organic phase. The pH of the basic reaction mixture generally is increased to at least about 8.0. In one aspect, the pH of the basic reaction mixture is increased to at least about 10.0.

The product organic phase generally comprises at least one solvent selected from the group consisting of alkyl hydrocarbons, aromatic hydrocarbons, chlorinated hydrocarbons, and ethers. In one aspect, the product organic phase comprises at least one compound selected from the group consisting of 2-methyltetrahydrofuran and anisole. In another aspect, the product organic phase comprises 2-methyltetrahydrofuran. In another aspect, the product organic phase does not comprise dichloromethane.

It can be beneficial to wash the product organic phase (e.g., a water wash) before isolating the compound of Formula (VI), or salt thereof. It also can be beneficial to distill the product organic phase under conditions sufficient to reduce the amount of water present in the product organic phase before isolating the compound of Formula (VI), or salt thereof. In one aspect, the process comprises washing the product organic phase with water and distilling the product organic phase under conditions sufficient to reduce the amount of water present in the product organic phase. In another aspect, the product organic phase is distilled under atmospheric pressure. In another aspect, the product organic phase comprises 2-methyltetrahydrofuran and additional 2-methyltetrahydrofuran is charged to the product organic phase during the distilling step.

The compound of Formula (VI), or salt thereof, can be isolated from the reaction mixture by any suitable means, particularly crystallizing the compound of Formula (VI), or salt thereof, from the reaction mixture. In one aspect, the isolating step comprises seeding the reaction mixture with a crystalline form of the compound of Formula (VI), or salt thereof, to promote crystallization. In another aspect, the isolating step comprises seeding the reaction mixture with at least about 0.005 relative weight of the crystalline form of the compound of Formula (VI), or salt thereof, to promote crystallization. In another aspect, the isolating step comprises seeding the reaction mixture with at least about 0.01 relative weight of the crystalline form of the compound of Formula (VI), or salt thereof, to promote crystallization. In another aspect, the isolating step comprises seeding the reaction mixture with at least about 0.005 to about 0.02 relative weight of the crystalline form of the compound of Formula (VI), or salt thereof, to promote crystallization. It also can be beneficial to charge an anti-solvent to the reaction mixture to promote crystallization. In one aspect, the anti-solvent is heptane.

The contacting step generally is carried out as a batch reaction, particularly one where at least about 50 kilograms of the compound of Formula (IV), or salt thereof, are initially charged to the reaction. In one aspect, at least about 100 kilograms of the compound of Formula (IV), or salt thereof, are initially charged to the reaction. In another aspect, at least about 200 kilograms of the compound of Formula (IV), or salt thereof, are initially charged to the reaction. In another aspect, at least about 300 kilograms of the compound of Formula (IV), or salt thereof, are initially charged to the reaction.

The process generally provides at least about a 50% stoichiometric process yield of the compound of Formula (VI), or salt thereof. In one aspect, the stoichiometric process yield of the compound of Formula (VI), or salt thereof, is at least about 65%. In another aspect, the stoichiometric process yield of the compound of Formula (VI), or salt thereof, is at least about 75%. In another aspect, the stoichiometric process yield of the compound of Formula (VI), or salt thereof, is at least about 80%. In fact, the improved process has been able to deliver approximately 85% yield of good quality material at over 300 kg (input) scale.

In another representative embodiment, the present disclosure relates to a process for preparing a compound having the structure of Formula (VI):

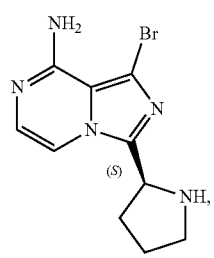

(VI)

or a salt thereof, wherein the process comprises:
contacting a compound of Formula (IV):

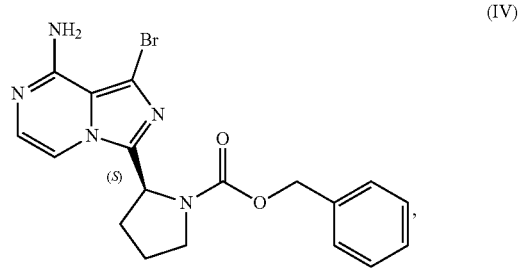

(IV)

or a salt thereof, with an acidic medium under conditions sufficient to deprotect the compound of Formula (IV), or salt thereof, and form a reaction mixture comprising the compound of Formula (VI), or a salt thereof, and a benzyl halide by-product;

selectively extracting at least a portion of the benzyl halide by-product from the reaction mixture into a discard organic phase relative to the compound of Formula (VI), or salt thereof;

increasing the pH of the resulting reaction mixture to a pH greater than about 7.0 to form a basic reaction mixture;

selectively extracting at least a portion of the compound of Formula (VI), or salt thereof, from the basic reaction mixture into a product organic phase; and distilling the product organic phase under conditions sufficient to reduce the amount of water present in the product organic phase to form a distilled organic phase comprising the compound of Formula (VI), or salt thereof.

In one aspect, the discard organic phase comprises heptane. In another aspect, the product organic phase comprises 2-methyltetrahydrofuran. In another aspect, the discard organic phase comprises heptane and the product organic phase comprises 2-methyltetrahydrofuran. In another aspect, the process further comprises crystallizing the compound of Formula (VI), or salt thereof, from the distilled organic phase.

Scheme 14 below corresponds to the process described in Example 9 and illustrates one representative embodiment of the improved process for preparing Compound (VI).

SCHEME 14

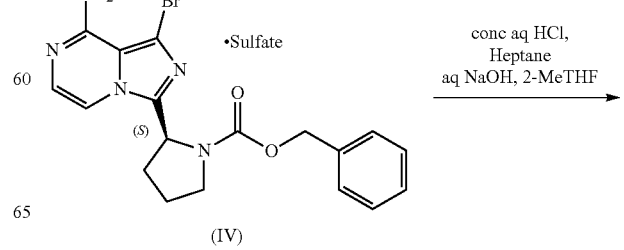

(IV)

-continued

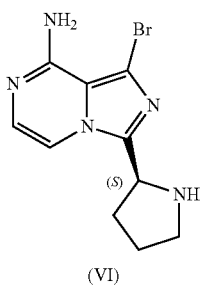

(VI)

X. PREPARATION of 4-{8-Amino-3-[(2S)-2-pyrrolidinyl]imidazo[1,5-a]pyrazin-1-yl}-N-(2-pyridinyl)benzamide (COMPOUND VII)

The present disclosure relates, in part, to processes for preparing 4-{8-amino-3-[(2S)-2-pyrrolidinyl]imidazo[1,5-a]pyrazin-1-yl}-N-(2-pyridinyl)benzamide (Compound VII), or a salt thereof, from [4-(2-pyridylcarbamoyl)phenyl]boronic acid (Compound V), or a salt thereof, and 1-bromo-3-[(2S)-2-pyrrolidinyl]imidazo[1,5-a]pyrazin-8-amine (Compound VI), or a salt thereof. Scheme 15 below illustrates the general process:

SCHEME 15

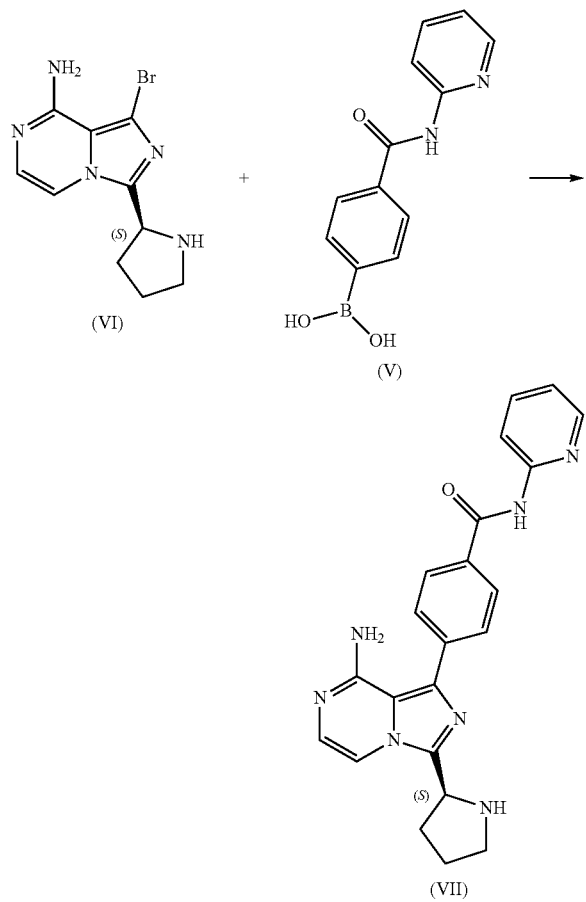

The process employs a Suzuki reaction to couple Compound (V) and Compound (VI) to produce Compound (VII).

The clinical trial supply process carried out the Suzuki coupling in an aqueous 2-butanol medium. The crude Compound (VII) was crystallized from the aqueous 2-butanol medium in a crystalline form (subsequently identified as the Type 2 crystalline form of Compound (VII)) that was extremely difficult to filter from the medium, even on a 50 kg scale. The Type 2 crystalline form of Compound (VII) was isolated as a thick, clay-like product which requiring oven drying to remove the large volume of water clinging to the wet paste on discharge from the filter.

Efforts to improve the filterability of the crystallized Compound (VII) resulted in the discovery of two additional crystalline forms of Compound (VII), designated as the Type 3 crystalline form and the Form C crystalline form. The Type 2 crystalline form has a very fine needle morphology and is believed to be a hemi-butanol solvate-hydrate. The Type 3 crystalline form has a needle morphology and is believed to be a butanol solvate. The Form C crystalline form is an anhydrate having an improved morphology that results in larger crystals. It was found that crystallization of Compound (VII) from a non-aqueous (generally less than 5 weight % water) medium can produce the Type 3 crystalline form and/or the Form C crystalline form. Both crystalline forms filter more quickly than the Type 2 crystalline form, but the Form C crystalline form also filters more quickly than the Type 3 crystalline form. Therefore, further efforts focused on reducing or substantially removing any water present (e.g., by distillation) prior to the initial isolation of Compound (VII) in order to reproducibly isolate Compound (VII) as the Form C crystalline form.

Although the removal of water prior to isolation of Compound (VII) routinely provided the Form C crystalline form, occasional batches still crystallized with variable amounts of the Type 3 crystalline form present. Further investigation determined that the Form C crystalline form is the thermodynamic form at temperatures above approximately 75° C. At this temperature any Type 3 crystalline form present generally converts to the Form C crystalline form within a relatively short period of time. By incorporating a temperature cycle prior to isolation of Compound (VII), the Form C crystalline form can be routinely produced as the thermodynamic form. Although conversion from the Form C crystalline form back to the Type 3 crystalline form can take place on cooling below 75° C. (particularly in the presence of residual water), this conversion is sufficiently slow allowing cool down and filtration to take place without significant conversion back to the Type 3 crystalline form.

Additionally, shifting the silica scavenger treatment from the final step for producing acalabrutinib from Compound (VII) (as was employed in the clinical trial supply process) to the present step for producing Compound (VII) was found to be advantageous. This change in the sequencing of the silica scavenger treatment provides a better balance of efficient palladium removal versus loss of product yield (to the scavenger).

Further, it was found that prolonged heating on scale for this process (e.g., work-up at 80° C. and atmospheric distillation at 80° C. to 100° C.) during the Suzuki reaction resulted in formation of two impurities, Compound (XII) and Compound (XIII) having the structures shown below:

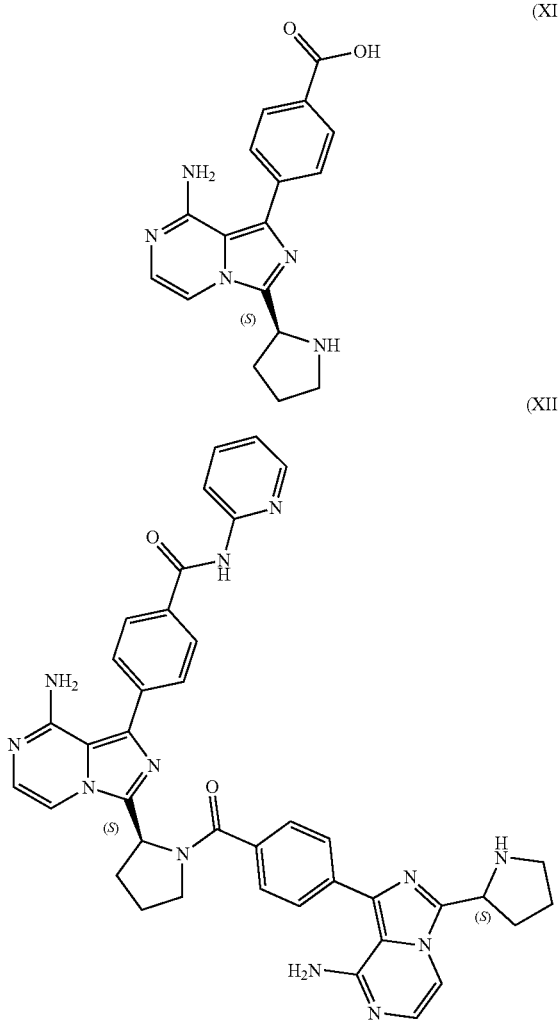

(XII)

(XIII)

By employing a lower temperature (e.g., work-up and atmospheric distillation below 60° C.), however, formation of these impurities can be suppressed.

Accordingly, in one embodiment, the present disclosure relates to a process for preparing a compound having the structure of Formula (VII):

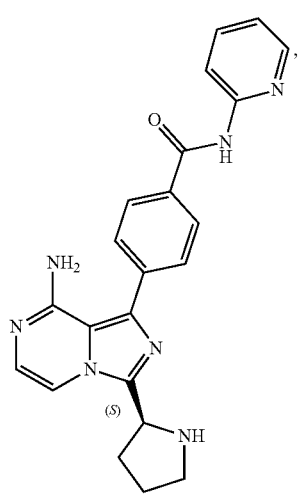

(VII)

or a salt thereof, wherein the process comprises:
contacting a compound having the structure of Formula (V):

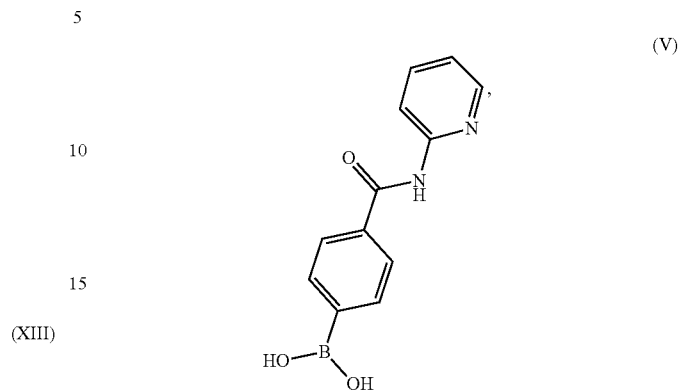

(V)

or a salt thereof, with a compound having the structure of Formula (VI):

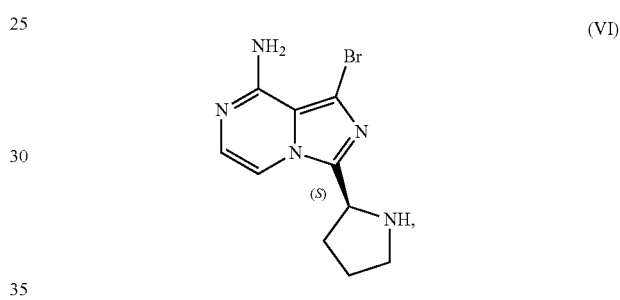

(VI)

or a salt thereof, in the presence of a base and a palladium catalyst in an aqueous reaction medium comprising an organic solvent to form a reaction mixture comprising the compound of Formula (VII);
decreasing the amount of water present in the reaction mixture to form a substantially anhydrous mixture comprising the compound of Formula (VII), or salt thereof; and
isolating the compound of Formula (VII), or salt thereof, from the substantially anhydrous mixture.

The compound of Formula (VII), or salt thereof, is isolated from the substantially anhydrous mixture as a substantially crystalline form of the compound of Formula (VII), or salt thereof. In one aspect, the substantially crystalline form of the compound of Formula (VII) is characterized by a reflection X-ray powder diffraction pattern comprising at least three peaks selected from the group consisting of 9.9±0.2 °2θ, 11.1±0.2 °2θ, 12.8±0.2 °2θ, 14.1±0.2 °2θ, and 19.0±0.2 °2θ. In another aspect, the substantially crystalline form of the compound of Formula (VII) is characterized by a reflection X-ray powder diffraction pattern comprising at least three peaks selected from the group consisting of 7.4±0.2 °2θ, 8.9±0.2 °2θ, 9.9±0.2 °2θ, 11.1±0.2 °2θ, 12.8±0.2 °2θ, 14.1±0.2 °2θ, 14.8±0.2 °2θ, 19.0±0.2 °2θ, and 21.6±0.2 °2θ. In another aspect, the substantially crystalline form of the compound of Formula (VII) is characterized by a reflection X-ray powder diffraction pattern comprising at least five peaks selected from the group of peaks. In another aspect, the substantially crystalline form is a substantially anhydrous crystalline form of the compound of Formula (VII).

The substantially crystalline form of the compound of Formula (VII) isolated from the substantially anhydrous mixture generally has a Form C crystalline purity of at least 50%. In one aspect, the isolated substantially crystalline form has a Form C crystalline purity of at least 60%. In another aspect, the isolated substantially crystalline form has a Form C crystalline purity of at least 70%. In another aspect, the isolated substantially crystalline form has a Form C crystalline purity of at least 80%. In another aspect, the isolated substantially crystalline form has a Form C crystalline purity of at least 90%. In another aspect, the isolated substantially crystalline form has a Form C crystalline purity of at least 95%. In another aspect, the isolated substantially crystalline form has a Form C crystalline purity of at least 96%. In another aspect, the isolated substantially crystalline form has a Form C crystalline purity of at least 97%. In another aspect, the isolated substantially crystalline form has a Form C crystalline purity of at least 98%. In another aspect, the isolated substantially crystalline form has a Form C crystalline purity of at least 99%. In another aspect, the isolated substantially crystalline form is substantially phase pure Form C crystalline form.

In another embodiment, the aqueous reaction medium further comprises an alkali metal halide. In one aspect, the aqueous reaction medium comprises an alkali metal iodide. In another aspect, the aqueous reaction medium comprises potassium iodide. At least about 0.1 molar equivalents of the alkali metal halide generally are charged to the aqueous reaction medium relative to the compound of Formula (VI), or salt thereof. In one aspect, about 0.1 to about 1.0 molar equivalents of the alkali metal halide generally are charged to the aqueous reaction medium relative to the compound of Formula (VI), or salt thereof. In one aspect, about 0.1 to about 1.0 molar equivalents of potassium iodide are charged to the aqueous reaction medium relative to the compound of Formula (VI), or salt thereof. In another aspect, about 0.2 to about 0.4 molar equivalents of potassium iodide are charged to the aqueous reaction medium relative to the compound of Formula (VI), or salt thereof.

The compound of Formula (VI), or salt thereof, generally is contacted with about 0.5 to about 1.5 molar equivalents of the compound of Formula (V), or salt thereof, relative to the compound of Formula (VI), or salt thereof. In one aspect, the compound of Formula (VI), or salt thereof, is contacted with about 0.8 to about 1.2 molar equivalents of the compound of Formula (V), or salt thereof, relative to the compound of Formula (VI), or salt thereof. In another aspect, the compound of Formula (VI), or salt thereof, is contacted with about 0.9 to about 1.1 molar equivalents of the compound of Formula (V), or salt thereof, relative to the compound of Formula (VI), or salt thereof.

The base can be any suitable base, particularly a base comprising at least one compound selected from the group consisting of triethylamine, potassium carbonate, potassium bicarbonate, sodium carbonate, sodium bicarbonate, cesium carbonate, tripropylamine, tributylamine, diiso-propylethylamine, N-methylmorpholine, N-methylpyrrolidine, methyldicyclohexylamine, and potassium phosphate. In one aspect, the base comprises triethylamine. In another aspect, the base comprises potassium carbonate. In another aspect, the base comprises triethylamine and potassium carbonate. About 0.5 to about 10 molar equivalents of the base generally are charged to the aqueous reaction medium relative to the compound of Formula (VI), or salt thereof. In one aspect, the base comprises triethylamine and about 0.5 to about 10 molar equivalents of triethylamine are charged to the aqueous reaction medium relative to the compound of Formula (VI), or salt thereof. In another aspect, the base comprises triethylamine and about 1.0 to about 2.0 molar equivalents of triethylamine are charged to the aqueous reaction medium relative to the compound of Formula (VI), or salt thereof. In another aspect, the base comprises potassium carbonate and about 0.5 to about 10.0 molar equivalents of potassium carbonate are charged to the aqueous reaction medium relative to the compound of Formula (VI), or salt thereof. In another aspect, the base comprises potassium carbonate and about 2.0 to about 3.0 molar equivalents of potassium carbonate are charged to the aqueous reaction medium relative to the compound of Formula (VI), or salt thereof. In another aspect, the base comprises potassium carbonate and about 2.3 to about 2.7 molar equivalents of potassium carbonate are charged to the aqueous reaction medium relative to the compound of Formula (VI), or salt thereof.

The palladium catalyst can be any suitable palladium catalyst, particularly one comprising bis(tert-butyldicyclohexylphosphine)dichloropalladium(II). About 0.002 to about 0.05 molar equivalents of the palladium catalyst generally are charged to the aqueous reaction medium relative to the compound of Formula (VI), or salt thereof. In one aspect, about 0.007 to about 0.013 molar equivalents of the palladium catalyst are charged to the aqueous reaction medium relative to the compound of Formula (VI), or salt thereof.

The organic solvent can be any suitable organic solvent, particularly one selected from the group consisting of aromatic hydrocarbons, alcohols, ketones, ethers, esters, and nitriles. In one aspect, the organic solvent comprises at least one solvent selected from the group consisting of methanol, ethanol, propanol, butanol, pentanol, dioxane, toluene, acetone, methyl ethyl ketone, methyl isobutyl ketone, tetrahydrofuran, 2-methyltetrahydrofuran, acetonitrile, ethyl acetate, isopropyl acetate, n-butyl acetate, and ethyl lactate. In another aspect, the organic solvent comprises 2-butanol.

The volume of aqueous reaction medium generally is about 10 liters to about 20 liters of aqueous reaction medium per kilogram of the compound of Formula (VI), or salt thereof, charged to the aqueous reaction medium. In one aspect, the volume ratio of water to organic solvent for the aqueous reaction medium is about 1:3 to about 3:1. During the contacting step, the aqueous reaction medium generally is maintained at a temperature from about 50° C. to about 100° C. In one aspect, the aqueous reaction medium is maintained at a temperature from about 70° C. to about 90° C. during the contacting step.

In one embodiment, the decreasing step comprises separating the reaction mixture into an aqueous discard phase and an organic phase comprising the compound of Formula (VII). In one aspect, the decreasing step further comprises distilling the organic phase under conditions sufficient to decrease the amount of water present in the organic phase and provide the substantially anhydrous mixture. In another aspect, the process further comprises washing the organic phase with water prior to distillation.

In further embodiments, the organic phase is treated with a silica scavenger prior to distillation. In one aspect, the organic phase is treated with a silica scavenger prior to distillation for a period of at least two hours. The silica scavenger generally comprises a propane thiol functionalized silica. In one aspect, the silica scavenger comprises QuadraSil™ MP. The process may further comprise removing the silica scavenger from the organic phase prior to distillation. In one aspect, the silica scavenger is removed from the organic phase by filtration prior to distillation. In another aspect, the process further comprises washing the organic phase with an aqueous brine solution after removing the catalyst and prior to distillation.

In another embodiment, the decreasing step comprises separating the reaction mixture into an aqueous discard phase and an organic phase comprising the compound of Formula (VII), or salt thereof; washing the organic phase with water; treating the organic phase with a silica scavenger; removing the silica scavenger from the organic phase; washing the organic phase with an aqueous brine solution; and distilling the organic phase under conditions sufficient to decrease the amount of water present in the organic phase.

Distillation of the organic phase can be conducted under suitable conditions, particularly distillation of the organic phase by vacuum distillation. In one aspect, the organic phase is distilled by continuous level vacuum distillation. In another aspect, the organic phase is distilled at a temperature not exceeding about 60° C. In another aspect, the organic phase is distilled at a temperature from about 50° C. to about 60° C. In another aspect, the organic phase comprises an alcohol. In another aspect, the organic phase is supplemented with alcohol to during the distilling step. In another aspect, the organic phase comprises 2-butanol. In another aspect, the organic phase is supplemented with 2-butanol during the distilling step.

The substantially anhydrous mixture generally comprises less than about 5 weight % water. In one aspect, the substantially anhydrous mixture comprises less than about 3 weight % water. In another aspect, the substantially anhydrous mixture comprises less than about 1 weight % water.

The isolating step generally comprises crystallizing the compound of Formula (VII) from the substantially anhydrous mixture as the Form C crystalline form. To ensure the product crystallizes as the Form C crystalline form, the substantially anhydrous mixture is heated to a temperature of at least about 70° C. (e.g., at least about 75° C.) and then cooled to crystallize the compound of Formula (VII). The period of time the substantially anhydrous mixture is maintained at a temperature (or range of temperatures) of at least about 70° C. before cooling begins will depend on the temperature (or range of temperatures) selected. At a higher temperature, a shorter holding period is generally needed to convert any non-Form C crystalline form present to the Form C crystalline form. The temperature selected, however, should not result in degradation of the compound of Formula (VII) or exceed the boiling point of the substantially anhydrous mixture. Additionally, stirring the substantially anhydrous mixture during the holding period and/or seeding the substantially anhydrous mixture with the Form C crystalline form may be beneficial in further reducing the duration of any required holding period. In various embodiments, therefore, the substantially anhydrous mixture is maintained at a selected temperature (or range of temperatures) for a period of time after crystallization initiates and before cooling begins, wherein the temperature (or range of temperatures) and period of time selected are sufficient to yield substantially the Form C crystalline form of the compound of Formula (VII) upon cooling of the substantially anhydrous mixture.

In one aspect, the substantially anhydrous mixture is heated to a temperature of at least about 80° C. In another aspect, the temperature is at least about 85° C. In another aspect, the temperature is at least about 90° C. In another aspect, the temperature is at least about 95° C. In another aspect, the temperature is from about 70° C. to about 105° C. In another aspect, the temperature is from about 75° C. to about 105° C. In another aspect, the temperature is from about 80° C. to about 105° C. In another aspect, the temperature is from about 85° C. to about 105° C. In another aspect, the temperature is from about 90° C. to about 105° C.

In one aspect, the temperature selected is sufficiently high such that no further holding period is required before cooling can begin. In another aspect, the holding period before cooling is at least about 15 minutes. In another aspect, the holding period before cooling is at least about 30 minutes. In another aspect, the holding period before cooling is at least about 1 hour. In another aspect, the holding period before cooling is at least about 1.5 hours. In another aspect, the holding period before cooling is at least about 2 hours.

In a one aspect, the temperature is at least about 75° C. and the holding period before cooling is at least about two hours. In another aspect, the temperature is at least about 80° C. and the holding period is at least about 1.5 hour. In another aspect, the temperature is at least about 85° C. and the holding period is at least about 1 hour. In another aspect, the temperature is at least about 90° C. and the holding period is at least about 15 minutes. In another aspect, the temperature is at least about 90° C. and no holding period is required. In another aspect, the temperature is from about 75° C. to about 105° C. and the holding period is from about 15 minutes to about 3 hours. In another aspect, the temperature is from about 80° C. to about 105° C. and the holding period is from about 15 minutes to about 3 hours. In another aspect, the temperature is from about 85° C. to about 105° C. and the holding period is from about 15 minutes to about 3 hours. In another aspect, the temperature is from about 90° C. to about 105° C. and the holding period is from about 5 minutes to about 2 hours. In another aspect, the temperature is from about 90° C. to about 105° C. and no further holding period is required before cooling.

In each of the above aspects, the substantially anhydrous mixture can be seeded with the Form C crystalline form of the compound of Formula (VII) to further facilitate crystallization of the desired crystalline form. For example, the substantially anhydrous mixture can be seeded with the Form C crystalline form, maintained at a temperature from about 85° C. to about 105° C. for a holding period from about 5 minutes to about 3 hours, and then cooled to crystallize the compound of Formula (VII).

The contacting step generally is carried out as a batch reaction, particularly one where at least about 25 kilograms of the compound of Formula (VI), or salt thereof, are initially charged to the reaction. In one aspect, at least about 50 kilograms of the compound of Formula (VI), or salt thereof, are initially charged to the reaction. In another aspect, at least about 75 kilograms of the compound of Formula (VI), or salt thereof, are initially charged to the reaction. In another aspect, at least about 100 kilograms of the compound of Formula (VI), or salt thereof, are initially charged to the reaction.

The process generally provides at least about a 50% stoichiometric process yield of the compound of Formula (VII), or salt thereof. In one aspect, the stoichiometric process yield of the compound of Formula (VII), or salt thereof, is at least about 65%. In another aspect, the stoichiometric process yield of the compound of Formula (VII), or salt thereof, is at least about 75%. In fact, the improved process has been able to deliver approximately 80% yield of good quality material at over 100 kg (input) scale. Further, the improved process has a faster filtration time which significantly reduces the cycle time for this process to less than one week.

In another representative embodiment, the present disclosure relates to a process for preparing a compound having the structure of Formula (VII):

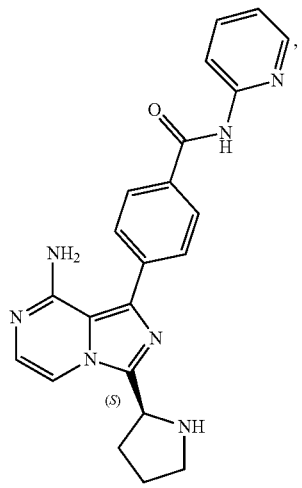

(VII)

or a salt thereof, wherein the process comprises:

contacting a compound having the structure of Formula (V):

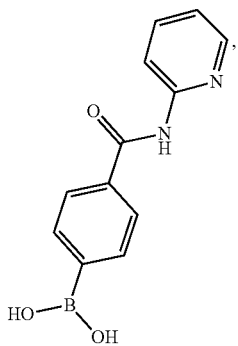

(V)

or a salt thereof, with a compound having the structure of Formula (VI):

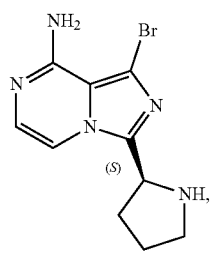

(VI)

or a salt thereof, in the presence of a base and a palladium catalyst in an aqueous reaction medium comprising an organic solvent to form a reaction mixture comprising the compound of Formula (VII);

separating the reaction mixture into an aqueous discard phase and an organic phase comprising the compound of Formula (VII), or salt thereof;

treating the organic phase with a silica scavenger;

removing the silica scavenger from the organic phase;

distilling the organic phase under conditions sufficient to decrease the amount of water present in the organic phase and form a substantially anhydrous mixture comprising the compound of Formula (VII), or salt thereof; and crystallizing the compound of Formula (VII) from the substantially anhydrous mixture;

wherein the compound of Formula (VII) crystallizes as Form C crystalline form.

In one aspect, the process further comprises washing the organic phase with water prior to the treating step. In another aspect, the process further comprises washing the organic phase with an aqueous brine solution after the removing step and prior to the distilling step. In another aspect, the organic phase is distilled by vacuum distillation during which dry butanol is added to the organic phase and functions to remove the water present. In another aspect, the substantially anhydrous mixture is held at a temperature above 75° C. until any crystalline form present is substantially converted to the Form C crystalline form before isolating the compound of Formula (VII) from the substantially anhydrous mixture.

Scheme 16 below corresponds to the process described in Example 14 and illustrates one representative embodiment of the improved process for preparing Compound (VII).

SCHEME 16

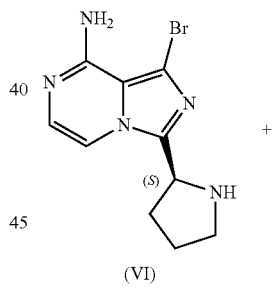

(VI)

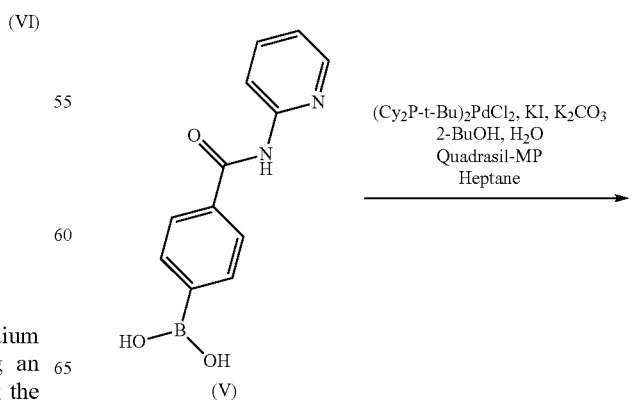

(V)

61

-continued

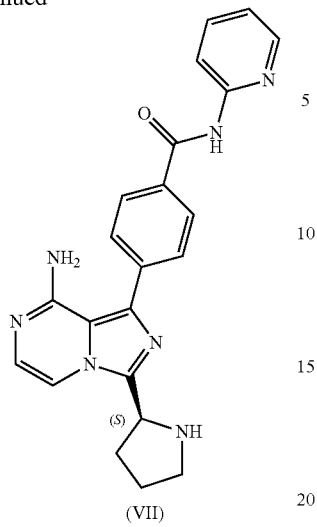

(VII)

XII. PREPARATION OF ACALABRUTINIB (COMPOUND VIII)

The present disclosure relates, in part, to processes for preparing acalabrutinib, or a salt thereof, from 4-{8-amino-3-[(2S)-2-pyrrolidinyl]imidazo[1,5-a]pyrazin-1-yl}-N-(2-pyridinyl)-benzamide (Compound VII), and 2-butynoic acid, or a salt thereof. Scheme 17 below illustrates the general process:

SCHEME 17

62

-continued

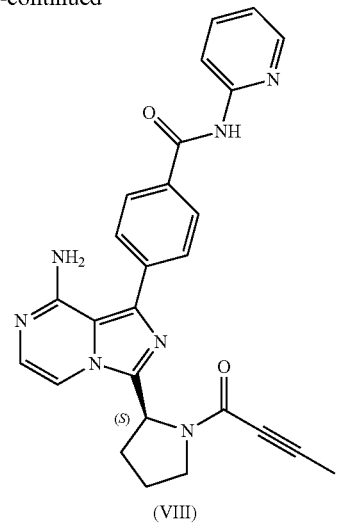

(VIII)

Compound (VII) is reacted with 2-butynoic acid in the presence of a coupling agent to produce acalabrutinib. This coupling step was difficult to operate in the clinical trial supply process. Addition of a small excess of 2-butynoic acid to Compound (VII) in dichloromethane generated a relatively thick mixture comprising the tetrolate salt of Compound (VII) that was difficult to stir. The subsequent addition of triethylamine to the thick mixture did not significantly improve viscosity. Addition of the triethylamine prior to the 2-butynoic acid, however, avoided the formation of the tetrolate salt of Compound (VII) and resulted in a relatively thin, stirrable slurry. The subsequent addition of the coupling agent (e.g., 1-propylphosphonic acid anhydride) to the resulting slurry, however, was difficult to control and had a narrow in-process control window in order to satisfy quality criteria for the acalabrutinib product. Under-addition of 1-propylphosphonic acid anhydride did not consume all of the starting material (i.e., Compound (VII)) and over-addition resulted in the formation of an impurity having the structure of Compound (XIV):

(XIV)

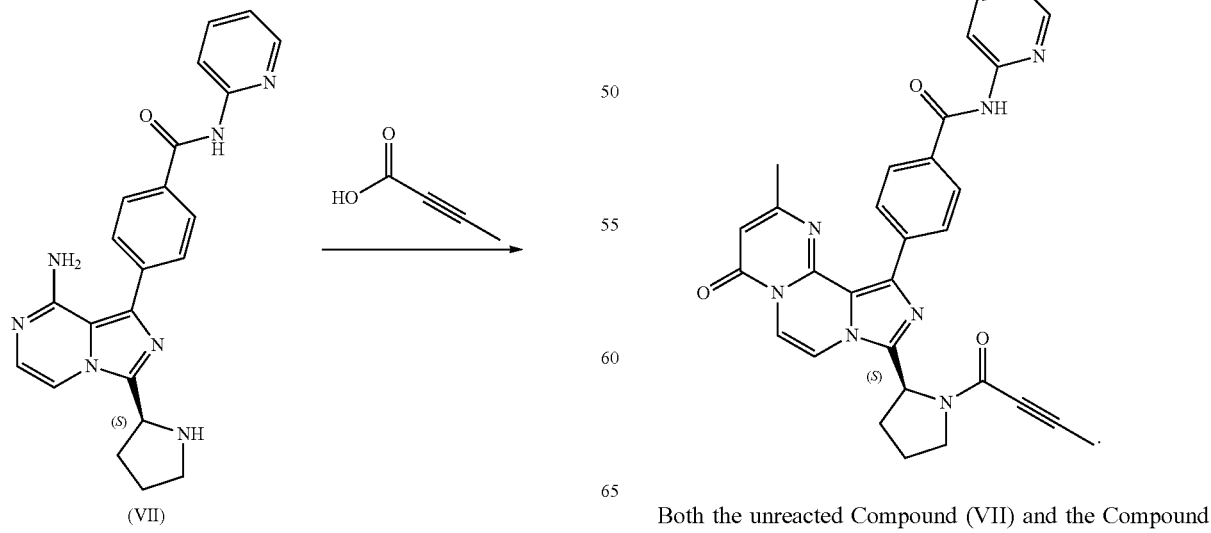

Both the unreacted Compound (VII) and the Compound (XIV) impurity were difficult to remove in the subsequent isolation of the acalabrutinib product and were responsible for several batch failures for the clinical trial supply process.

It was found that the difficulty associated with removal of the two impurities could be overcome using a sequential extraction approach. Acalabrutinib initially is selectively extracted relative to the Compound (XIV) impurity from the reaction mixture into an aqueous phase having a first acidic pH (e.g., pH 1.8 to 2.2) and the reaction mixture containing the Compound (XIV) impurity is discarded. The pH of the aqueous phase comprising acalabrutinib is then adjusted to a second pH (e.g., pH 4.5 to 5.0) and acalabrutinib is selectively extracted relative to the Compound (VII) impurity from the aqueous phase into an organic phase and the aqueous phase containing the Compound (VII) impurity is discarded. Because the sequential extraction approach results in the effective removal of the undesired impurities from the final product, the 1-propylphosphonic acid anhydride addition does not require the same rigid control as in the clinical trial supply process and the 1-propylphosphonic acid anhydride addition is more robust.

Another problem encountered with the clinical trial supply process involved the solvent exchange from dichloromethane to ethanol which employed multiple 'put-and-take' distillation cycles. The acalabrutinib product consistently oiled or gummed before eventually crystallizing. It was found that the kinetics of the crystallization of acalabrutinib from ethanol were unusually slow. The point at which the oil crystallized could not be controlled and the crystallized acalabrutinib entrained undesirable amounts of the crystallization solvent. As a result, inclusion of dichloromethane in the acalabrutinib crystal lattice was a concern for the clinical trial supply process. A more controlled procedure has now been developed which employs a continuous level vacuum distillation (e.g., 18 to 20 rel. vol. at 50° C.) that maintains acalabrutinib in solution throughout the distillation (even on complete replacement of the dichloromethane solvent by ethanol) and avoids the oiling problem. Once distillation is complete, seeding with crystalline acalabrutinib and holding the seeded solution at a suitable temperature (e.g., 50° C.) results in a controlled crystallization where the acalabrutinib product can be isolated with consistent particle properties. The crystallization further purifies the acalabrutinib product, particularly with respect to any over-acylated by-product present.

Accordingly, in one embodiment, the present disclosure relates to a process for preparing a compound having the structure of Formula (VIII):

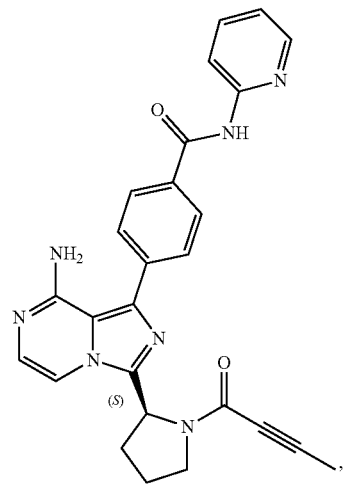

or a salt thereof, wherein the process comprises:
contacting a compound having the structure of Formula (VII):

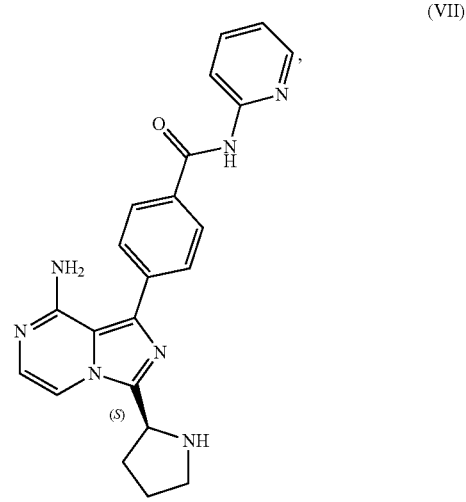

or a salt thereof, with 2-butynoic acid, or a salt thereof, in the presence of 1-propylphosphonic anhydride and a base in a reaction medium to form a reaction mixture comprising the compound of Formula (VIII) and one or more reaction by-products; and
selectively isolating the compound of Formula (VIII), or salt thereof, from the reaction mixture relative to the one or more by-products.

As previously noted, the order of addition for the process can have an impact. In general, the contacting step comprises adding the compound of Formula (VII), or salt thereof, and the base to the reaction medium; adding the 2-butynoic acid, or salt thereof, to the reaction medium comprising the compound of Formula (VII), or salt thereof, and the base; and adding the 1-propylphosphonic anhydride to the reaction medium comprising the compound of Formula (VII), or salt thereof; 2-butynoic acid, or salt thereof; and the base.

In another embodiment, the present disclosure relates to a process for preparing a compound having the structure of Formula (VIII):

(VIII)

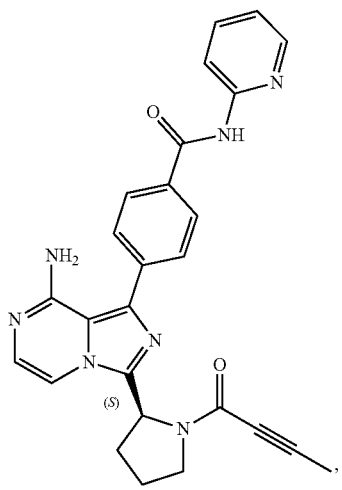

or a salt thereof, wherein the process comprises:

contacting a compound having the structure of Formula (VII):

(VII)

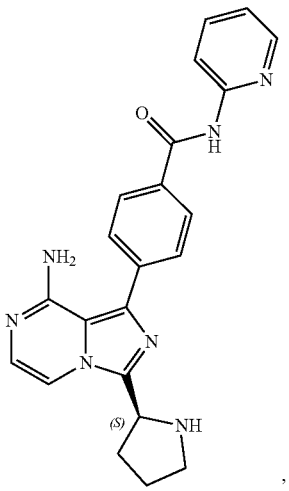

or a salt thereof, with 2-butynoic acid, or a salt thereof, in the presence of 1-propylphosphonic anhydride and a base in a reaction medium to form a reaction mixture comprising the compound of Formula (VIII), or salt thereof; unreacted compound of Formula (VII), or salt thereof; and a reaction by-product; wherein the reaction by-product comprises a compound having the structure of Formula (XIV):

(XIV)

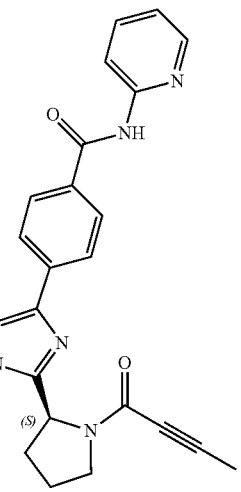

or a salt thereof; and selectively isolating the compound of Formula (VIII), or salt thereof, from the reaction mixture relative to the compound of Formula (VII), or salt thereof, and the compound of Formula (XIV), or salt thereof.

In one aspect, the selectively isolated compound of Formula (VIII), or salt thereof, comprises less than about 1.0 weight % of the compound of Formula (VII), or salt thereof. In another aspect, the selectively isolated compound of Formula (VIII), or salt thereof, comprises less than about 0.8 weight % of the compound of Formula (VII), or salt thereof. In another aspect, the selectively isolated compound of Formula (VIII), or salt thereof, comprises less than about 0.6 weight % of the compound of Formula (VII), or salt thereof. In another aspect, the selectively isolated compound of Formula (VIII), or salt thereof, comprises less than about 0.4 weight % of the compound of Formula (VII), or salt thereof. In another aspect, the selectively isolated compound of Formula (VIII), or salt thereof, comprises about less than about 0.3 weight % of the compound of Formula (VII), or salt thereof. In another aspect, the selectively isolated compound of Formula (VIII), or salt thereof, comprises less than about 1.0 weight % of the compound of Formula (XIV), or salt thereof. In another aspect, the selectively isolated compound of Formula (VIII), or salt thereof, comprises less than about 0.8 weight % of the compound of Formula (XIV), or salt thereof. In another aspect, the selectively isolated compound of Formula (VIII), or salt thereof, comprises less than about 0.6 weight % of the compound of Formula (XIV), or salt thereof. In another aspect, the selectively isolated compound of Formula (VIII), or salt thereof, comprises less than about 0.4 weight % of the compound of Formula (XIV), or salt thereof. In another aspect, the selectively isolated compound of Formula (VIII), or salt thereof, comprises less than about 0.3 weight % of the compound of Formula (XIV), or salt thereof. In another aspect, the selectively isolated compound of Formula (VIII), or salt thereof, comprises less than about 1.0 weight % of the compound of Formula (VII), or salt thereof, and less than about 1.0 weight % of the compound of Formula (XIV), or salt thereof. In another aspect, the selectively isolated compound of Formula (VIII), or salt thereof, comprises less than about 0.8 weight % of the compound of Formula (VII), or salt thereof, and less than about 0.8 weight % of the compound of Formula (XIV), or salt thereof. In another aspect, the selectively isolated compound of Formula (VIII), or salt thereof, comprises less than about 0.6 weight % of the compound of Formula (VII), or salt thereof, and less than about 0.6 weight % of the compound of Formula (XIV), or salt thereof. In another aspect, the selectively isolated compound of Formula (VIII), or salt thereof, comprises less than about 0.4 weight % of the compound of Formula (VII), or salt thereof, and less than about 0.4 weight % of the compound of Formula (XIV), or salt thereof. In another aspect, the selectively isolated compound of Formula (VIII), or salt thereof, comprises less than about 0.3 weight % of the compound of Formula (VII), or salt thereof, and less than about 0.3 weight % of the compound of Formula (XIV), or salt thereof.

In another embodiment, the present disclosure relates to a process for preparing a compound having the structure of Formula (VIII):

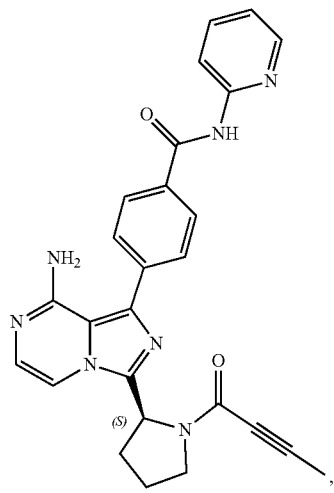

(VIII)

or a salt thereof, wherein the process comprises:
contacting a compound having the structure of Formula (VII):

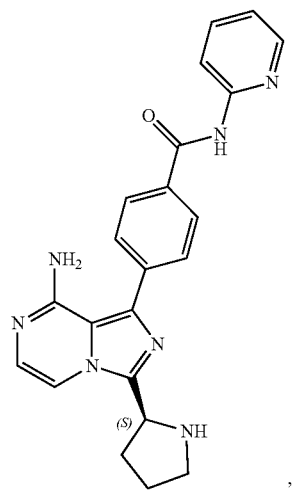

(VII)

or a salt thereof, with 2-butynoic acid, or a salt thereof, in the presence of 1-propylphosphonic anhydride and a base in a reaction medium to form a reaction mixture comprising the compound of Formula (VIII), or salt thereof; unreacted compound of Formula (VII), or salt thereof; and a reaction by-product, wherein the reaction by-product comprises a compound having the structure of Formula (XIV):

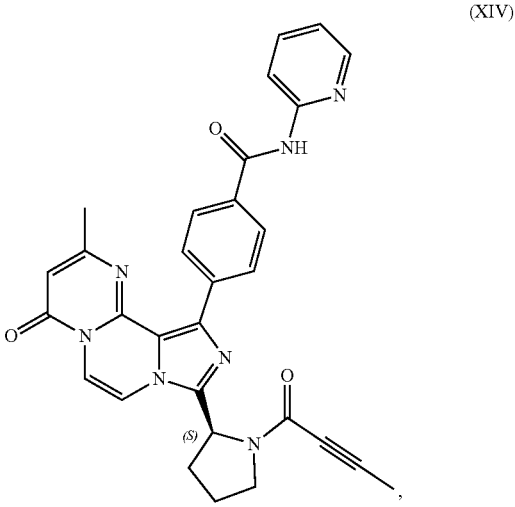

(XIV)

or a salt thereof;
extracting at least a portion of the compound of Formula (VIII), or salt thereof, from the reaction mixture into an aqueous phase, wherein the compound of Formula (VIII), or salt thereof, is selectively extracted into the aqueous phase relative to the compound of Formula (XIV), or salt thereof;
adjusting the pH of the aqueous phase; and
extracting at least a portion of the compound of Formula (VIII), of salt thereof, from the aqueous phase into an organic phase, wherein the compound of Formula (VIII), or salt thereof, is selectively extracted into the organic phase relative to the compound of Formula (VII), or salt thereof.

In one aspect, the contacting step comprises adding the compound of Formula (VII) and the base to the reaction medium; adding the 2-butynoic acid to the reaction medium comprising the compound of Formula (VII) and the base; and adding the 1-propylphosphonic anhydride to the reaction medium comprising the compound of Formula (VII), 2-butynoic acid, and the base. In another aspect, the reaction mixture is washed with water and the washed reaction mixture is separated into the aqueous phase and a discard phase, wherein the compound of Formula (VIII) is selectively extracted into the aqueous phase. In another aspect, the process further comprises isolating the compound of Formula (VIII) from the organic phase into which the compound of Formula (VIII) has been selectively extracted.

The compound of Formula (VII) generally is contacted with at least about 0.5 molar equivalents of 2-butynoic acid relative to the compound of Formula (VII). In one aspect, the compound of Formula (VII) is contacted with about 0.5 to about 5.0 molar equivalents of 2-butynoic acid relative to the compound of Formula (VII). In another aspect, the compound of Formula (VII) is contacted with about 1.0 to about 1.3 molar equivalents of 2-butynoic acid relative to the compound of Formula (VII). In another aspect, the compound of Formula (VII) is contacted with about 1.2 molar equivalents of 2-butynoic acid relative to the compound of Formula (VII).

Generally, at least about 0.3 molar equivalents of 1-propylphosphonic anhydride generally are charged to the reaction medium relative to the compound of Formula (VII). In one aspect, at least about 0.5 molar equivalents of 1-propylphosphonic anhydride generally are charged to the reaction medium relative to the compound of Formula (VII). In another aspect, at least about 1.0 molar equivalents of 1-propylphosphonic anhydride generally are charged to the reaction medium relative to the compound of Formula (VII). In another aspect about 0.3 to about 3.0 molar equivalents of 1-propylphosphonic anhydride generally are charged to the reaction medium relative to the compound of Formula (VII). In another aspect about 0.5 to about 2.0 molar equivalents of 1-propylphosphonic anhydride generally are charged to the reaction medium relative to the compound of Formula (VII). In another aspect, about 0.7 to about 1.5 molar equivalents of 1-propylphosphonic anhydride generally are charged to the reaction medium relative to the compound of Formula (VII). In another aspect, about 1.0 to about 1.2 molar equivalents of 1-propylphosphonic anhydride are charged to the reaction medium relative to the compound of Formula (VII).

The base can be any suitable base, particularly a base comprising at least one compound selected from the group consisting of triethylamine, tripropylamine, tributylamine, diisopropylethylamine, N-methylmorpholine, N-methylpyrrolidine, sodium carbonate, sodium bicarbonate, potassium carbonate, and potassium bicarbonate. In one aspect, the base comprises triethylamine. About 1.0 to about 10.0 molar equivalents of the base generally are charged to the reaction medium relative to the compound of Formula (VII). In one aspect, about 2.0 to about 5.0 molar equivalents of the base are charged to the reaction medium relative to the compound of Formula (VII). In another aspect, about 2.4 to about 3.0 molar equivalents of the base are charged to the reaction medium relative to the compound of Formula (VII).

The reaction medium can be any suitable reaction medium, particularly a reaction medium comprising at least one solvent selected from the group consisting of alkyl hydrocarbons, aromatic hydrocarbons, halogenated hydrocarbons, alcohols, ketones, ethers, esters, nitriles, and polar aprotic solvents. In one aspect, the reaction medium comprises at least one solvent selected from the group consisting of dichloromethane, tetrahydrofuran, 2-methyltetrahydrofuran, tert-amyl alcohol, acetone, methyl iso-butyl ketone, 2-butanol, methyl ethyl ketone, acetonitrile, and ethyl acetate. In another aspect, the reaction medium comprises dichloromethane. The volume of reaction medium generally is about 5 liters to about 20 liters of reaction medium per kilogram of compound of Formula (VII) charged to the reaction medium. During the contacting step, the reaction medium generally is maintained at a temperature from about 10° C. to about 30° C.

In general, the aqueous phase comprises greater than about 75 area % of the compound of Formula (VIII) and less than about 2.0 area % of the compound of Formula (XIV) as measured by high-performance liquid chromatography ("HPLC") upon completion of the aqueous phase extraction. In one aspect, the aqueous phase comprises greater than about 80 area % of the compound of Formula (VIII) as measured by HPLC upon completion of the aqueous phase extraction. In another aspect, the aqueous phase comprises greater than about 85 area % of the compound of Formula (VIII) as measured by HPLC upon completion of the aqueous phase extraction. In another aspect, the aqueous phase comprises greater than about 90 area % of the compound of Formula (VIII) as measured by HPLC upon completion of the aqueous phase extraction. In another aspect, the aqueous phase comprises less than about 1.0 area % of the compound of Formula (XIV) as measured by HPLC upon completion of the aqueous phase extraction. In another aspect, the aqueous phase comprises less than about 0.8 area % of the compound of Formula (XIV) as measured by HPLC upon completion of the aqueous phase extraction. In another aspect, the aqueous phase comprises less than about 0.5 area % of the compound of Formula (XIV) as measured by HPLC upon completion of the aqueous phase extraction. In another aspect, the aqueous phase comprises less than about 0.2 area % of the compound of Formula (XIV) as measured by HPLC upon completion of the aqueous phase extraction. In another aspect, the aqueous phase comprises less than about 0.1 area % of the compound of Formula (XIV) as measured by HPLC upon completion of the aqueous phase extraction. In another aspect, the aqueous phase comprises greater than about 80 area % of the compound of Formula (VIII) and less than about 1.0 area % of the compound of Formula (XIV) as measured by HPLC upon completion of the aqueous phase extraction. In another aspect, the aqueous phase comprises greater than about 85 area % of the compound of Formula (VIII) and less than about 0.8 area % of the compound of Formula (XIV) as measured by HPLC upon completion of the aqueous phase extraction. In another aspect, the aqueous phase comprises greater than about 85 area % of the compound of Formula (VIII) and less than about 0.5 area % of the compound of Formula (XIV) as measured by HPLC upon completion of the aqueous phase extraction. In another aspect, the aqueous phase comprises greater than about 85 area % of the compound of Formula (VIII) and less than about 0.2 area % of the compound of Formula (XIV) as measured by HPLC upon completion of the aqueous phase extraction. In another aspect, the aqueous phase comprises greater than about 90 area % of the compound of Formula (VIII) and less than about 0.1 area % of the compound of Formula (XIV) as measured by HPLC upon completion of the aqueous phase extraction. During the aqueous phase extracting step, the aqueous phase generally has a pH less than about 2.5. In one aspect, the aqueous phase has a pH from about 1.8 to about 2.2 during the aqueous phase extracting step.

In general, the organic phase comprises greater than about 75 area % of the compound of Formula (VIII) and less than about 2.0 area % of the compound of Formula (VII) as measured by HPLC upon completion of the organic phase extraction. In one aspect, the organic phase comprises greater than about 80 area % of the compound of Formula (VIII) as measured by HPLC upon completion of the organic phase extraction. In another aspect, the organic phase comprises greater than about 85 area % of the compound of Formula (VIII) as measured by HPLC upon completion of the organic phase extraction. In another aspect, the organic phase comprises greater than about 90 area % of the compound of Formula (VIII) as measured by HPLC upon completion of the organic phase extraction. In another aspect, the organic phase comprises less than about 1.0 area % of the compound of Formula (VII) as measured by HPLC upon completion of the organic phase extraction. In another aspect, the organic phase comprises less than about 0.8 area % of the compound of Formula (VII) as measured by HPLC upon completion of the organic phase extraction. In another aspect, the organic phase comprises less than about 0.6 area % of the compound of Formula (VII) as measured by HPLC upon completion of the organic phase extraction. In another aspect, the organic phase comprises less than about 0.4 area % of the compound of Formula (VII) as measured by HPLC upon completion of the organic phase extraction. In another aspect, the organic phase comprises less than about 0.3 area % of the compound of Formula (VII) as measured by HPLC upon completion of the organic phase extraction. In another aspect, the organic phase comprises greater than about 80 area % of the compound of Formula (VIII) and less than about 1.0 area % of the compound of Formula (VII) as measured by HPLC upon completion of the organic phase extraction. In another aspect, the organic phase comprises greater than about 85 area % of the compound of Formula (VIII) and less than about 0.8 area % of the compound of Formula (VII) as measured by HPLC upon completion of the organic phase extraction. In another aspect, the organic phase comprises greater than about 85 area % of the compound of Formula (VIII) and less than about 0.6 area % of the compound of Formula (VII) as measured by HPLC upon completion of the organic phase extraction. In another aspect, the organic phase comprises greater than about 85 area % of the compound of Formula (VIII) and less than about 0.4 area % of the compound of Formula (VII) as measured by HPLC upon completion of the organic phase extraction. In another aspect, the organic phase comprises greater than about 90 area % of the compound of Formula (VIII) and less than about 0.3 area % of the compound of Formula (VII) as measured by HPLC upon completion of the organic phase extraction. During the organic phase extracting step, the aqueous phase generally has a pH greater than about 4.0. In one aspect, the aqueous phase has a pH from about 4.5 to about 5.0 during the organic phase extracting step.

The organic phase can comprise any suitable solvent, particularly at least one solvent selected from alkyl hydrocarbons, aromatic hydrocarbons, halogenated hydrocarbons, alcohols, ketones, ethers, esters, and nitriles. In one aspect, the organic phase comprises at least one compound selected from the group consisting of dichloromethane, and 2-methyltetrahydrofuran, tert-amyl alcohol, methyl iso-butyl ketone, 2-butanol, methyl ethyl ketone, ethyl acetate, isopropylacetate, N-butylacetate, butyronitrile, toluene, xylene, heptane, hexane, isohexane, and chloroform. In another aspect, the organic phase comprises dichloromethane.

The compound of Formula (VIII) can be isolated from the organic phase by any suitable means, particularly crystallizing the compound of Formula (VIII) from the organic phase. In one aspect, the organic phase comprises an organic phase solvent, and the process further comprises exchanging the organic phase solvent with a replacement solvent to form a crystallization mixture comprising the compound of Formula (VIII). In another aspect, the compound of Formula (VIII) is crystallized from the crystallization mixture. In another aspect, the crystallization mixture is seeded with a crystalline form of the compound of Formula (VIII). In another aspect, the crystallization mixture is seeded with at least about 0.01 relative weight of the crystalline form. In another aspect, the crystallization mixture is seeded with at least about 0.02 relative weight of the crystalline form. In another aspect, the crystallization mixture is seeded with at least about 0.03 relative weight of the crystalline form. In another aspect, the crystalline form is an anhydrate crystalline form.

The organic phase solvent can comprise any suitable solvent, particularly a polar solvent. In one aspect, the organic phase solvent comprises at least one solvent selected from the group consisting of chlorinated hydrocarbons and ethers. In another aspect, the organic phase solvent comprises at least one compound selected from the group consisting of dichloromethane and 2-methyltetrahydrofuran. In another aspect, the organic phase solvent comprises dichloromethane.

The replacement solvent can comprise any suitable solvent. In one aspect, the replacement solvent comprises an alcohol. In another aspect, the replacement solvent comprises ethanol. In another aspect, the organic phase solvent has a boiling point that is lower than the boiling point of the replacement solvent. In another aspect, the boiling point of the organic phase solvent is at least about 20° C. lower than the boiling point of the replacement solvent. In another aspect, the organic phase solvent comprises a polar solvent and the replacement solvent comprises an alcohol. In another aspect, the organic phase solvent comprises dichloromethane and the replacement solvent comprises ethanol.

In one embodiment, the organic phase solvent is exchanged with the replacement solvent by continuous level distillation. In one aspect, the continuous level distillation is conducted under conditions sufficient to maintain the compound of Formula (VIII) in solution during the continuous distillation. In another aspect, the continuous level distillation is continuous level vacuum distillation. In another aspect, the replacement solvent is charged in an amount sufficient to maintain at least about 15 relative volumes of total solvent per kilogram of the compound of Formula (VIII) during the distillation. In another aspect, the replacement solvent is charged in an amount sufficient to maintain at least about 18 relative volumes of total solvent per kilogram of the compound of Formula (VIII) during the distillation. In another aspect, the continuous level vacuum distillation is conducted at a temperature that does not exceed about 60° C.

It generally can be beneficial to maintain the crystallization mixture at a temperature greater than about 40° C. for a period of time after crystallization initiates (e.g., after seeding). In one aspect, the crystallization mixture is maintained at a temperature greater than about 40° C. for at least about one hour after crystallization initiates. In another aspect, the crystallization mixture is maintained at a temperature greater than about 40° C. for at least about two hours after crystallization initiates. In another aspect, the crystallization mixture is maintained at a temperature greater than about 40° C. for at least about three hours after crystallization initiates. In another aspect, the crystallization mixture is maintained at a temperature greater than about 40° C. for at least about four hours after crystallization initiates. In another aspect, the crystallization mixture is maintained at a temperature greater than about 40° C. for at least about five hours after crystallization initiates. In another aspect, the crystallization mixture is seeded with a crystalline form of the compound of Formula (VIII). In another aspect, the crystallization mixture is cooled to a temperature of about 20° C. over a period of at least five hours before isolating the compound of Formula (VIII). In another aspect, the crystallization mixture is seeded with a crystalline form of the compound of Formula (VIII), maintained at a temperature greater than about 40° C. for at least about five hours, and then cooled to a temperature of about 20° C. over a period of at least five hours before isolating the compound of Formula (VIII).

The contacting step generally is carried out as a batch reaction, particularly one where at least about 25 kilograms of the compound of Formula (VII), or salt thereof, are initially charged to the reaction. In one aspect, at least about 50 kilograms of the compound of Formula (VII), or salt thereof, are initially charged to the reaction. In another aspect, at least about 75 kilograms of the compound of Formula (VII), or salt thereof, are initially charged to the reaction. In another aspect, at least about 100 kilograms of the compound of Formula (VII), or salt thereof, are initially charged to the reaction.

The process generally provides at least about a 50% stoichiometric process yield of the compound of Formula (VIII), or salt thereof. In one aspect, the stoichiometric process yield of the compound of Formula (VIII), or salt thereof, is at least about 60%. In another aspect, the stoichiometric process yield of the compound of Formula (VIII), or salt thereof, is at least about 65%. In another aspect, the stoichiometric process yield of the compound of Formula (VIII), or salt thereof, is at least about 70%. In fact, the improved process has been able to deliver approximately 75% yield of good quality material at over 100 kg (input) scale.

In another representative embodiment, the present disclosure relates to a process for preparing a compound having the structure of Formula (VIII):

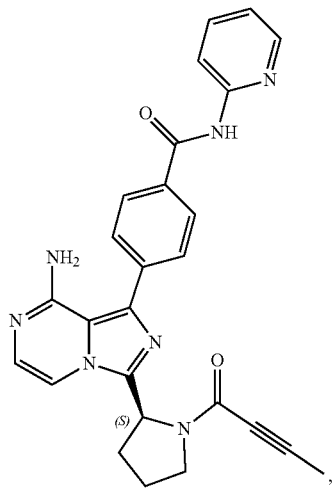

(VIII)

or a salt thereof, wherein the process comprises:
contacting a compound having the structure of Formula (VII):

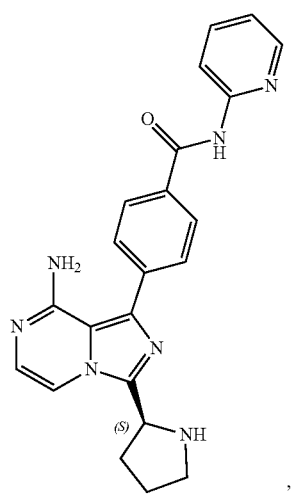

(VII)

or a salt thereof, with 2-butynoic acid, or a salt thereof, in the presence of 1-propylphosphonic anhydride and a base in a reaction medium to form a reaction mixture comprising the compound of Formula (VIII), unreacted compound of Formula (VII), and a reaction by-product, wherein the reaction by-product comprises a compound having the structure of Formula (XIV):

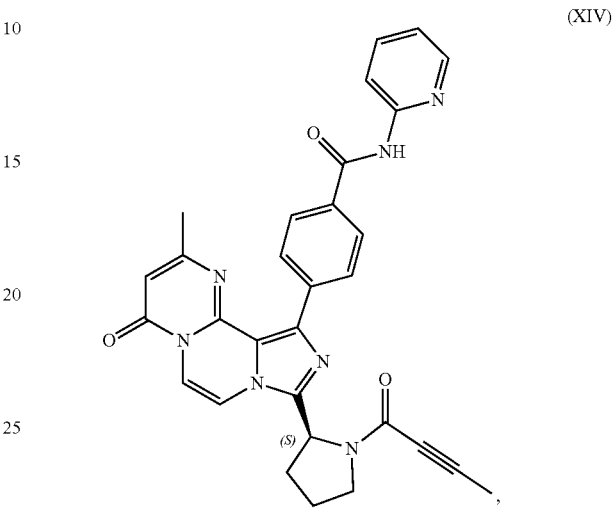

(XIV)

or a salt thereof;
extracting at least a portion of the compound of Formula (VIII), or salt thereof, from the reaction mixture into an aqueous phase having a pH from about 1.8 to about 2.2, wherein the compound of Formula (VIII) is selectively extracted into the aqueous phase relative to the compound of Formula (XIV);
adjusting the pH of the aqueous phase to about 4.5 to about 5.0; and
extracting at least a portion of the compound of Formula (VIII), of salt thereof, from the aqueous phase into an organic phase, wherein the compound of Formula (VIII) is selectively extracted into the organic phase relative to the compound of Formula (VII).

In one aspect, the contacting step comprises adding the compound of Formula (VII) and the base to the reaction medium; adding the 2-butynoic acid to the reaction medium comprising the compound of Formula (VII) and the base; and adding the 1-propylphosphonic anhydride to the reaction medium comprising the compound of Formula (VII), 2-butynoic acid, and the base. In another aspect, the reaction mixture is washed with water and the washed reaction mixture is separated into the aqueous phase and a discard phase, wherein the compound of Formula (VIII) is selectively extracted into the aqueous phase. In another aspect, the organic phase comprises an organic phase solvent, and the process further comprises exchanging the organic phase solvent with a replacement solvent to form a crystallization mixture comprising the compound of Formula (VIII). In another aspect, the process further comprises isolating the compound of Formula (VIII) from the crystallization mixture. In another aspect, the crystallization mixture is seeded with a crystalline form of the compound of Formula (VIII) and maintained at a temperature greater than about 40° C. for at least about five hours after initiating crystallization.

Scheme 18 below corresponds to the process described in Example 17 and illustrates one representative embodiment of the improved process for preparing Compound (VI).

SCHEME 18

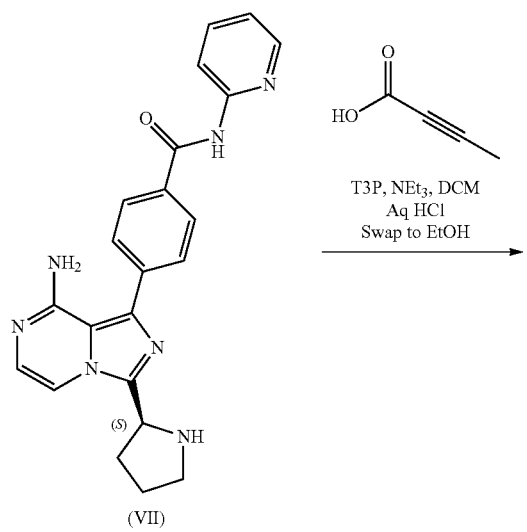

(VII)

T3P, NEt₃, DCM
Aq HCl
Swap to EtOH
→

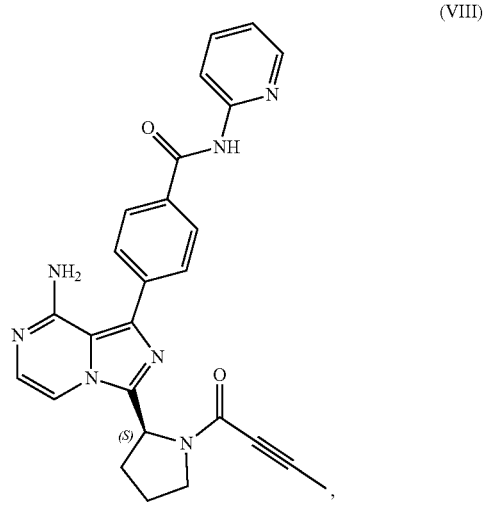

In one embodiment, a compound having the structure of Formula (VIII):

(VIII)

or a salt thereof, is prepared by a process comprising:

contacting a compound having the structure of Formula (VII):

(VII)

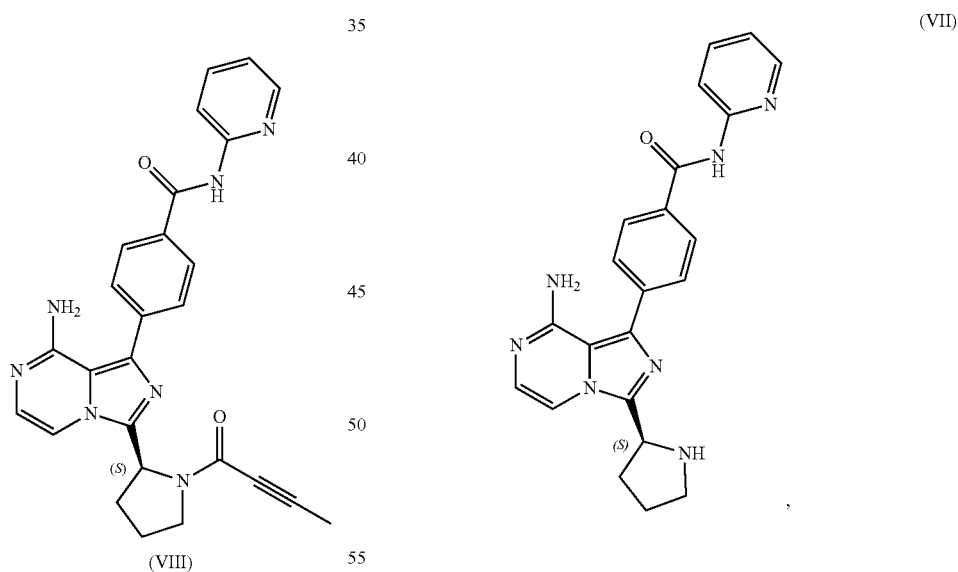

XIII. ADDITIONAL EMBODIMENTS

The various embodiments of the individual processes described above can be combined to provide further embodiments of an overall process for the preparation of acalabrutinib. The embodiments described below are representative embodiments that further describe the overall process. They are intended to illustrate, and not limit, the overall process.

or a salt thereof, with 2-butynoic acid, or a salt thereof, in the presence of 1-propylphosphonic anhydride and a base in a reaction medium to form a reaction mixture comprising the compound of Formula (VIII) and one or more reaction by-products; and selectively isolating the compound of Formula (VIII), or salt thereof, from the reaction mixture relative to the one or more by-products;

wherein the compound having the structure of Formula (VII), or salt thereof, is prepared by a process comprising:
contacting a compound having the structure of Formula (V):

(V)

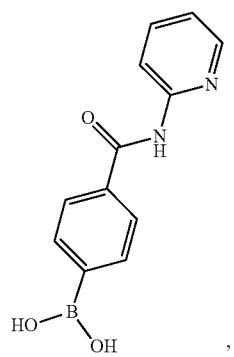

or a salt thereof, with a compound having the structure of Formula (VI):

(VI)

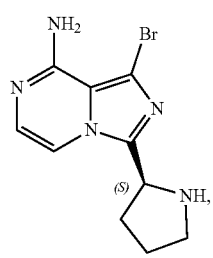

or a salt thereof, in the presence of a base and a palladium catalyst in an aqueous reaction medium comprising an organic solvent to form a reaction mixture comprising the compound of Formula (VII);
  decreasing the amount of water present in the reaction mixture to form a substantially anhydrous mixture comprising the compound of Formula (VII), or salt thereof; and
  isolating the compound of Formula (VII), or salt thereof, from the substantially anhydrous mixture.
In another embodiment, a compound having the structure of Formula (VIII):

(VIII)

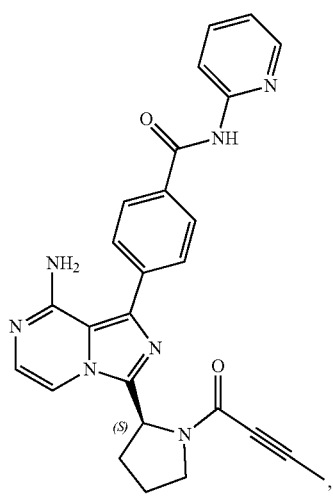

or a salt thereof, is prepared by a process comprising:
contacting a compound having the structure of Formula (VII):

(VII)

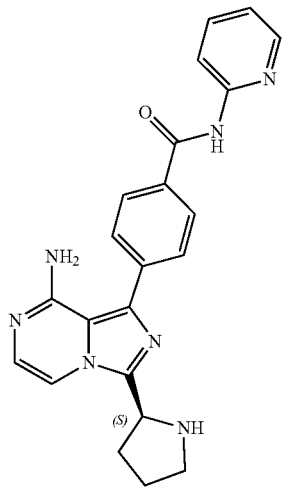

or a salt thereof, with 2-butynoic acid, or a salt thereof, in the presence of a coupling agent and a base in a reaction medium to form a reaction mixture comprising the compound of Formula (VIII), or salt thereof; unreacted compound of Formula (VII), or salt thereof; and a reaction by-product, wherein the reaction by-product comprises a compound having the structure of Formula (XIV):

(XIV)

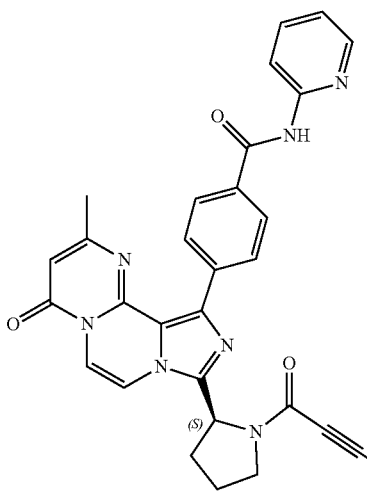

or a salt thereof;
  extracting at least a portion of the compound of Formula (VIII), or salt thereof, from the reaction mixture into an aqueous phase, wherein the compound of Formula (VIII), or salt thereof, is selectively extracted into the aqueous phase relative to the compound of Formula (XIV), or salt thereof;
  adjusting the pH of the aqueous phase; and
  extracting at least a portion of the compound of Formula (VIII), or salt thereof, from the aqueous phase into an organic phase, wherein the compound of Formula (VIII), or salt thereof, is selectively extracted into the organic phase relative to the compound of Formula (VII), or salt thereof;

wherein the compound having the structure of Formula (VII), or salt thereof, is prepared by a process comprising:

contacting a compound having the structure of Formula (V):

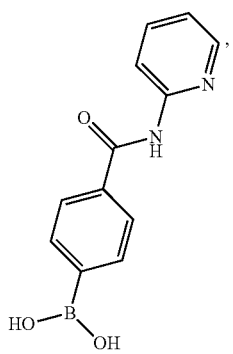

(V)

or a salt thereof, with a compound having the structure of Formula (VI):

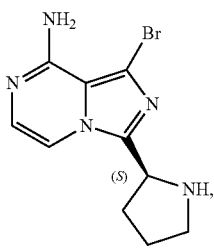

(VI)

or a salt thereof, in the presence of a base and a palladium catalyst in an aqueous reaction medium comprising an organic solvent to form a reaction mixture comprising the compound of Formula (VII), or salt thereof;

decreasing the amount of water present in the reaction mixture to form a substantially anhydrous mixture comprising the compound of Formula (VII), or salt thereof; and isolating the compound of Formula (VII), or salt thereof, from the substantially anhydrous mixture.

In another embodiment, the process further comprises preparing the compound having the structure of Formula (VI), or salt thereof, by a process comprising: contacting a compound of Formula (IV):

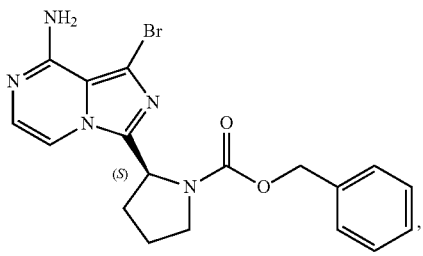

(IV)

or a salt thereof, with an acidic medium under conditions sufficient to deprotect the compound of Formula (IV), or salt thereof, and form a reaction mixture comprising the compound of Formula (VI), or a salt thereof, and a benzyl halide by-product;

removing at least a portion of the benzyl halide by-product from the reaction mixture; and isolating the compound of Formula (VI), or salt thereof, from the reaction mixture under conditions sufficient to substantially avoid the formation of an aminal impurity.

In another embodiment, the process further comprises preparing the compound having the structure of Formula (V), or salt thereof, by a process comprising contacting 4-carboxyphenylboronic acid, or a salt thereof, with thionyl chloride and a catalyst in a reaction medium comprising an organic solvent to form an acyl chloride intermediate which is then contacted in situ with 2-aminopyridine to form a reaction mixture comprising the compound of Formula (V), or salt thereof.

In another embodiment, the process further comprises preparing the compound having the structure of Formula (IV), or salt thereof, by a process comprising contacting a compound having the structure of Formula (III):

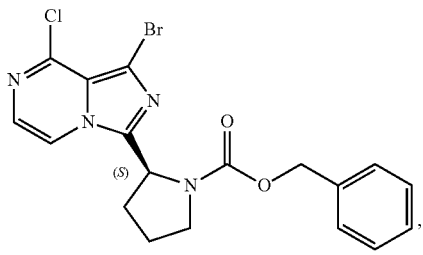

(III)

or a salt thereof, with an aminating agent in a reaction medium to form a reaction mixture comprising the compound of Formula (IV);

forming a sulfate salt of the compound of Formula (IV); and isolating the sulfate salt.

In another embodiment, the process further comprises preparing the compound having the structure of Formula (III), or salt thereof, by a process comprising contacting a compound having the structure of Formula (I):

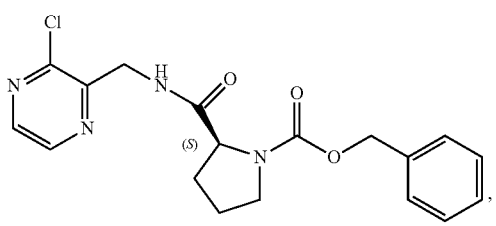

(I)

or a salt thereof, with a cyclizing agent in the presence of a catalyst in a reaction medium to form a compound of Formula (II):

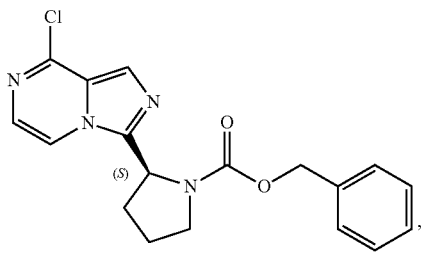

(II)

or salt thereof; and brominating the compound of Formula (II), or salt thereof, with a brominating agent to provide a compound having the structure of Formula (III):

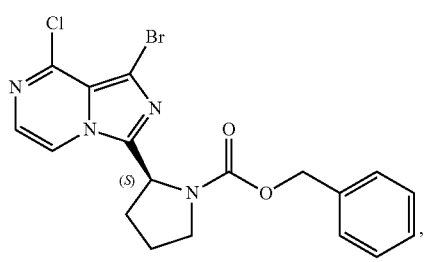

(III)

or a salt thereof;

wherein the temperature of the reaction medium is controlled during the contacting step in a manner sufficient to maintain a chiral purity of at least about 80% for the compound of Formula (II), or salt thereof.

In another embodiment, the present disclosure relates to a process for preparing a compound having the structure of Formula (VIII):

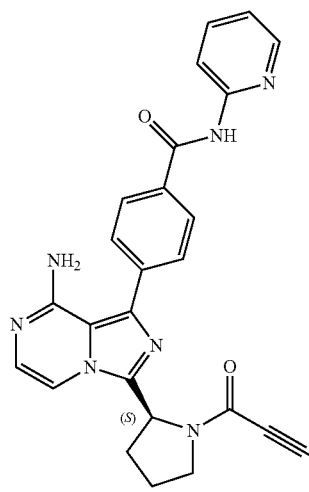

(VIII)

or a salt thereof, wherein the process comprises:

contacting a compound having the structure of Formula (V):

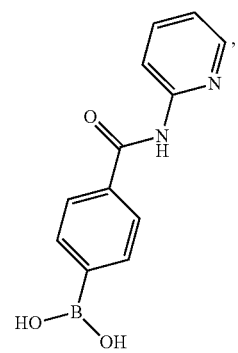

(V)

or a salt thereof, with a compound having the structure of Formula (VI):

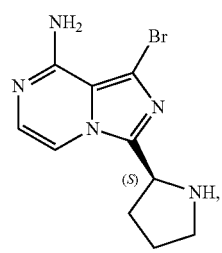

(VI)

or a salt thereof, in the presence of a base and a palladium catalyst in an aqueous reaction medium comprising an organic solvent to form a reaction mixture comprising a compound having the structure of Formula (VII):

(VII)

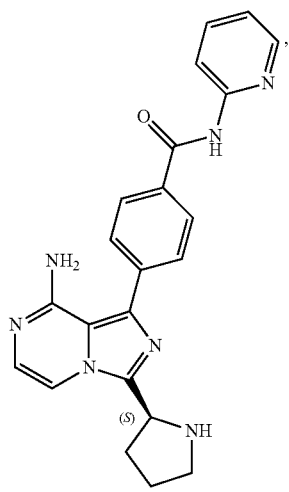

or a salt thereof;

decreasing the amount of water present in the reaction mixture to form a substantially anhydrous mixture comprising the compound of Formula (VII), or salt thereof;

isolating the compound of Formula (VII), or salt thereof, from the substantially anhydrous mixture; and converting the compound of Formula (VII), or salt thereof, to the compound of Formula (VIII), or salt thereof.

In another embodiment, the present disclosure relates to a process for preparing a compound having the structure of Formula (VIII):

(VIII)

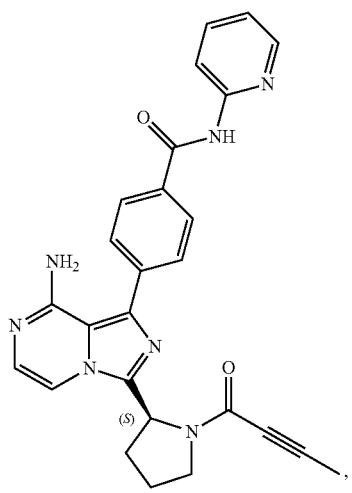

or a salt thereof, wherein the process comprises:
contacting a compound of having the structure of Formula (IV):

(IV)

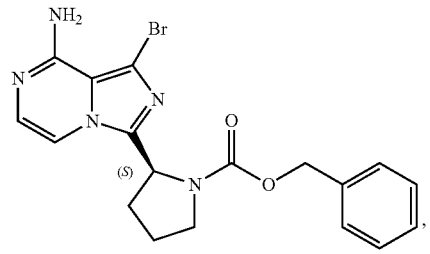

or a salt thereof, with an acidic medium under conditions sufficient to deprotect the compound of Formula (IV), or salt thereof, and form a reaction mixture comprising a compound having the structure of Formula (VI):

(VI)

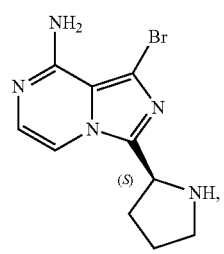

or a salt thereof, and a benzyl halide by-product;
removing at least a portion of the benzyl halide by-product from the reaction mixture;
isolating the compound of Formula (VI), or salt thereof, from the reaction mixture under conditions sufficient to substantially avoid the formation of an aminal impurity; and
converting the compound of Formula (VI), or salt thereof, to the compound of Formula (VIII), or salt thereof.

In another embodiment, the present disclosure relates to a process for preparing a compound having the structure of Formula (VIII):

(VIII)

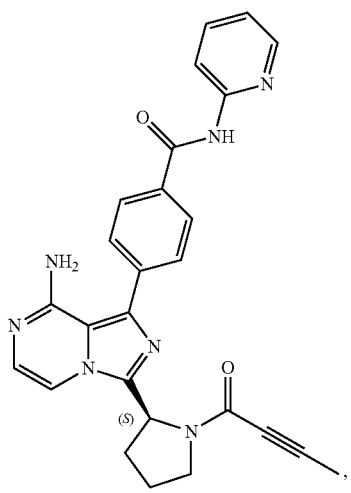

or a salt thereof, wherein the process comprises:
contacting a compound having the structure of Formula (III):

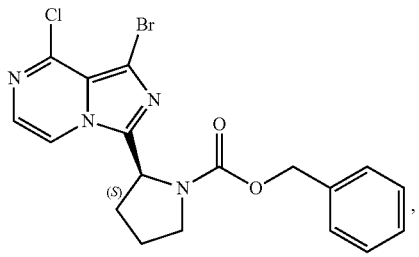

or a salt thereof, with an aminating agent in a reaction medium to form a reaction mixture comprising a compound having the structure of Formula (IV):

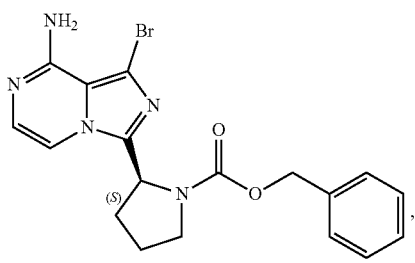

forming a sulfate salt of the compound of Formula (IV);
isolating the sulfate salt; and
converting the sulfate salt to the compound of Formula (VIII), or salt thereof.

In another embodiment, the present disclosure relates to a process for preparing a compound having the structure of Formula (VIII):

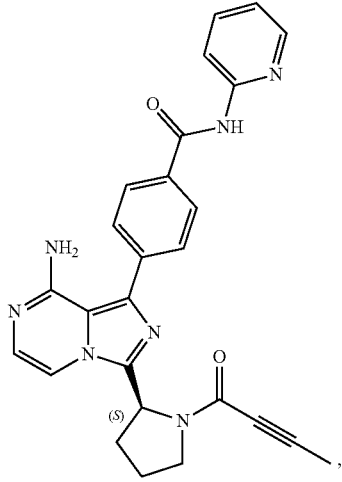

or a salt thereof, wherein the process comprises:
contacting a compound having the structure of Formula (I):

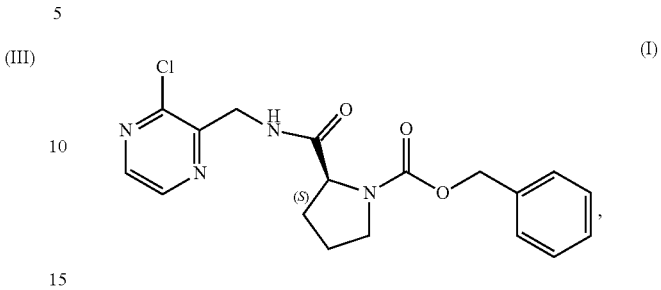

or a salt thereof, with a cyclizing agent in the presence of a catalyst in a reaction medium to form a compound of Formula (II):

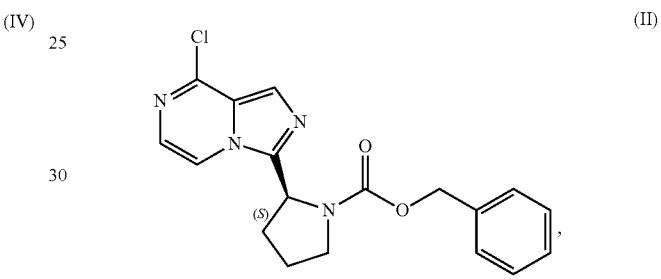

or salt thereof;
brominating the compound of Formula (II), or salt thereof, with a brominating agent to provide a compound having the structure of Formula (III):

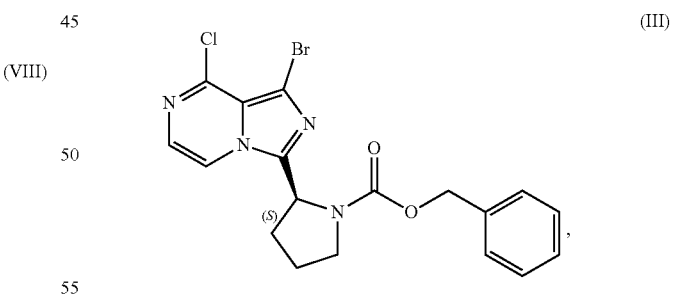

or salt thereof; and
converting the compound of Formula (III), or salt thereof, to the compound of Formula (VIII), or salt thereof;
wherein the temperature of the reaction medium is controlled during the contacting step in a manner sufficient to maintain a chiral purity of at least about 80% for the compound of Formula (II), or salt thereof.

In another embodiment, the present disclosure relates to a process for preparing a compound having the structure of Formula (VIII):

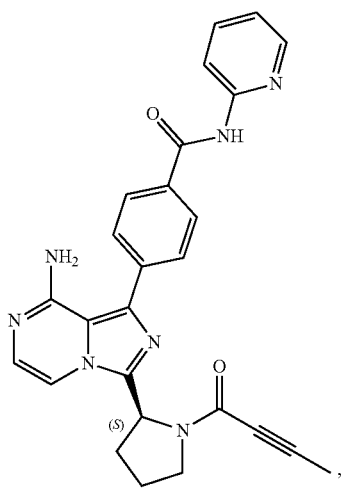

(VIII)

or a salt thereof, wherein the process comprises:

contacting a compound having the structure of Formula (I):

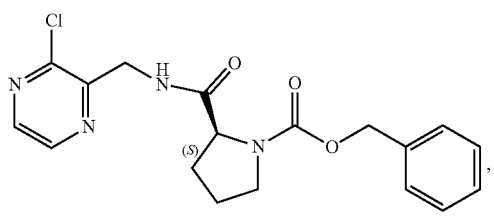

(I)

or a salt thereof, with a cyclizing agent in the presence of a catalyst in a reaction medium to form a compound having the structure of Formula (II):

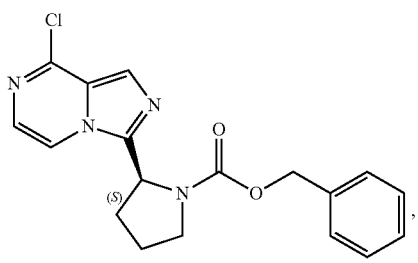

(II)

or salt thereof; and converting the compound of Formula (II), or salt thereof, to the compound of Formula (VIII), or salt thereof;

wherein the temperature of the reaction medium is controlled during the contacting step in a manner sufficient to maintain a chiral purity of at least about 80% for the compound of Formula (II), or salt thereof.

Overall, the improved large-scale process has reduced batch failures and provides high quality acalabrutinib that can be routinely manufactured from Compound (I) on a large scale with greater than 32% yield.

XIV. EXAMPLES

Example 1: Preparation of Benzyl (2S)-2-(1-bromo-8-chloro-imidazo[1,5-a]-pyrazin-3-yl)pyrrolidine-1-carboxylate (Compound (III))

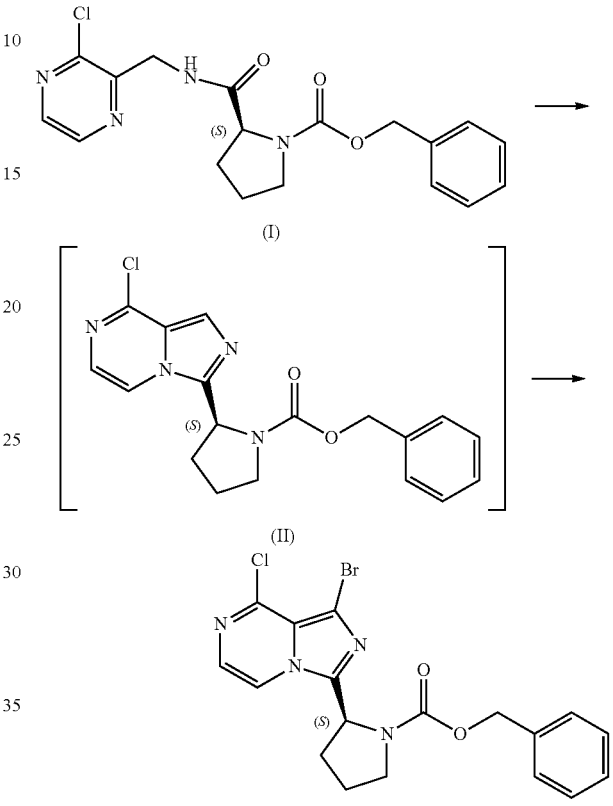

Benzyl (2S)-2-[(3-chloropyrazin-2-yl)methylcarbamoyl] pyrrolidine-1-carboxylate (Compound (I); 179.4 kg, 1.00 mol. eq.) was mixed with acetonitrile (809.6 kg, 4.5 rel. wt.) and N,N-dimethylformamide (6.8 kg, 0.1 mol. eq.), and phosphorus oxychloride (140.2 kg, 1.9 mol. eq.) was added slowly, maintaining a temperature below 25° C. The reaction mixture was heated at 72° C. to 82° C. under a nitrogen sweep to remove the evolved hydrochloric acid, until reaction was shown to be complete. The mixture was cooled to 35° C. to 45° C. then concentrated to approximately 3.6 rel. vol. while maintaining temperature below 45° C. Acetonitrile (350.2 kg, 1.95 rel. wt.) was added and the mixture concentrated to approximately 3.6 rel. vol. maintaining temperature below 45° C., repeating this operation a further one time. The mixture was cooled to 15° C. to 25° C. and then transferred slowly to a cooled solution of sodium bicarbonate (136.6 kg, 8.0 mol. eq.), water (1139 L, 6.3 rel. vol.), and ice (375.8 kg, 2.1 rel. wt.).

The product was then extracted from the mixture twice with dichloromethane (905 kg, 5.0 rel. wt.). The combined organic extracts were then washed with a solution of sodium bicarbonate (114.4 kg) in water (1139 L), then a solution of sodium chloride (75 kg) in water (376 L), filtered through celite (18 kg), and then filtered through silica (40 kg), washing the silica filter cake with dichloromethane (909 kg), twice. The solvent was removed by vacuum distillation, maintaining temperature below 40° C., to approximately 1.0 rel. vol. N-Methylpyrrolidone (819 kg, 4.6 rel. wt.) was added to dissolve the mixture followed by N-bromosuccinimide (77.3 kg, approximately 1.1 mol. eq.) in increments, stirring at 20° C. to 30° C. after each charge until the reaction was deemed complete. The mixture was then added to a solution of sodium bicarbonate (21.8 kg) in water (1092 L) and then the product was extracted with dichloromethane (1500 kg, 8.4 rel. wt.) and then dichloromethane (907 kg, 5.1 rel. wt.). The organic phases were combined and washed three times with water (682 L) and an additional eight times with water (382 L). The organic solution was concentrated to approximately 1.0 rel. vol. and concentrated from heptane (191 kg, 1.1 rel. vol.), before adding heptane (191 kg, 1.1 rel. vol.) to crystallize. Filtered and dried to yield solid benzyl (2S)-2-(1-bromo-8-chloro-imidazo[1,5-a]pyrazin-3-yl)pyrrolidine-1-carboxylate (Compound (III), 152.2 kg, 75.6%). Enantiomeric excess=97.8%.

The above-described process conditions, however, frequently resulted in batches having reduced chiral purity and yield, and at times even resulted in batch failures. The evolved hydrochloric acid generated acidic conditions which lead to racemization of the benzyl (2S)-2-[(3-chloropyrazin-2-yl)methylcarbamoyl]-pyrrolidine-1-carboxylate starting material. Although use of a nitrogen sweep to remove the evolved hydrochloric acid decreased the extent of racemization, control over the extent of chiral erosion was still highly variable.

Example 2: Preparation of Benzyl (2S)-2-(8-chloro-imidazo[1,5-a]pyrazin-3-yl)pyrrolidine-1-carboxylate (Compound (II))

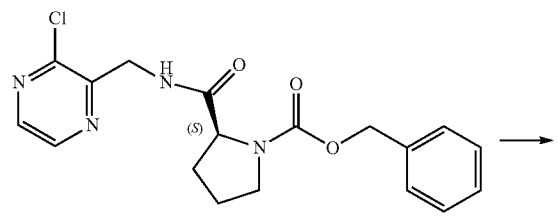

The effect of decreasing reaction temperature and increasing N,N-dimethylformamide loading on the chiral purity of benzyl (2S)-2-(8-chloro-imidazo[1,5-a]pyrazin-3-yl)pyrrolidine-1-carboxylate relative to the conditions of Example 1 was evaluated. As described below, increasing the amount of the N,N-dimethylformamide catalyst to at least 0.6 mol. eq. increased the reaction rate and allowed the reaction to be conducted at a lower temperature. These changes in process conditions increased the yield and provided improved control over the chiral purity of the product.

In four vials with magnetic stir bars benzyl (2S)-2-[(3-chloropyrazin-2-yl)methylcarbamoyl]pyrrolidine-1-carboxylate (Compound (I), 1.00 g) was combined with acetonitrile (5 ml) and N,N-dimethylformamide was added (0.08, 0.12, 0.16 and 0.20 g; 0.4, 0.6, 0.8 and 1.0 mol. eq.). Phosphorous oxychloride (0.82 g, 2.0 mol. eq.) was added to each vial and the contents were agitated for 15 minutes, then placed in a heat block preheated to 42° C., and agitated. Internal vial temperature reached 41° C. From each vial a 0.50 ml sample was drawn at 1, 3, 5 and 21 hours. Samples were quenched into 10 ml saturated sodium bicarbonate solution, extracted into 5 ml of methyl tert-butyl ether, and the organic layer was separated and dried over magnesium sulfate. Extracts were analyzed by HPLC for purity and chirality. The results are shown in Table 3 below.

TABLE 3

| Hours | DMF (Mol. Eq.) | Compound (I) Purity (%) | Compound (II) Purity (%) | Compound (II) Chiral Purity (S/R) |
|---|---|---|---|---|
| 1 | 0.4 | 30.3 | 69.7 | |
| 1 | 0.6 | 6.2 | 92.9 | |
| 1 | 0.8 | 1.7 | 96.9 | |
| 1 | 1.0 | 0.6 | 97.8 | |
| 3 | 0.4 | 5.8 | 92.2 | |
| 3 | 0.6 | 1.1 | 97.0 | >99.9/0.01 |
| 3 | 0.8 | ND | 98.3 | |
| 3 | 1.0 | ND | 97.9 | |
| 5 | 0.4 | 3.3 | 94.3 | |
| 5 | 0.6 | ND | 98.1 | >99.9/0.01 |
| 5 | 0.8 | ND | 93.4 | |
| 5 | 1.0 | ND | 97.7 | |
| 21 | 0.4 | — | — | |
| 21 | 0.6 | ND | 98.1 | >99.9/0.01 |
| 21 | 0.8 | ND | 98.3 | |
| 21 | 1.0 | ND | 97.7 | |

Example 3: Preparation of Benzyl (2S)-2-(1-bromo-8-chloro-imidazo[1,5-a]pyrazin-3-yl)pyrrolidine-1-carboxylate (Compound (III))

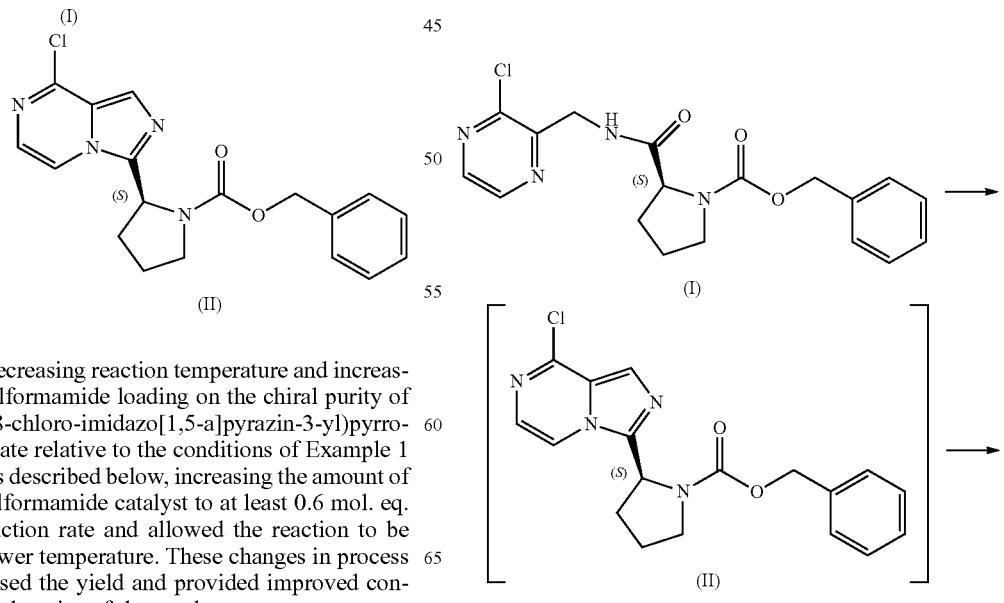

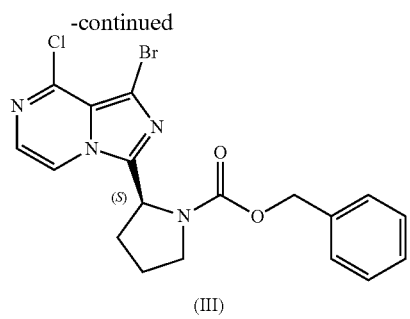

(III)

The synthesis described in Example 1 was modified in view of the results of Example 2 and the modified process conducted at large scale. The modified process provided improved yield, and largely avoided the racemization problems previously encountered during cyclization.

Benzyl (2S)-2-[(3-chloropyrazin-2-yl)methylcarbamoyl] pyrrolidine-1-carboxylate (Compound (I), 337.5 kg, 1.00 mol. eq.) was mixed with acetonitrile (1688 L, 5.0 rel. vol.) and N,N-dimethylformamide (39.5 kg, 0.6 mol. eq.) and phosphorus oxychloride (276.1 kg, 2.0 mol. eq.) was added slowly, maintaining a temperature below 30° C. The reaction mixture was heated for 3 hours at 40° C. The mixture was cooled and then transferred slowly to a cooled solution of sodium bicarbonate (605.1 kg, 8.0 mol. eq.) and water (3375 L, 10.0 rel. vol.). The product was then extracted from the mixture three times with methyl tert-butyl ether (1013 L, 3.0 rel. vol.). The combined organic extracts were then washed with a solution of sodium bicarbonate (151.3 kg, 2.0 mol. eq.) in water (2025 L, 6.0 rel. vol.), then 25% w/w aqueous brine solution (675 kg, 2.0 rel. wt.), and then circulated through a bag filter containing magnesium sulfate. The solvent was removed by vacuum distillation (jacket temperature 30° C.) resulting in a dark red oil. N,N-Dimethylformamide (1350 L, 4.0 rel. vol.) was added to dissolve the oil followed by N-bromosuccinimide (160.3 kg, 1.0 mol. eq.) in increments, stirring at 20° C. after each charge. After the reaction was deemed complete, the mixture was cooled to 5° C. and a solution of 2% w/w aqueous sodium bicarbonate (2531 L, 7.5 rel. vol.) was slowly added to precipitate the product, maintaining temperature below 10° C. The mixture was filtered and washed with a pre-mixed solution of water (675 L, 2.0 rel. vol.) and N,N-dimethylformamide (338 L, 1.0 rel. vol.), and then washed twice with water (675 L, 2.0 rel. vol.). The resulting solids were returned to the reactor and reslurried in water (1688 L, 5.0 rel. vol.). The product was isolated and washed twice with water (675 L, 2.0 rel. vol.) and dried under vacuum at 45° C. to yield solid benzyl (2S)-2-(1-bromo-8-chloro-imidazo[1,5-a]pyrazin-3-yl)pyrrolidine-1-carboxylate (Compound (III), 353.6 kg, 90.1%). Enantiomeric excess=>99.8%.

This compound exists as a mixture of conformers in solution and resonances are quoted for the major conformer only. 1H NMR (500 MHz, DMSO-d6) δ 1.86-1.94 (m, 1H), 2.02-2.09 (m, 1H), 2.10-2.18 (m, 1H), 2.27-2.34 (m, 1H), 3.49-3.54 (m, 1H), 3.55-3.61 (m, 1H), 4.59 (d, J=12.3 Hz, 1H), 4.99 (d, J=12.3 Hz, 1H), 5.41 (dd, J=7.7, 4.6 Hz, 1H), 6.67-6.71 (m, 2H), 7.08-7.13 (m, 2H), 7.16-7.22 (m, 2H), 8.28 (d, J=5.0 Hz, 1H). 13C NMR (126 MHz, DMSO-d6) δ 23.5, 32.3, 46.9, 51.5, 65.9, 109.6, 115.4, 119.3, 126.7, 127.1, 127.7, 128.0, 136.0, 142.8, 143.0, 153.3.

Example 4: Preparation of Sulfate Salt of Benzyl (2S)-2-(8-amino-1-bromoimidazo[1,5-a]pyrazin-3-yl)-1-pyrrolidinecarboxylate (Sulfate Salt of Compound (IV))

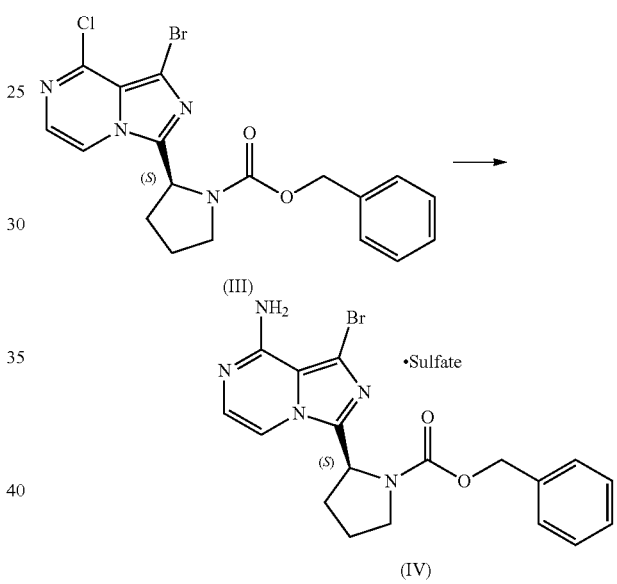

Benzyl (2S)-2-(1-bromo-8-chloro-imidazo[1,5-a]pyrazin-3-yl) pyrrolidine-1-carboxylate (Compound (III), 90.0 kg, 1.00 mol. eq.) was mixed with iso-propanol (351 kg, 3.0 rel. wt.) and N-methylpyrrolidone (180 kg, 2.0 rel. wt.) in a sealed autoclave. Ammonia (451 kg, 5.0 rel. wt.) was pumped into the mixture, which was then heated to 90° C. to 95° C. until the reaction was complete. The reaction mixture was cooled to 50° C. to 60° C. and added to water (900 kg, 10.0 rel. vol.). Cooled to 20° C. to 30° C. and extracted with dichloromethane (957 kg, 10.6 rel. wt.), and then dichloromethane (360 kg, 4.0 rel. wt.). Combined the organic phases and washed with water and then concentrated to approximately 2.5 rel. vol. Ethanol (574 kg, 6.4 rel. wt.) was added to the mixture and then concentrated sulfuric acid (30.4 kg, 1.5 mol. eq.) was slowly added maintaining temperature below 25° C. The resulting slurry was cooled to 0° C. to 5° C. and then filtered and dried at 40° C. under vacuum to yield an off-white crystalline solid that is a sulfate salt of benzyl (2S)-2-(8-amino-1-bromoimidazo[1,5-a] pyrazin-3-yl)-1-pyrrolidinecarboxylate (Compound (IV), 89.2 kg, 83.5%, based on assumption of the monosulfate salt).

Example 5: Preparation of Sulfate Salt (2:3) of Benzyl (2S)-2-(8-amino-1-bromoimidazo[1,5-a]pyrazin-3-yl)-1-pyrrolidinecarboxylate (Compound (IV))

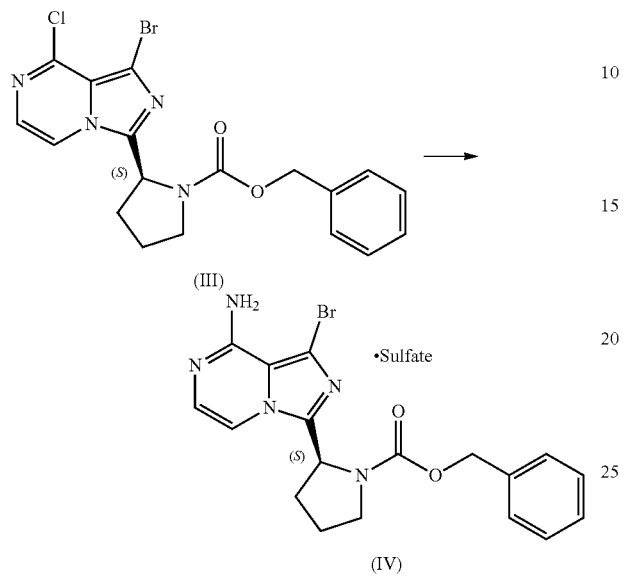

The synthesis described in Example 4 assumed that the final product would have a 1:1 freebase to salt ratio, but the assay and mass balance did not correspond. Therefore, the synthesis was further modified as described below to yield a final product with a defined stoichiometry that could satisfy regulatory requirements for the characterization of an intermediate used in the preparation of a registered drug substance. The presence of inorganic ammonium sulfate in the product of Example 4 caused difficulty in accurately determining the stoichiometry of the sulfate salt. The modified process below removes residual ammonia prior to generation of the sulfate salt and substantially eliminates this problem.

Benzyl (2S)-2-(1-bromo-8-chloro-imidazo[1,5-a]pyrazin-3-yl)pyrrolidine-1-carboxylate (Compound (III), 336.5 kg, 1.00 mol. eq.) was mixed with 2-butanol (1683 L, 5.0 rel. vol.) and 30% w/w ammonium hydroxide (841 kg, 2.5 rel. wt.) in a sealed autoclave, and heated to 90° C. to 95° C. for 32 hours. The reaction mixture was cooled to 20° C. and the lower aqueous phase was removed. The organic phase was washed twice with 50:50 brine:water solution (337 L, 1.0 rel. vol.) and then distilled under vacuum at approximately 40° C. to approximately one third of its volume. 2-Butanol (1346 L, 4.0 rel. vol.) and water (841 L, 2.5 rel. vol.) were added to dissolve the oil, and the lower aqueous phase removed and discarded. The organic phase was filtered to remove interfacial material and then 93% sulfuric acid (122.2 kg, 1.5 mol. eq.) was slowly added maintaining temperature below 25° C. The resulting slurry was cooled to 0° C. to 5° C. and then filtered and washed with 10% v/v aqueous 2-butanol (673 L, 2.0 rel. vol.) before drying at 40° C. under vacuum to yield an off-white crystalline solid that is a sulfate salt of benzyl (2S)-2-(8-amino-1-bromoimidazo[1,5-a]pyrazin-3-yl)-1-pyrrolidine-carboxylate (Compound (IV), 324.4 kg, 87.2%, calculated as a sulfate salt (2:3).

This compound exists as a mixture of conformers in solution and resonances are quoted for the major conformer only. 1H NMR (500 MHz, DMSO-d6 with 10% TFA) δ 1.84-1.94 (m, 1H), 1.98-2.05 (m, 1H), 2.07-2.17 (m, 2H), 2.25-2.34 (m, 1H), 3.47-3.60 (m, 2H), 4.57 (d, J=12.1 Hz, 1H), 5.02 (d, J=12.1 Hz, 1H), 5.30 (dd, J=7.6, 5.3 Hz, 1H), 6.79-6.84 (m, 3H), 7.12-7.22 (m, 3H), 7.73 (d, J=6.0 Hz, 1H), 9.48 (br s, 2H). 13C NMR (126 MHz, DMSO-d6 with 10% TFA) δ 23.8, 32.7, 47.2, 51.6, 66.4, 108.8, 112.9, 116.1, 117.1, 127.9, 128.2, 128.3, 136.4, 147.3, 148.7, 153.5. X-ray powder diffraction of the solid gave a diffractogram consistent with that of FIG. 1.

Example 6: Analysis of Sulfate Salt of Benzyl (2S)-2-(8-amino-1-bromoimidazo[1,5-a]pyrazin-3-yl)-1-pyrrolidinecarboxylate (Sulfate Salt of Compound (IV))

A. Confirmation of Salt Stoichiometry

In four vials with magnetic stir bars purified benzyl (2S)-2-(8-amino-1-bromoimidazo[1,5-a]pyrazin-3-yl)-1-pyrrolidinecarboxylate (Compound (IV) freebase, 500 mg) was combined with ethanol (8 ml) and concentrated sulfuric acid was added (0.25, 0.50, 0.75, and 1.0 mol. eq.). Held for one hour and then cooled to 0° C. for one hour, before filtering and drying under vacuum. The results are presented in Table 4 below and demonstrate that the stoichiometry is inconsistent with the previously assumed 1:1 salt ratio, but is consistent with a 2:3 ratio.

TABLE 4

| $H_2SO_4$ Added (Mol. Eq.) | Yield (Mg) | Assay By NMR (Based on Sulfate:Freebase Ratio of . . .) | | | Ethanol Content (% W/W) | Water Content (% W/W) | Mass Balance (% W/W) Based on Sulfate:Freebase Ratio of . . . | | |
|---|---|---|---|---|---|---|---|---|---|
| | | 1:1 | 1:2 | 2:3 | | | 1:1 | 1:2 | 2:3 |
| 0.25 | 196 mg | 101.8 | 92.1 | 95 | 0.85 | 3.6 | 106.3 | 96.6 | 99.5 |
| 0.50 | 397 mg | 101.9 | 92.2 | 95.2 | 1.23 | 3.5 | 106.6 | 96.9 | 99.9 |
| 0.75 | 556 mg | 101.8 | 92.1 | 95.1 | 0.76 | 3 | 105.6 | 95.9 | 98.9 |
| 1.00 | 541 mg | 100.5 | 90.9 | 93.9 | 1.24 | 3.7 | 105.4 | 95.8 | 98.8 |

B. Single Crystal X-Ray Diffraction Analysis

Single crystals of a sulfate salt of benzyl (2S)-2-(8-amino-1-bromoimidazo[1,5-a]pyrazin-3-yl)-1-pyrrolidinecarboxylate (Compound (IV)) were grown by slow evaporation from dimethyl sulfoxide. A suitable crystal for single X-ray diffraction was identified and analyzed by single crystal diffraction. Details of the crystal data: $3(C_{18}H_{19}BrN_5O_2)\cdot SO_4\cdot HSO_4\cdot H_2O$., $M_r$=1463.02, trigonal, R3 (No. 146), a=15.89896(17) Å, b=15.89896(17) Å, c=20.9836(3) Å, α=90°, β=90°, γ=120°, V=4593.54(12) Å³, T=100(2) K, Z=3, Z'=0.33333, μ(CuKα)=3.748, 30561 reflections measured, 3873 unique ($R_{int}$=0.0306) which were used in all calculations. The final $wR_2$ was 0.0791 (all data) and $R_f$ was 0.0292 (I>2(I)). Flack Parameter=−0.023(5).

The stoichiometry was confirmed to be three molecules of benzyl (2S)-2-(8-amino-1-bromoimidazo[1,5-a]pyrazin-3-yl)-1-pyrrolidinecarboxylate to one sulfate to one hydrogen sulfate. Although the analysis of the crystal structure also identified one molecule of water per three molecules of benzyl (2S)-2-(8-amino-1-bromoimidazo[1,5-a]pyrazin-3-yl)-1-pyrrolidinecarboxylate, further diffraction studies and thermal analysis indicate that this can be variable without materially affecting the overall structure or salt stoichiometry.

C. X-Ray Powder Diffraction Analysis

X-ray powder diffraction data were collected by mounting the sulfate salt of benzyl (2S)-2-(8-amino-1-bromoimidazo[1,5-a]pyrazin-3-yl)-1-pyrrolidinecarboxylate (Compound (IV)) powder onto a silicon wafer mount and analyzing the sample using the Bruker D4 Endeavour diffractometer ($\lambda$=1.5418 Å). The sample was measured in reflection geometry in θ-2θ scan mode configuration over the scan range 2° to 40° 2θ with 0.12 second exposure per 0.02° increment. The X-rays were generated by a copper long-fine focus tube operated at 40 kV and 40 mA. The resulting X-ray diffraction pattern is shown in FIG. 1 with selected peaks and relative intensities reported in Table 5 below.

TABLE 5

| PEAK | RELATIVE INTENSITY |
|---|---|
| 7.7 | 23 |
| 10.6 | 49 |
| 11.1 | 8 |
| 12.6 | 100 |
| 13.0 | 2 |
| 13.5 | 59 |
| 16.8 | 3 |
| 17.4 | 51 |
| 18.0 | 42 |
| 18.9 | 30 |
| 19.2 | 43 |
| 21.1 | 18 |
| 21.9 | 81 |
| 23.0 | 28 |
| 23.5 | 99 |
| 23.9 | 41 |
| 24.6 | 93 |
| 25.2 | 36 |
| 26.0 | 38 |
| 27.0 | 37 |
| 27.6 | 35 |
| 28.3 | 49 |
| 28.6 | 34 |
| 29.3 | 20 |
| 30.2 | 13 |
| 31.3 | 19 |
| 32.1 | 28 |

Characteristic peaks for this crystalline form include the peaks at 7.7, 10.6, 11.1, 12.6, 13.5, 17.4, 18.0, 18.9, 19.2, and 21.9±0.2 °2θ, particularly the peaks at 7.7, 10.6, 11.1, 12.6, and 13.5±0.2 °2θ.

Example 7: Preparation of 1-bromo-3-[(2S)-2-pyrrolidinyl]imidazo[1,5-a]pyrazin-8-amine (Compound (VI))

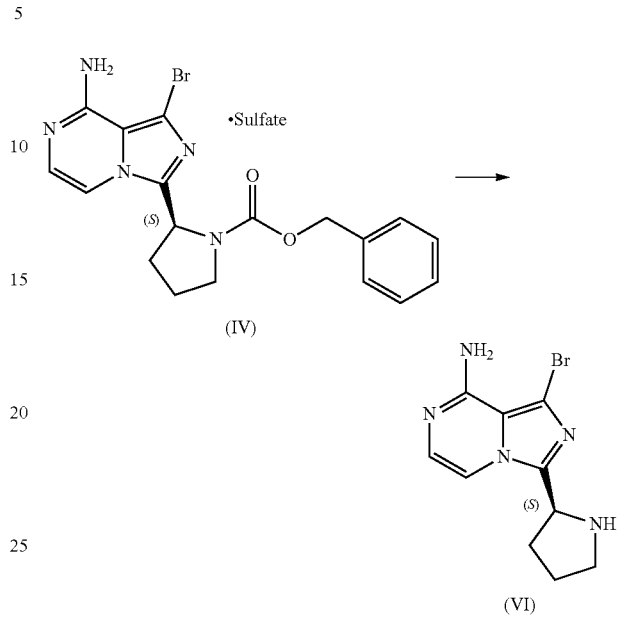

The sulfate salt (2:3) of benzyl (2S)-2-(8-amino-1-bromoimidazo[1,5-a]pyrazin-3-yl)-1-pyrrolidinecarboxylate (Compound (IV), 261 kg, 1.0 mol. eq.) and concentrated aqueous hydrochloric acid (996 L, 3.8 rel. wt.) were mixed and heated to 40° C. to 50° C. for at least two hours under an inert atmosphere. The batch was cooled and washed four times with methyl tert-butyl ether (192 kg, 4×0.73 rel. wt.). Aqueous sodium hydroxide solution was added slowly, with cooling, to achieve a pH greater than 12. The product was extracted with dichloromethane (3632 kg, 13.9 rel. wt.), clarified with Celite, and then decolourized with charcoal (13 kg, 0.05 rel. wt.). The organic extract was concentrated, at atmospheric pressure, to approximately 0.86 rel. vol. Methyl tert-butyl ether (519 L, 1.99 rel. wt.) was added, the mixture was cooled to 20° C. and the resulting slurry was filtered and washed with a mixture of methyl tert-butyl ether, before drying under vacuum at 40° C. to yield solid 1-bromo-3-[(2S)-2-pyrrolidinyl]imidazo[1,5-a]pyrazin-8-amine (Compound (VI), 119 kg, 78% yield).

Example 8: Preparation of 1-bromo-3-[(2S)-2-pyrrolidinyl]imidazo[1,5-a]pyrazin-8-amine (Compound (VI))

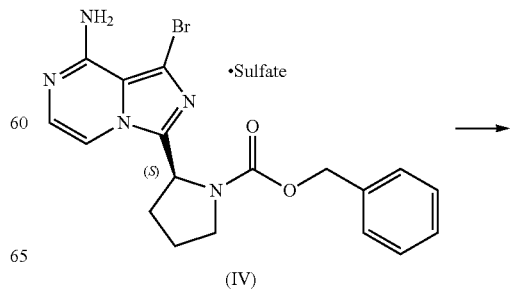

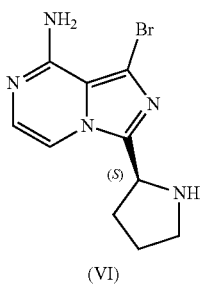

(VI)

The sulfate salt (2:3) of benzyl (2S)-2-(8-amino-1-bromoimidazo[1,5-a]pyrazin-3-yl)-1-pyrrolidinecarboxylate (Compound (IV), 370 kg) and concentrated aqueous hydrochloric acid were mixed and heated to 50° C. for at least six hours. The batch was cooled and washed with methyl tert-butyl ether and then heptane. Aqueous sodium hydroxide solution was added slowly, with cooling, to achieve a pH greater than 12. The product was extracted with dichloromethane and methanol was added. The solution was clarified with Celite and then decolourized with charcoal. The organic extract was concentrated at atmospheric pressure and swapped to methyl tert-butyl ether. The resulting mixture was cooled, the resulting slurry was filtered and washed with a mixture of methyl tert-butyl ether, and then dried under vacuum to yield solid 1-bromo-3-[(2S)-2-pyrrolidinyl]imidazo[1,5-a]pyrazin-8-amine (Compound (VI), 188.8 kg). The product required further purification to remove aminal impurities by slurrying the product in ethyl acetate, filtering, and washing the filter cake with ethyl acetate.

Example 9: Preparation of 1-bromo-3-[(2S)-2-pyrrolidinyl]imidazo[1,5-a]pyrazin-8-amine (Compound (VI))

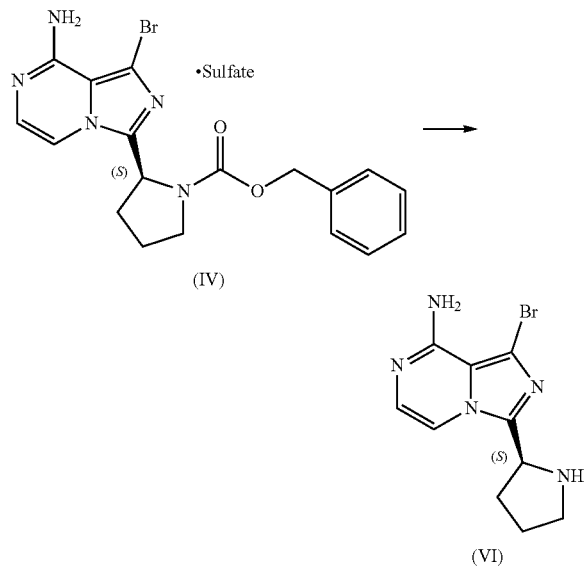

The syntheses exemplified in Examples 7 and 8 at times resulted in elevated impurities (e.g. aminal impurity when dichloromethane was used as the extraction solvent) and poor operability. Therefore, the process described below was developed to improve the purity of the final product.

The sulfate salt (2:3) of benzyl (2S)-2-(8-amino-1-bromoimidazo[1,5-a]pyrazin-3-yl)-1-pyrrolidinecarboxylate (Compound (IV), 343 kg, 1.0 mol. eq.) and 37% w/w aqueous hydrochloric acid (1142 L, 3.33 rel. vol.) were mixed and heated to 40° C. for 14 hours under an inert atmosphere. The batch was cooled and washed twice with heptane (1715 L, 5.0 rel. vol.). Aqueous 30% w/w sodium hydroxide solution (104.4 kg, 1.10 mol. eq.) was added slowly, with cooling, to achieve a pH greater than 10. The product was extracted twice with 2-methyltetrahydrofuran (2401 L, 7.0 rel. vol.) and the combined extracts were washed with water (343 L, 1.0 rel. vol.) before being concentrated, at atmospheric pressure, to a volume of 3.5 rel. vol. 2-Methyltetrahydrofuran (1029 L, 3.0 rel. vol.) was added, and the mixture was concentrated, at atmospheric pressure, to a volume of 1200 L, 3.5 rel. vol. The mixture was cooled to 70° C. and crystalline 1-bromo-3-[(2S)-2-pyrrolidinyl]imidazo[1,5-a]pyrazin-8-amine (Compound (VI), 0.34 kg, 0.001 rel. wt.) was added to seed the mixture. The mixture was cooled to 20° C., and heptane (686 L, 2.0 rel. vol.) was added. The resulting slurry was filtered and washed with a mixture of 2-methyltetrahydrofuran (309 L, 0.90 rel. vol.) and heptane (206 L, 0.60 rel. vol.), before drying under vacuum at 40° C. to yield a tan crystalline solid 1-bromo-3-[(2S)-2-pyrrolidinyl]imidazo[1,5-a]pyrazin-8-amine (Compound (VI), 168 kg, 84% yield).

1H NMR (500 MHz, DMSO-d6) δ 1.65-1.75 (m, 1H), 1.77-1.86 (m, 1H), 1.98-2.06 (m, 1H), 2.09-2.17 (m, 1H), 2.75-3.06 (m, 3H), 4.44 (dd, J=7.6, 6.7 Hz, 1H), 6.61 (br s, 2H), 6.96 (d, J=5.0 Hz, 1H), 7.70 (d, J=5.0 Hz, 1H). 13C NMR (126 MHz, DMSO-d6) δ 25.7, 29.4, 46.5, 54.0, 105.1, 107.5, 115.3, 128.1, 142.8, 150.8.

Example 10: Preparation of [4-(2-Pyridylcarbamoyl)phenyl]boronic acid (Compound (V))

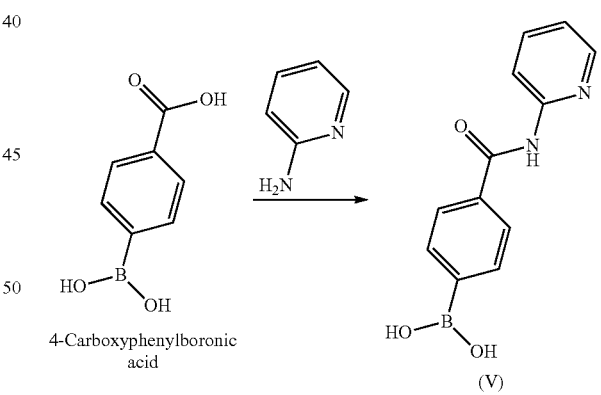

4-Carboxyphenylboronic acid (V)

4-Carboxyphenylboronic acid (116.0 kg, 1.0 mol. eq.) was mixed with toluene (696 kg, 6.0 rel. vol.) and N,N-dimethylformamide (2.0 kg, 0.04 mol. eq.) at 50° C. Thionyl chloride (249.5 kg, 3.0 mol. eq.) was charged slowly to the slurry. The reaction was heated to 60° C. and agitated for 8 hours before being cooled. The mixture was then concentrated under vacuum to remove 348 L (3.0 rel. vol.) of solvent, and then toluene (348 L, 3.0 rel. vol.) was added. This was repeated a further three times to remove the excess thionyl chloride. The mixture was then concentrated under vacuum to remove 348 L (3.0 rel. vol.) of solvent and then pyridine (348 L, 3.0 rel. vol.) was added. This was repeated once to remove the toluene. Pyridine (580 L, 5.0 rel. vol.) was added to the slurry and the mixture was cooled to −5° C. A solution of 2-aminopyridine (131.6 kg, 2.0 mol. eq.) in pyridine (232.0 L, 2.0 rel. vol.) was added as quickly as possible while maintaining temperature below 20° C. The reaction was slowly heated to 65° C. to 70° C. and agitated for 8 hours. The mixture was then concentrated under vacuum to remove 812 L (7.0 rel. vol.) of solvent. The reaction mixture was adjusted to a temperature of 65° C. to 70° C., water (116 L, 1.0 rel. vol.) was added, and the mixture stirred at a temperature of 65° C. to 70° C. for 12 hours. Toluene (232 L, 2.0 rel. vol.), and then water (928 L, 8.0 rel. vol.), were charged at a temperature of 65° C. to 70° C. The mixture was then cooled to 20° C. and filtered. The filter cake was washed four times with water (464 L, 4.0 rel. vol.) and dried at 50° C. to yield a white crystalline solid [4-(2-pyridylcarbamoyl)phenyl]-boronic acid (Compound (V), 141.8 kg, 83.8% theory).

Example 11: Preparation of [4-(2-Pyridylcarbamoyl)phenyl]boronic acid (Compound (V))

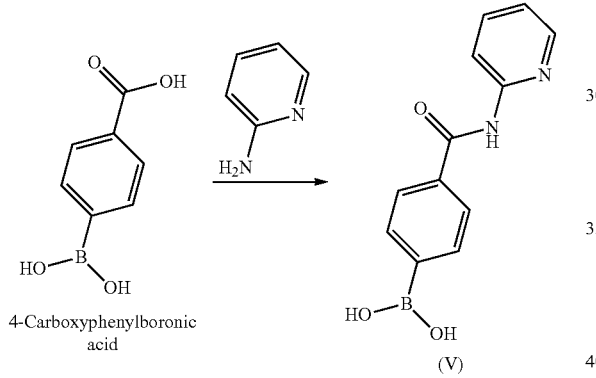

The synthesis described in Example 10 was further modified, inter alia, to identify a suitable replacement solvent for N,N-dimethylformamide that would reduce the potential formation of undesirable by-products, particularly dimethylcarbamoyl chloride.

4-Carboxyphenylboronic acid (7.0 g, 1.0 mol. eq.) was mixed with toluene (66.5 ml, 9.5 rel. vol.) and tetrabutylammonium chloride (0.59 g, 0.05 mol. eq.) at 50° C. Thionyl chloride (13.8 g, 2.75 mol. eq.) was charged slowly to the slurry, followed by a linewash of toluene (3.5 ml, 0.5 rel. vol.). The reaction was heated to 70° C. and agitated for at least six hours before being cooled. The mixture was then concentrated under vacuum to approximately 4.0 rel. vol., and then pyridine (56 ml, 8.0 rel. vol.) was added. The mixture was then concentrated under vacuum to approximately 4.0 rel. vol. and then added to a solution of 2-aminopyridine (7.94 g, 2.0 mol. eq.) in pyridine (35 ml, 5.0 rel. vol.), followed by a pyridine (7 ml, 1.0 rel. vol.) linewash. The reaction was slowly heated to 70° C. and agitated for at least 18 hours. The mixture was then concentrated under vacuum to approximately 3.0 rel. vol. Water (7 ml, 1.0 rel. vol.) was added, and the mixture stirred at 70° C. for at least one hour. Water (56 ml, 8.0 rel. vol.) was charged at 70° C. The mixture was then cooled to 20° C. and filtered. The filter cake was washed four times with water (28 ml, 4.0 rel. vol.) and dried at 50° C. to yield a white crystalline solid [4-(2-pyridylcarbamoyl)phenyl]-boronic acid (Compound (V), 8.79 kg, 85% theory).

This compound exists as a mixture of conformers in solution and resonances are quoted for the major conformer only. 1H NMR (500 MHz, DMSO-d6) δ 7.16 (ddd, J=7.2, 4.9, 0.9 Hz, 1H), 7.83 (ddd, J=8.3, 7.2, 1.9 Hz, 1H), 7.87-7.90 (m, 2H), 7.95-7.99 (m, 2H), 8.17-8.20 (m, 1H), 8.24 (br s, 2H), 8.38 (ddd, J=4.9, 1.9, 0.8 Hz, 1H), 10.74 (s, 1H). 13C NMR (126 MHz, DMSO-d6) δ 114.7, 119.8, 126.8, 134.0, 135.3, 138.1, 138.3, 147.9, 152.2, 166.1.

Example 12: Preparation of 4-{8-amino-3-[(2S)-2-pyrrolidinyl]imidazo[1,5-a]pyrazin-1-yl}-N-(2-pyridinyl)benzamide (Compound (VII))

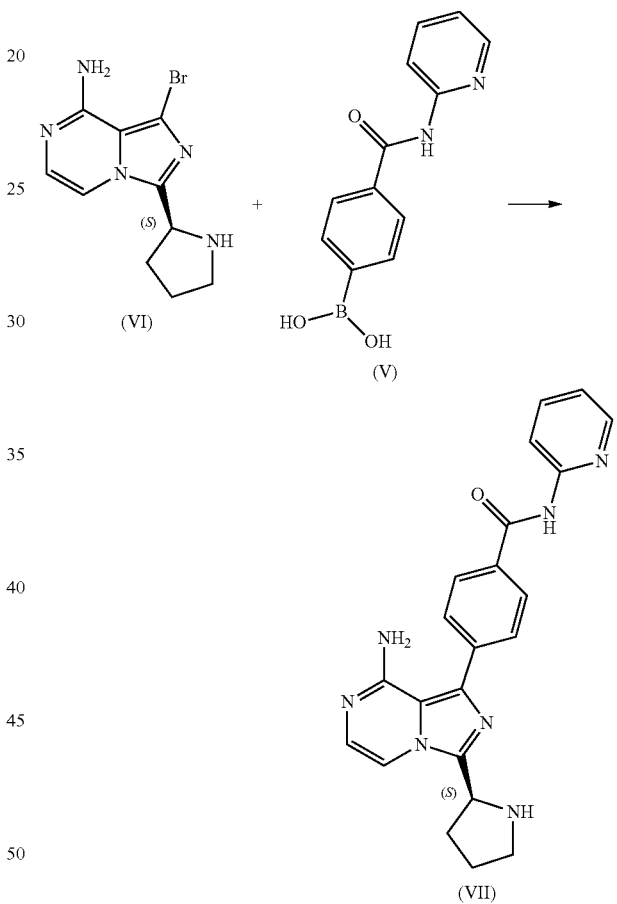

1-Bromo-3-[(2S)-2-pyrrolidinyl]imidazo[1,5-a]pyrazin-8-amine (Compound (VI), 49.7 kg, 1.00 mol. eq.) and [4-(2-pyridylcarbamoyl)phenyl]boronic acid (Compound (V), 44.7 kg, 1.05 mol. eq.) were mixed in water (422 L, 8.45 rel. vol.) and 2-butanol (184 L, 4.55 rel. vol.) with bis(tert-butyldicyclohexylphosphine) dichloropalladium(II) (0.61 kg, 0.005 mol. eq.), potassium iodide (9.0 kg, 0.30 rel. vol.) and triethylamine (54 kg, 3.0 mol. eq.). The reaction mixture was then heated to 82° C. for at least 24 hours under nitrogen. The reaction mixture was slowly cooled to approximately 23° C. then heat cycled by warming to about 42° C., cooling to about 23° C. and warming to about 42° C.

Water (727 L, 15 rel. vol.) was then slowly added and the mixture cooled to approximately 20° C., before filtering and washing with water. Filtration and washing cycles were extremely slow. During processing, two filters and multiple discharges were required taking typically 3 to 4 days to complete. X-ray powder diffraction of the material isolated in this filtration step gave a diffractogram consistent with that of FIG. 2 (i.e., Type 2). The water wet product was further dried by refluxing in heptane (964 L) under Dean-Stark conditions for 29 hours, and then filtered and dried at 45° C. under vacuum to yield a yellow crystalline solid 4-{8-amino-3-[(2S)-2-pyrrolidinyl]-imidazo[1,5-a]pyrazin-1-yl}-N-(2-pyridinyl)benzamide (Compound (VII), 61.6 kg, 81.5%).

Example 13: Preparation of 4-{8-amino-3-[(2S)-2-pyrrolidinyl]imidazo[1,5-a]pyrazin-1-yl}-N-(2-pyridinyl)benzamide (Compound (VII))

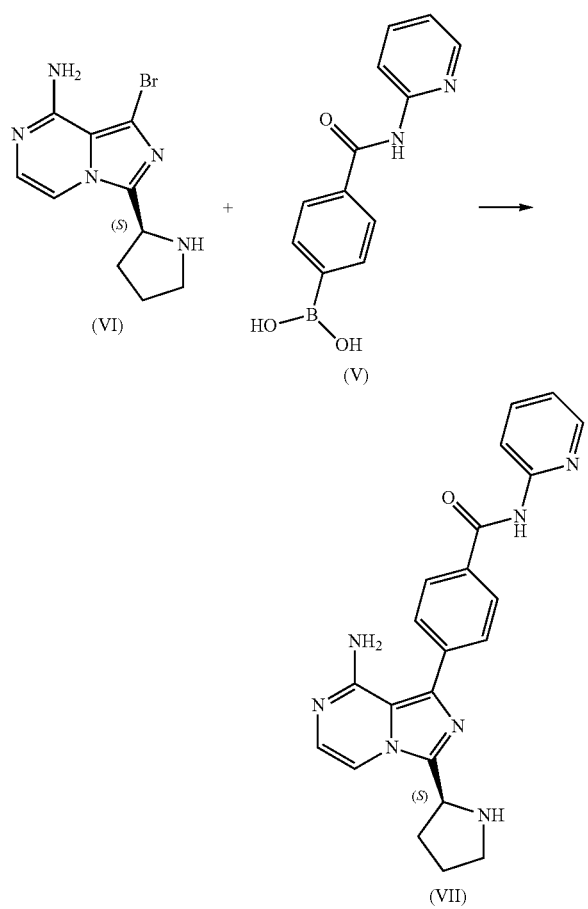

The synthesis described in Example 12 was further modified, inter alia, to improve filtration of the crude product and reduce cycle time for the synthesis.

1-Bromo-3-[(2S)-2-pyrrolidinyl]imidazo[1,5-a]pyrazin-8-amine (Compound (VI), 26.5 kg, 1.00 mol. eq.) and [4-(2-pyridylcarbamoyl)phenyl]boronic acid (Compound (V), 25 kg, 1.10 mol. eq.) were mixed in water (224 L, 8.45 rel. vol.) and 2-butanol (120 L, 4.55 rel. vol.) with bis(tert-butyldicyclohexylphosphine) dichloropalladium(II) (0.64 kg, 0.01 mol. eq.), potassium iodide (4.7 kg, 0.30 rel. vol.), and triethylamine (28.9 kg, 1.50 mol. eq.). The reaction mixture was then heated to 82° C. for 15 hours. The reaction mixture was diluted with 2-butanol (149 L, 5.6 rel. vol.), water (11 L, 0.4 rel. vol.) and 3M aqueous potassium carbonate (53 L, 2.0 rel. vol.) at 75° C. to 82° C. and the aqueous layer removed and discarded. The organic layer was treated with QuadraSil MP (5.3 kg, 0.20 rel. wt.) at 80° C. for 18 hours. The scavenger was removed by filtration at 80° C., and washed with 2-butanol (27 L, 1.0 rel. vol.). The organic mixture was washed with a solution of water (56 L, 2.1 rel. vol.) and 3M aqueous potassium carbonate (9 L, 0.33 rel. vol.) at a temperature of 75° C. to 82° C., and then washed with water (55 L, 2.0 rel. vol.) at a temperature of 75° C. to 82° C. 2-Butanol was added to adjust the volume of the solution to 16 rel. vol. and the mixture was distilled at atmospheric pressure while maintaining a constant volume of about 16 rel. vol. in the vessel by the addition of further 2-butanol, until the mixture reached a temperature above 97° C. The mixture was seeded with crystalline 4-{8-amino-3-[(2S)-2-pyrrolidinyl]imidazo[1,5-a]pyrazin-1-yl}-N-(2-pyridinyl)benzamide (Compound (VII), 0.13 kg, 0.005 rel. wt.) and further distilled at atmospheric pressure to reduce the volume to about 10 rel. vol. The mixture was slowly cooled to 20° C., then filtered and washed with 2-butanol (106 L, 4.0 rel. vol.), then 2-butanol (53 L, 2.0 rel. vol.) followed by heptane (53 L, 2.0 rel. vol.), and dried at 45° C. under vacuum to yellow crystalline solid 4-{8-amino-3-[(2S)-2-pyrrolidinyl]imidazo[1,5-a]pyrazin-1-yl}-N-(2-pyridinyl)benzamide (Compound (VII), 26.8 kg, 75%). Filtration and washing cycles were achieved in less than 24 hours using a single discharge on one filter.

The solid 4-{8-amino-3-[(2S)-2-pyrrolidinyl]imidazo[1,5-a]pyrazin-1-yl}-N-(2-pyridinyl)benzamide (Compound (VII), 40.6 kg, 1.0 mol. eq.) was purified by slurrying in 1M aqueous potassium carbonate solution (162.4 L, 4.0 rel. vol.) to remove the impurity 4-[8-amino-3-[(2S)-pyrrolidin-2-yl]imidazo[1,5-a]pyrazin-1-yl]benzoic acid (Compound (XII)) followed by filtration and washing with water (81.2 L, 2.0 rel. vol.) and then heptane (81.2 L, 2.0 rel. vol.) to yield yellow crystalline 4-{8-amino-3-[(2S)-2-pyrrolidinyl]imidazo[1,5-a]pyrazin-1-yl}-N-(2-pyridinyl)benzamide (Compound (VII), 39.7 kg, 98%). In addition to the 4-[8-amino-3-[(2S)-pyrrolidin-2-yl]imidazo[1,5-a]pyrazin-1-yl]benzoic acid (Compound (XII)) impurity, another impurity, 4-[8-amino-3-[(2S)-1-[4-[8-amino-3-[(2S)-pyrrolidin-2-yl]imidazo[1,5-a]pyrazin-1-yl]benzoyl]pyrrolidin-2-yl]imidazo[1,5-a]pyrazin-1-yl]-N-(2-pyridyl)benzamide (Compound (XIII)), was observed and was not removed by this rework.

Example 14: Preparation of 4-{8-amino-3-[(2S)-2-pyrrolidinyl]imidazo[1,5-a]pyrazin-1-yl}-N-(2-pyridinyl)benzamide (Compound (VII))

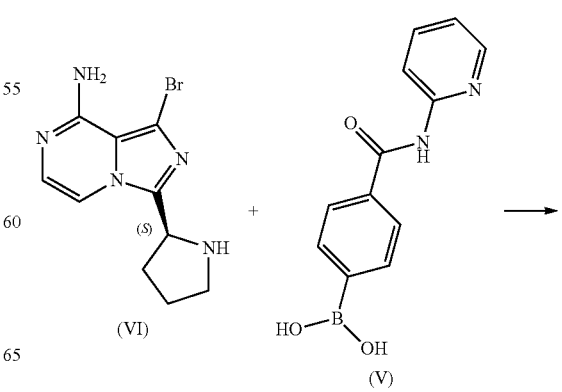

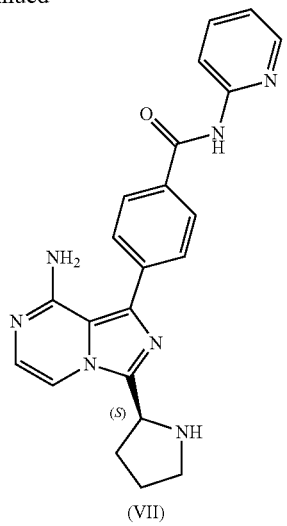

(VII)

Although the process described in Example 13 resulted in improved filtration and cycle time, two undesired impurities formed due to prolonged heating under the process conditions. Therefore, the process was further modified, inter alia, to reduce the formation of these impurities and improve the purity of the final product.

1-Bromo-3-[(2S)-2-pyrrolidinyl]imidazo[1,5-a]pyrazin-8-amine (Compound (VI), 115.0 kg, 1.00 mol. eq.) and [4-(2-pyridylcarbamoyl)phenyl]boronic acid (Compound (V), 96.7 kg, 0.98 mol. eq.) were mixed in water (920 L, 8.0 rel. vol.) and 2-butanol (978 L, 8.5 rel. vol.) with bis(tert-butyldicyclohexylphosphine)dichloropalladium(II) (2.8 kg, 0.01 mol. eq.), potassium iodide (20.3 kg, 0.30 mol. eq.), and potassium carbonate (135.2 kg, 2.40 mol. eq.). The reaction mixture was then heated to 80° C. for 16 hours. The layers were separated and the aqueous layer discarded. The organic layer was diluted with 2-butanol (460 L, 4.0 rel. vol.), washed with water (575 L, 5.0 rel. vol.), then water (460 L, 4.0 rel. vol.) at 60° C. and then treated with QuadraSil MP (23 kg, 0.20 rel. wt.) at 60° C. for 9 hours. The scavenger was removed by filtration at 60° C., and washed with 2-butanol (173 L, 1.5 rel. vol.). The resulting mixture was washed at 60° C. with a solution of sodium chloride (46 kg, 0.40 rel. wt.) in water (230 L, 2.0 rel. vol.). The mixture was seeded with crystalline 4-{8-amino-3-[(2S)-2-pyrrolidinyl]imidazo[1,5-a]pyrazin-1-yl}-N-(2-pyridinyl)-benzamide (Compound (VII), 1.15 kg, 0.01 rel. wt.) before being distilled under vacuum (0.2 bar) while maintaining a constant volume of 1840 L (16 rel. vol.) in the vessel by the addition of further 2-butanol (1610 L, 14.0 rel. vol.), and maintaining a temperature below 60° C. The mixture was then distilled (at 0.2 bar) to a volume of 1380 L (12.0 rel. vol.), maintaining a temperature below 60° C. Heated to 80° C. for two hours, then cooled to 20° C. and filtered. The product was washed with 2-butanol (460 L, 4.0 rel. vol.), then 2-butanol (230 L, 2.0 rel. vol.) followed by heptane (230 L, 2.0 rel. vol.), and dried at 45° C. under vacuum to a yellow crystalline solid 4-{8-Amino-3-[(2S)-2-pyrrolidinyl]-imidazo[1,5-a]pyrazin-1-yl}-N-(2-pyridinyl)-benzamide (Compound VII, 131.7 kg, 80.4%). Filtration and washing cycles were achieved in less than 24 hours using a single discharge, and one filter.

1H NMR (500 MHz, DMSO-d6) δ 1.71-1.80 (m, 1H), 1.83-1.92 (m, 1H), 2.06-2.14 (m, 1H), 2.22-2.30 (m, 1H), 2.89 (t, J=6.8 Hz, 2H), 4.55 (t, J=7.2 Hz, 1H), 6.11 (br s, 2H), 7.07 (d, J=5.0 Hz, 1H), 7.17 (ddd, J=7.4, 4.9, 0.9 Hz, 1H), 7.72-7.75 (m, 2H), 7.77 (d, J=5.0 Hz, 1H), 7.85 (ddd, J=8.4, 7.4, 2.0 Hz, 1H), 8.13-8.16 (m, 2H), 8.20-8.23 (m, 1H), 8.39 (ddd, J=4.9, 2.0, 0.9 Hz, 1H), 10.82 (br s, 1H). 13C NMR (126 MHz, DMSO-d6) δ 25.8, 29.5, 46.6, 54.2, 107.4, 114.6, 114.7, 119.8, 127.5, 128.3, 129.0, 132.3, 132.6, 138.1, 138.1, 142.8, 148.0, 151.5, 152.2, 165.7. X-ray Powder diffraction of the crystalline solid obtained gave a diffractogram consistent with that of FIG. 4 (i.e., Form C).

Example 15: X-Ray Powder Diffraction Analysis of 4-{8-Amino-3-[(2S)-2-pyrrolidinyl]imidazo[1,5-a]pyrazin-1-yl}-N-(2-pyridinyl)benzamide (Compound (VII))

A. Analytical Protocol

Crystalline samples of Type 2, Type 3, and Form C of 4-{8-Amino-3-[(2S)-2-pyrrolidinyl]imidazo[1,5-a]pyrazin-1-yl}-N-(2-pyridinyl)benzamide (Compound (VII)) were analyzed by X-ray powder diffraction. Samples were mounted on a silicon wafer mount and analyzed using the PANalytical CubiX PRO diffractometer (λ=1.5418 Å). Samples were measured in reflection geometry in θ-θ configuration over the scan range 2° to 40° 2θ with a nominal 25 second exposure per 0.020 increment. The X-rays were generated by a copper long-fine focus tube operated at 45 kV and 40 mA. Results for crystalline Type 2, Type 3, and Form C are reported below in subsections A, B, and C, respectively.

B. Analysis of Crystal Form Type 2

A sample of Type 2 crystalline 4-{8-Amino-3-[(2S)-2-pyrrolidinyl]imidazo[1,5-a]pyrazin-1-yl}-N-(2-pyridinyl)benzamide (Compound (VII)) was analyzed by X-ray powder diffraction. The resulting X-ray diffraction pattern is shown in FIG. 2 with selected peaks and relative intensities reported in Table 6 below.

TABLE 6

| PEAK | RELATIVE INTENSITY |
|---|---|
| 5.0 | 32 |
| 5.7 | 32 |
| 7.2 | 100 |
| 9.0 | 19 |
| 9.9 | 80 |
| 10.3 | 16 |
| 10.6 | 13 |
| 11.2 | 83 |
| 12.7 | 15 |
| 13.4 | 8 |
| 14.1 | 13 |
| 14.9 | 75 |
| 15.6 | 21 |
| 16.2 | 18 |
| 17.2 | 6 |
| 18.1 | 21 |
| 18.3 | 13 |
| 18.6 | 9 |
| 19.1 | 15 |
| 19.5 | 21 |
| 19.8 | 28 |
| 20.2 | 30 |
| 20.7 | 20 |

The Type 2 crystalline form exhibits characteristic peaks at 5.0, 5.7, 7.2, 9.0, 9.9, 11.2, 12.7, 14.1 and 14.9±0.2 °2θ, particularly peaks at 5.0, 5.7, 7.2, 9.9, and/or 11.2±0.2 °2θ. As previously noted, the product isolated from the first filtration of Example 12 corresponds to the Type 2 crystalline form.

C. Analysis of Crystal Form Type 3

A sample of Type 3 crystalline 4-{8-Amino-3-[(2S)-2-pyrrolidinyl]imidazo[1,5-a]pyrazin-1-yl}-N-(2-pyridinyl)benzamide (Compound (VII)) produced by slurrying Type 2 in pure butanol for 7 days at ambient conditions was analyzed by X-ray powder diffraction. The resulting X-ray diffraction pattern is shown in FIG. 3 with selected peaks and relative intensities reported in Table 7 below.

TABLE 7

| PEAK | RELATIVE INTENSITY |
| --- | --- |
| 4.8 | 21 |
| 5.8 | 8 |
| 7.4 | 51 |
| 7.7 | 27 |
| 9.6 | 15 |
| 9.9 | 7 |
| 11.1 | 11 |
| 11.7 | 43 |
| 12.5 | 100 |
| 12.8 | 26 |
| 14.1 | 22 |
| 14.7 | 8 |
| 15.3 | 30 |
| 15.8 | 10 |
| 16.9 | 11 |
| 17.6 | 5 |
| 18.9 | 25 |
| 19.7 | 16 |
| 21.6 | 38 |
| 22.0 | 19 |
| 22.3 | 43 |
| 22.8 | 15 |
| 23.8 | 11 |
| 25.7 | 7 |
| 28.8 | 6 |

The Type 3 crystalline form exhibits characteristic peaks at 4.8, 7.4, 7.7, 9.6, 11.7, 12.5, 12.8, 15.3, 22.3, and/or 21.6±0.2 °2θ, particularly peaks at 7.4, 11.7, 12.5, 22.3, and/or 21.6±0.2 °2θ.

D. Analysis of Crystal Form C

A sample of Form C crystalline 4-{8-Amino-3-[(2S)-2-pyrrolidinyl]imidazo[1,5-a]pyrazin-1-yl}-N-(2-pyridinyl)benzamide (Compound (VII)) was analyzed by X-ray powder diffraction. The resulting X-ray diffraction pattern is shown in FIG. 4 with selected peaks and relative intensities reported in Table 8 below.

TABLE 8

| PEAK | RELATIVE INTENSITY |
| --- | --- |
| 7.4 | 1 |
| 8.9 | 1 |
| 9.9 | 7 |
| 11.1 | 11 |
| 12.8 | 37 |
| 14.1 | 100 |
| 14.8 | 21 |
| 15.2 | 11 |
| 15.8 | 13 |
| 17.0 | 22 |
| 17.6 | 15 |
| 17.8 | 23 |
| 19.0 | 46 |
| 19.5 | 10 |
| 19.9 | 17 |
| 20.9 | 13 |
| 21.6 | 99 |
| 22.1 | 33 |
| 22.9 | 82 |

TABLE 8-continued

| PEAK | RELATIVE INTENSITY |
| --- | --- |
| 23.9 | 15 |
| 24.8 | 29 |

The Form C crystalline form exhibits characteristic peaks at 7.4, 8.9, 9.9, 11.1, 12.8, 14.1, 14.8, 19.0, and/or 21.6±0.2 °2θ, particularly peaks at 9.9, 11.1, 12.8, 14.1, and 19.0±0.2 °2θ. As previously noted, the product isolated from the filtration of Example 14 corresponds to the Form C crystalline form.

Example 16: Preparation of 4-{8-amino-3-[(2S)-1-(but-2-ynoyl)pyrrolidin-2-yl]imidazo[1,5-a]pyrazin-1-yl}-N-(pyridin-2-yl)benzamide (Compound (VIII))

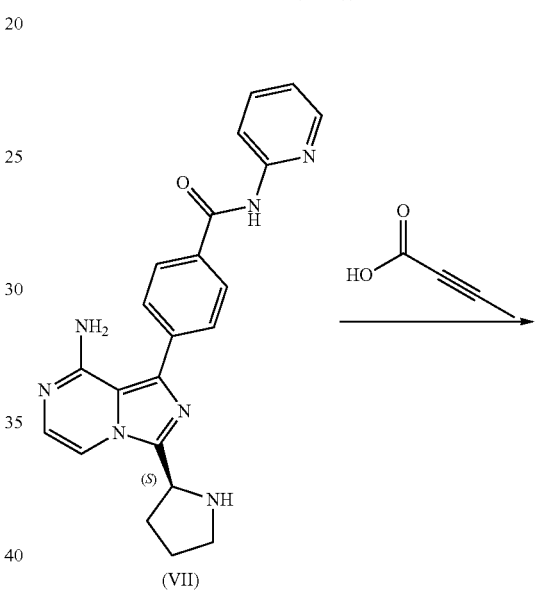

(VII)

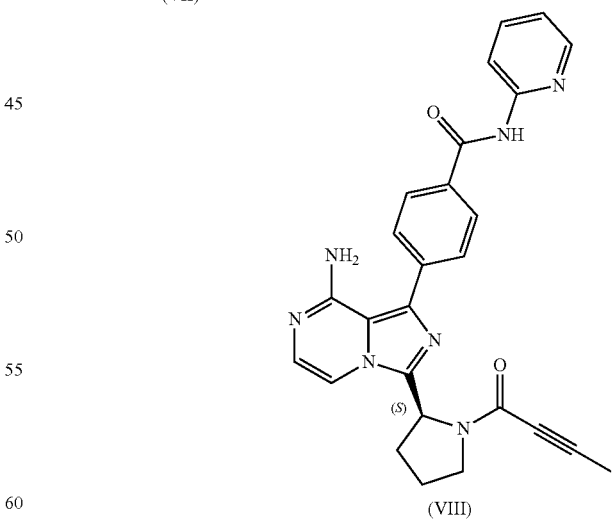

(VIII)

4-{8-Amino-3-[(2S)-2-pyrrolidinyl]imidazo[1,5-a]pyrazin-1-yl}-N-(2-pyridinyl)-benzamide (Compound (VII), 70 kg, 1.0 mol. eq.) and 2-butynoic acid (17.5 kg, 1.2 mol. eq.) were mixed in dichloromethane (1537 kg, 22 rel. vol.) to give a thick slurry. Triethylamine (44.5 kg, 2.5 mol.

eq.) was added, followed by 1-propylphosphonic acid anhydride (T3P) (approximately 111.4 kg, 1.0 mol. eq.) (Further aliquots of T3P were added portionwise until the reaction was deemed complete). The resulting organic solution of the product was washed twice with water (525 kg, 7.5 rel. vol.) and then concentrated to about 2 to 3 rel. vol. Water (700 kg, 10.0 rel. vol.) was added, and the mixture was then acidified using 6M aqueous hydrochloric acid to reach approximately pH 2 before separating the organic phase, which was discarded. The aqueous layer, (containing the product) was washed three times with 2-methyltetrahydrofuran (478 kg, 8.0 rel. vol.), then twice more with 2-methyltetrahydrofuran (180 kg, 3.0 rel. vol.). Dichloromethane (742 kg, 8.0 rel. vol.) was added to the aqueous phase and the mixture was adjusted to a pH of 7.0 to 8.5 with triethylamine (variable amount) to extract the product into the organic phase. The organic phase was separated off and washed twice with water (350 kg, 5.0 rel. vol.), then filtered through carbon, then repeatedly treated with Quadrasil-MP (17.5 kg, 0.25 rel. wt.), washing the spent scavenger cake with methanol each time, until the palladium specification was met. Concentrated the filtrates to 5 rel. vol. Added ethanol (276 kg, 5 rel. vol.) and concentrated to 5 rel. vol., and repeated this operation a further two times. The mixture was then heated to 50° C., cooled to 20° C., and filtered. The product was washed twice with ethanol (55 kg, 1.0 rel. vol.) and then the wet cake returned to the vessel and dissolved in methanol (831 kg, 15 rel. vol.) at 60° C. Concentrated the filtrates to 5 rel. vol. Added ethanol (276 kg, 5 rel. vol.) and concentrated to 5 rel. vol. and repeated once. The mixture was then heated to 50° C., cooled to 20° C., and filtered. The product was washed twice with ethanol (55 kg, 1.0 rel. vol.) and then dried at 50° C. under vacuum to yield white crystalline solid acalabrutinib (Compound VIII, 52.2 kg, 64%).

Example 17: Preparation of 4-{8-amino-3-[(2S)-1-(but-2-ynoyl)pyrrolidin-2-yl]imidazo[1,5-a]pyrazin-1-yl}-N-(pyridin-2-yl)benzamide (Compound (VIII))

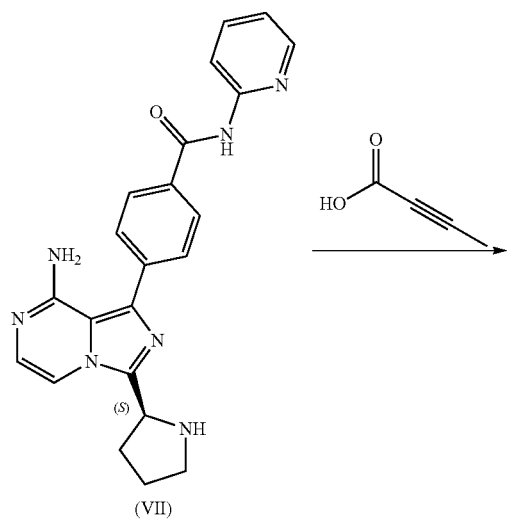

(VII)

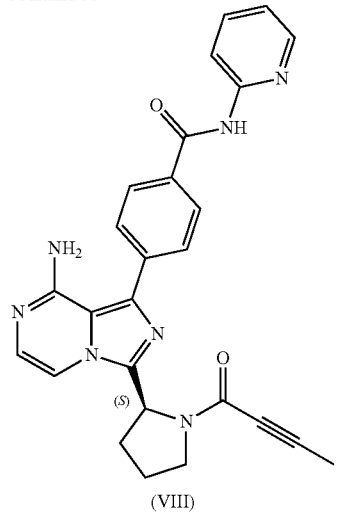

(VIII)

The synthesis described in Example 17 was further modified, inter alia, to allow for greater flexibility in the operating conditions while still yielding a product having appropriate purity. Among other advantages, the modified synthesis results in an improvement in the removal of certain impurities.

4-{8-Amino-3-[(2S)-2-pyrrolidinyl]imidazo[1,5-a]pyrazin-1-yl}-N-(2-pyridinyl)-benzamide (Compound (VII), 131.7 kg, 1.0 mol. eq.) was slurried in dichloromethane (955 L, 7.25 rel. vol.) and triethylamine (90.1 kg, 2.7 mol. eq.). 2-butynoic acid (33.3 kg, 1.2 mol. eq.) in dichloromethane (263.4 L, 2.0 rel. vol.) was added, followed by 1-propylphosphonic acid anhydride (T3P) (50% w/w solution in dichloromethane, 209.8 kg, 1.0 mol. eq.). The resulting organic solution of the product was washed twice with water (658.5 L, 5.0 rel. vol.) and then water (1317 L, 10.0 rel. vol.) was added. The mixture was then acidified using 6M aqueous hydrochloric acid to approximately pH 2.2 and then 2M aqueous hydrochloric acid added to reach a pH of 1.8 to 2.2 before separating the organic phase, which was discarded. Dichloromethane (1317 L, 10.0 rel. vol.) was added to the aqueous phase and the mixture is adjusted to a pH of 4.5 to 5.0 with triethylamine. The organic phase was separated off and the aqueous phase was re-extracted with dichloromethane (527 L, 4.0 rel. vol.). The combined dichloromethane extracts were screened and the organic phase was concentrated to approximately 5.0 rel. vol. Ethanol (1712 L, 13.0 rel. vol.) was added and the mixture distilled (at about 360 mbar) maintaining a constant volume (of 18.0 rel. vol.) by the addition of ethanol (1580 L, 12.0 rel. vol.). A portion of crystalline 4-{8-amino-3-[(2S)-1-(but-2-ynoyl)pyrrolidin-2-yl]imidazo[1,5-a]pyrazin-1-yl}-N-(pyridin-2-yl)benzamide (Compound (VIII), 1.32 kg, 0.01 rel. wt.) was added as seed, and the solution held at 50° C. for 10 hours to crystallize the product. The mixture was then cooled over 7 hours and filtered. The product was washed twice with ethanol (527 L, 4.0 rel. vol.) and then dried at 50° C. under vacuum to yield a white crystalline solid acalabrutinib (Compound VIII, 113.6 kg, 74%).

This compound exists as a mixture of conformers in solution and resonances are quoted for the major conformer only. 1H NMR (500 MHz, DMSO-d6) δ 1.95-2.02 (m, 4H), 2.09-2.15 (m, 1H), 2.23-2.38 (m, 2H), 3.81 (t, J=6.7 Hz, 2H), 5.47 (dd, J=7.6, 4.3 Hz, 1H), 6.13 (br s, 2H), 7.11 (d, J=5.1 Hz, 1H), 7.17 (ddd, J=7.4, 4.8, 0.8 Hz, 1H), 7.70-7.73

(m, 2H), 7.78 (d, J=5.1 Hz, 1H), 7.82-7.87 (m, 1H), 8.13-8.16 (m, 2H), 8.20-8.23 (m, 1H), 8.39 (ddd, J=4.8, 1.9, 0.8 Hz, 1H), 10.83 (s, 1H). 13C NMR (126 MHz, DMSO-d6) δ 3.3, 23.9, 31.2, 48.2, 51.3, 74.3, 88.3, 107.0, 113.8, 114.7, 119.8, 127.9, 128.3, 129.0, 132.7, 133.2, 137.9, 138.1, 141.0, 148.0, 151.4, 151.8, 152.2, 165.7.

Example 18: Preparation of Benzyl (2S)-2-[(3-chloropyrazin-2-yl)methyl-carbamoyl]pyrrolidine-1-carboxylate (Compound (I))

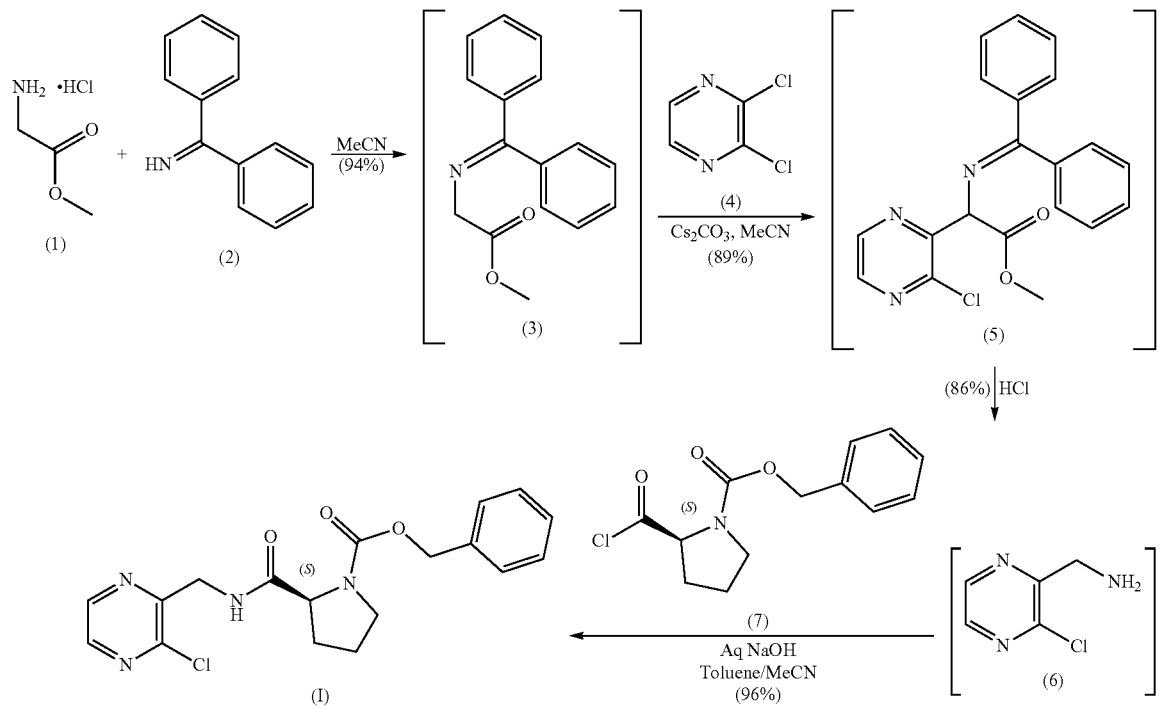

A. Preparation of Compound (7)

To a solution of (2S)-1-benzyloxycarbonylpyrrolidine-2-carboxylic acid (1.039 kg, 1.0 mol. Eq.) and toluene (6.3 L, 6.0 rel. vol.), was added thionyl chloride (0.75 kg, 1.5 mol. Eq.), and the mixture was stirred at 30° C. for 7 hours. The reaction mixture was concentrated (to approximately 4.5 rel. vol.) at 35° C. to 45° C. under vacuum. Toluene (2.1 L, 2.0 rel. vol.) was added, and the reaction mixture concentrated (to approximately 4.5 rel. vol.) at 35° C. to 45° C. under vacuum. The assay of the solution of the product (Compound (7)) was tested (5.6 kg @ 18.3% w/w=1.03 kg, 91.8% yield).

B. Preparation of Benzyl (2S)-2-[(3-chloropyrazin-2-yl)methylcarbamoyl]-pyrrolidine-1-carboxylate (Compound (I))

Step 1: Diphenylmethanimine (Compound (1), 1.44 kg, 1.0 mol. eq.) and glycine methyl ester hydrochloride (Compound (2), 1.099 kg, 1.1 mol. eq.) were mixed in acetonitrile (7.2 L, 5.0 rel. vol.) at 35° C. to 40° C. for 3 hours. Cooled to 20° C. to 25° C. and filtered, washing the cake twice with acetonitrile (2.88 L, 2.0 rel. vol.). The assay of the solution of the product (Compound (3)) was measured (10.05 kg @ 18.9% w/w=1.9 kg, 94.4% yield).

Step 2: 2,3-dipyrazine (Compound (4), 0.911 kg, 1.0 mol. eq.) and cesium carbonate (2.39 kg, 1.2 mol. eq.) were added to the filtrate solution (10.05 kg @ 18.9% w/w=1.9 kg, 1.2 mol. eq.) and the mixture was heated to 80° C. to 85° C. for 13 hours. Cooled to 20° C. to 25° C. to filter, washing the cake twice with acetonitrile (1.8 L, 2.0 rel. vol.). The assay of the solution of the product (Compound (5)) was measured (14.7 kg @ 13.3% w/w=1.96 kg, 89.0% yield).

Step 3: Water (3.6 kg, 2.0 rel. vol.) was added into the acetonitrile solution of Compound (5) (13.5 kg @ 13.3% w/w=1.8 kg), and the mixture was distilled under vacuum to 2.5 rel. vol. Further water (3.6 kg, 2.0 rel. vol.) was added and the mixture was distilled under vacuum to 3.5 rel. vol. Added concentrated hydrochloric acid (1.8 L, 1.0 rel. vol. to amount of Compound (5)) and heated to 80° C. to 85° C. for 7 hours. Cooled to 20° C., and washed the aqueous phase with a mixture of toluene (5.4 L, 3.0 rel. vol.) and acetonitrile (3.6 L, 2.0 rel. vol.), then further washed with toluene (5.4 L, 3.0 rel. vol.). The assay of the water phase, containing Compound (6) was measured (10.25 kg @ 5.9% w/w=0.605 kg, 85.8% yield).

Step 4: To a solution of Compound (6) (6.1 kg @ 5.9% w/w=0.36 kg, 1.0 mol. eq.), was added 25% aqueous NaOH solution (to approximately pH=8-9). Added toluene (1.8 L, 5.0 rel. vol.) and Compound (7) (in toluene) solution (4.4 kg @ 18.3% w/w=0.805 kg, 1.2 mol. eq.) at 10° C. to 15° C., (whilst charging 25% aqueous sodium hydroxide solution into the reaction mixture to maintain pH at 8 to 9). Stirred for three hours, and extracted with a mixture of toluene (1.8 L, 5.0 rel. vol.) and acetonitrile (1.44 L, 4.0 rel. vol.), then separated and extracted the water phase with a mixture of toluene (1.8 L, 5.0 rel. vol.) and acetonitrile (0.72 L, 2.0 rel. vol.). The organic phases were combined and washed with brine (1.8 L, 5.0 rel. vol.) and then water (1.8 L, 5.0 rel. vol.).

Concentrated the organic phase (to about 5.0 rel. vol.) at 40° C. to 45° C. under vacuum and heated the mixture to 60° C. Stirred for 15 minutes to achieve a solution, before cooling the mixture to 50° C. Added methyl tert-butyl ether (1.6 L, 4.4 rel. vol.) into the mixture drop-wise until a suspension was observed. Cooled the mixture to 5° C. to 10° C. for 3 hours and stirred for 12 hours. Filtered, and dried the wet cake (at 45° C.) to isolate the product (Compound (I), (920.0 g, 96.3%) (72% yield from 2,3-dipyrazine). This compound exists as a mixture of conformers in solution and resonances are quoted for the major conformer only. $^1$H NMR (500 MHz, DMSO-d$_6$) δ 1.75-1.85 (m, 2H), 1.87-1.93 (m, 1H), 2.12-2.21 (m, 1H), 3.34-3.40 (m, 1H), 3.42-3.48 (m, 1H), 4.29 (dd, J=8.6, 3.5 Hz, 1H), 4.43 (dd, J=16.2, 5.4 Hz, 1H), 4.49 (dd, J=16.2, 5.4 Hz, 1H), 4.98 (d, J=13.0 Hz, 1H), 5.04 (d, J=13.0 Hz, 1H), 7.24-7.31 (m, 5H), 8.39 (d, J=2.4 Hz, 1H), 8.49 (t, J=5.4 Hz, 1H), 8.53 (d, J=2.4 Hz, 1H). $^{13}$C NMR (126 MHz, DMSO-d$_6$) δ 23.0, 31.2, 41.4, 47.1, 59.5, 65.7, 126.9, 127.5, 128.1, 137.0, 142.6, 142.7, 147.1, 151.5, 153.8, 172.3.

XV. SELECTED EMBODIMENTS

Embodiment 1. A process for preparing a compound having the structure of Formula (VIII):

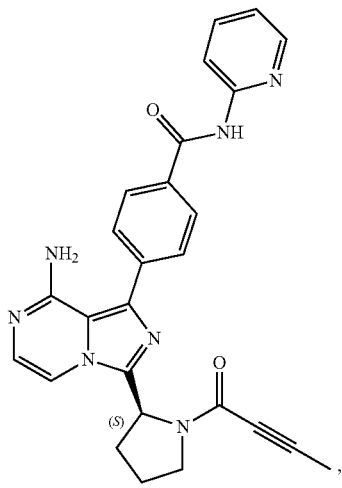

(VIII)

or a salt thereof, wherein the process comprises:
contacting a compound having the structure of Formula (VII):

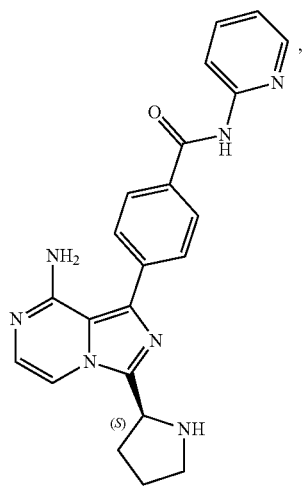

(VII)

or a salt thereof, with 2-butynoic acid, or a salt thereof, in the presence of 1-propylphosphonic anhydride and a base in a reaction medium to form a reaction mixture comprising the compound of Formula (VIII), or salt thereof, and one or more reaction by-products; and selectively isolating the compound of Formula (VIII), or salt thereof, from the reaction mixture relative to the one or more reaction by-products.

Embodiment 2. The process of Embodiment 1, wherein the contacting step comprises:

adding the compound of Formula (VII), or salt thereof, and the base to the reaction medium;

adding the 2-butynoic acid, or salt thereof, to the reaction medium comprising the compound of Formula (VII), or salt thereof, and the base; and adding the 1-propylphosphonic anhydride to the reaction medium comprising the compound of Formula (VII), or salt thereof; 2-butynoic acid, or salt thereof; and the base.

Embodiment 3. The process of Embodiment 1 or 2, wherein the process comprises:

contacting a compound having the structure of Formula (VII):

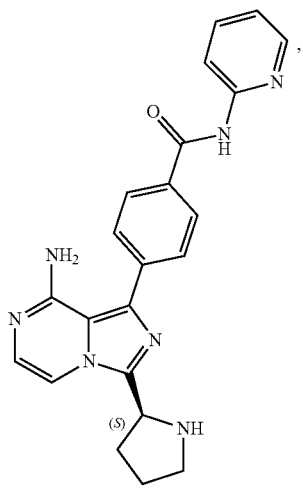

(VII)

or salt thereof, with 2-butynoic acid, or a salt thereof, in the presence of 1-propylphosphonic anhydride and a base in a reaction medium to form a reaction mixture comprising the compound of Formula (VIII), or salt thereof; unreacted compound of Formula (VII), or salt thereof; and a reaction by-product; wherein the reaction by-product comprises a compound having the structure of Formula (XIV):

(XIV)

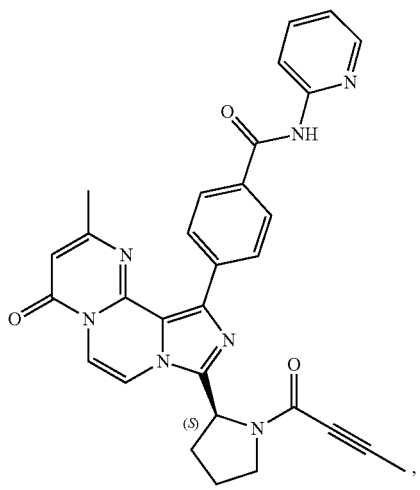

or a salt thereof; and selectively isolating the compound of Formula (VIII), or salt thereof, from the reaction mixture relative to the compound of Formula (VII), or salt thereof, and the compound of Formula (XIV), or salt thereof.

Embodiment 4. The process of Embodiment 1 or 2, wherein the process comprises:

contacting a compound having the structure of Formula (VII):

(VII)

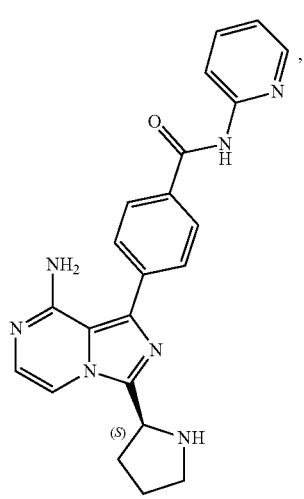

or a salt thereof, with 2-butynoic acid, or salt thereof, in the presence of 1-propylphosphonic anhydride and a base in a reaction medium to form a reaction mixture comprising the compound of Formula (VIII), or salt thereof; unreacted compound of Formula (VII), or salt thereof; and a reaction by-product; wherein the reaction by-product comprises a compound having the structure of Formula (XIV):

(XIV)

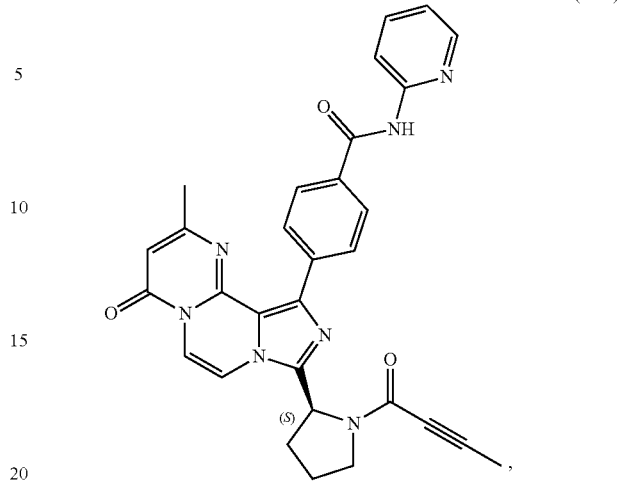

or a salt thereof;

extracting at least a portion of the compound of Formula (VIII), or salt thereof, from the reaction mixture into an aqueous phase, wherein the compound of Formula (VIII), or salt thereof, is selectively extracted into the aqueous phase relative to the compound of Formula (XIV), or salt thereof;

adjusting the pH of the aqueous phase; and extracting at least a portion of the compound of Formula (VIII), or salt thereof, from the aqueous phase into an organic phase, wherein the compound of Formula (VIII), or salt thereof, is selectively extracted into the organic phase relative to the compound of Formula (VII), or salt thereof.

Embodiment 5. The process of Embodiment 3 or 4, wherein the selectively isolated compound of Formula (VIII), or salt thereof, comprises less than about 1.0 weight % of the compound of Formula (VII), or salt thereof.

Embodiment 6. The process of Embodiment 3 or 4, wherein the selectively isolated compound of Formula (VIII), or salt thereof, comprises less than about 1.0 weight % of the compound of Formula (XIV), or salt thereof.

Embodiment 7. The process of Embodiment 3 or 4, wherein the selectively isolated compound of Formula (VIII), or salt thereof, comprises less than about 1.0 weight % of the compound of Formula (VII), or salt thereof, and less than about 1.0 weight % of the compound of Formula (XIV), or salt thereof.

Embodiment 8. The process of any of Embodiments 4 to 7, wherein the reaction mixture is washed with water and the washed reaction mixture separated into the aqueous phase and a discard phase, wherein the compound of Formula (VIII) is selectively extracted into the aqueous phase.

Embodiment 9. The process of any of Embodiments 4 to 8, wherein the process further comprises isolating the compound of Formula (VIII) from the organic phase into which the compound of Formula (VIII) has been selectively extracted.

Embodiment 10. The process of any of Embodiments 4 to 9, wherein the aqueous phase comprises greater than about 75 area % of the compound of Formula (VIII) as measured by high-performance liquid chromatography upon completion of the aqueous phase extraction.

Embodiment 11. The process of any of Embodiments 4 to 9, wherein the aqueous phase comprises less than about 2.0 area % of the compound of Formula (XIV) as measured by high-performance liquid chromatography upon completion of the aqueous phase extraction.

Embodiment 12. The process of any of Embodiments 4 to 9, wherein the aqueous phase comprises greater than about 75 area % of the compound of Formula (VIII) and less than about 2.0 area % of the compound of Formula (XIV) as measured by high-performance liquid chromatography upon completion of the aqueous phase extraction.

Embodiment 13. The process of any of Embodiments 4 to 12, wherein the organic phase comprises at least about 75 area % of the compound of Formula (VIII) as measured by high-performance liquid chromatography upon completion of the organic phase extraction.

Embodiment 14. The process of any of Embodiments 4 to 12, wherein the organic phase comprises less than about 2.0 area % of the compound of Formula (VII) as measured by high-performance liquid chromatography upon completion of the organic phase extraction.

Embodiment 15. The process of any of Embodiments 4 to 12, wherein the organic phase comprises at least about 75 area % of the compound of Formula (VIII) and less than about 2.0 area % of the compound of Formula (VII) as measured by high-performance liquid chromatography upon completion of the organic phase extraction.

Embodiment 16. The process of any of Embodiments 4 to 15, wherein the aqueous phase has a pH less than about 2.5 during the aqueous phase extracting step.

Embodiment 17. The process of any of Embodiments 4 to 15, wherein the aqueous phase has a pH from about 1.8 to about 2.2 during the aqueous phase extracting step.

Embodiment 18. The process of any of Embodiments 4 to 15, wherein the aqueous phase has a pH greater than about 4.0 during the organic phase extracting step.

Embodiment 19. The process of any of Embodiments 4 to 15, wherein the aqueous phase has a pH from about 4.5 to about 5.0 during the organic phase extracting step.

Embodiment 20. The process of any of Embodiments 4 to 19, wherein the reaction medium comprises at least one solvent selected from the group consisting of alkyl hydrocarbons, aromatic hydrocarbons, halogenated hydrocarbons, alcohols, ketones, ethers, esters, nitriles, and polar aprotic solvents.

Embodiment 21. The process of any of Embodiments 4 to 19, wherein the reaction medium comprises at least one solvent selected from the group consisting of dichloromethane, tetrahydrofuran, 2-methyltetrahydrofuran, tert-amyl alcohol, acetone, methyl iso-butyl ketone, 2-butanol, methyl ethyl ketone, acetonitrile, and ethyl acetate.

Embodiment 22. The process of any of Embodiments 4 to 19, wherein the reaction medium comprises dichloromethane.

Embodiment 23. The process of any of Embodiments 4 to 22, wherein the base comprises at least one compound selected from the group consisting of triethylamine, tripropylamine, tributylamine, diisopropylethylamine, N-methylmorpholine, N-methylpyrrolidine, sodium carbonate, sodium bicarbonate, potassium carbonate, and potassium bicarbonate.

Embodiment 24. The process of any of Embodiments 4 to 22, wherein the base comprises triethylamine.

Embodiment 25. The process of any of Embodiments 4 to 24, wherein the organic phase comprises at least one solvent selected from alkyl hydrocarbons, aromatic hydrocarbons, halogenated hydrocarbons, alcohols, ketones, ethers, esters, and nitriles.

Embodiment 26. The process of any of Embodiments 4 to 24, wherein the organic phase comprises at least one compound selected from the group consisting of dichloromethane, methyltetrahydrofuran, and 2-methyltetrahydrofuran, tert-amyl alcohol, methyl iso-butyl ketone, 2-butanol, methyl ethyl ketone, ethyl acetate, isopropylacetate, N-butylacetate, butyronitrile, toluene, xylene, heptane, hexane, isohexane, and chloroform.

Embodiment 27. The process of any of Embodiments 4 to 24, wherein the organic phase comprises dichloromethane.

Embodiment 28. The process of any of Embodiments 4 to 27, wherein the compound of Formula (VII) is contacted with about 0.5 to about 5.0 molar equivalents of 2-butynoic acid relative to the compound of Formula (VII).

Embodiment 29. The process of any of Embodiments 4 to 27, wherein the compound of Formula (VII) is contacted with about 1.0 to about 1.3 molar equivalents of 2-butynoic acid relative to the compound of Formula (VII).

Embodiment 30. The process of any of Embodiments 4 to 27, wherein the compound of Formula (VII) is contacted with about 1.2 molar equivalents of 2-butynoic acid relative to the compound of Formula (VII).

Embodiment 31. The process of any of Embodiments 4 to 30, wherein about 0.3 to about 3.0 molar equivalents of 1-propylphosphonic anhydride are charged to the reaction medium relative to the compound of Formula (VII).

Embodiment 32. The process of any of Embodiments 4 to 30, wherein about 0.5 to about 2.0 molar equivalents of 1-propylphosphonic anhydride are charged to the reaction medium relative to the compound of Formula (VII).

Embodiment 33. The process of any of Embodiments 4 to 30, wherein about 0.7 to about 1.5 molar equivalents of 1-propylphosphonic anhydride are charged to the reaction medium relative to the compound of Formula (VII).

Embodiment 34. The process of any of Embodiments 4 to 30, wherein about 1.0 to about 1.2 molar equivalents of 1-propylphosphonic anhydride are charged to the reaction medium relative to the compound of Formula (VII).

Embodiment 35. The process of any of Embodiments 4 to 34, wherein about 1.0 to about 10.0 molar equivalents of the base are charged to the reaction medium relative to the compound of Formula (VII).

Embodiment 36. The process of any of Embodiments 4 to 34, wherein about 2.0 to about 5.0 molar equivalents of the base are charged to the reaction medium relative to the compound of Formula (VII).

Embodiment 37. The process of any of Embodiments 4 to 34, wherein about 2.4 to about 3.0 molar equivalents of the base are charged to the reaction medium relative to the compound of Formula (VII).

Embodiment 38. The process of Embodiments 4 to 37, wherein the reaction medium is maintained at a temperature from about 10° C. to about 30° C. during the contacting step.

Embodiment 39. The process of any of Embodiments 4 to 38, wherein the volume of reaction medium is about 5 liters to about 20 liters of reaction medium per kilogram of compound of Formula (VII) charged to the reaction medium.

Embodiment 40. The process of any of Embodiments 4 to 39, wherein the contacting step is carried out as a batch reaction.

Embodiment 41. The process of Embodiment 40, wherein at least about 25 kilograms of the compound of Formula (VII) are charged to the batch reaction.

Embodiment 42. The process of Embodiment 40, wherein at least about 50 kilograms of the compound of Formula (VII) are charged to the batch reaction.

Embodiment 43. The process of Embodiment 40, wherein at least about 75 kilograms of the compound of Formula (VII) are charged to the batch reaction.

Embodiment 44. The process of Embodiment 40, wherein at least about 100 kilograms of the compound of Formula (VII) are charged to the batch reaction.

Embodiment 45. The process of any of Embodiments 4 to 44, wherein the compound of Formula (VIII) is isolated from the organic phase by crystallization.

Embodiment 46. The process of any of Embodiments 4 to 44, wherein the organic phase comprises an organic phase solvent, and the process further comprises exchanging the organic phase solvent with a replacement solvent to form a crystallization mixture comprising the compound of Formula (VIII).

Embodiment 47. The process of Embodiment 46, wherein the process further comprises crystallizing the compound of Formula (VIII) from the crystallization mixture.

Embodiment 48. The process of Embodiment 47, wherein the crystallization mixture is seeded with a crystalline form of the compound of Formula (VIII).

Embodiment 49. The process of Embodiment 48, wherein the crystallization mixture is seeded with at least about 0.01 relative weight of the crystalline form.

Embodiment 50. The process of Embodiment 49, wherein the crystallization mixture is seeded with at least about 0.03 relative weight of the crystalline form.

Embodiment 51. The process of any of Embodiments 48 to 50, wherein the crystalline form is an anhydrate crystalline form.

Embodiment 52. The process of any of Embodiments 46 to 51, wherein the organic phase solvent comprises a polar solvent.

Embodiment 53. The process of any of Embodiments 46 to 51, wherein the organic phase solvent comprises at least one solvent selected from the group consisting of chlorinated hydrocarbons and ethers.

Embodiment 54. The process of any of Embodiments 46 to 51, wherein the organic phase solvent comprises at least one compound selected from the group consisting of dichloromethane and 2-methyltetrahydrofuran.

Embodiment 55. The process of any of Embodiments 46 to 51, wherein the organic phase solvent comprises dichloromethane.

Embodiment 56. The process of any of Embodiments 46 to 55, wherein the replacement solvent comprises an alcohol.

Embodiment 57. The process of any of Embodiments 46 to 55, wherein the replacement solvent comprises ethanol.

Embodiment 58. The process of any of Embodiments 46 to 51, wherein the organic phase solvent comprises a polar solvent and the replacement solvent comprises an alcohol.

Embodiment 59. The process of any of Embodiments 46 to 51, wherein the organic phase solvent comprises dichloromethane and the replacement solvent comprises ethanol.

Embodiment 60. The process of any of Embodiments 46 to 51, wherein the organic phase solvent has a boiling point that is lower than the boiling point of the replacement solvent.

Embodiment 61. The process of Embodiment 60, wherein the boiling point of the organic phase solvent is at least about 20° C. lower than the boiling point of the replacement solvent.

Embodiment 62. The process of any of Embodiments 46 to 61, wherein the organic phase solvent is exchanged with the replacement solvent by continuous level distillation.

Embodiment 63. The process of Embodiment 62, wherein the continuous level distillation is conducted under conditions sufficient to maintain the compound of Formula (VIII) in solution during the continuous distillation.

Embodiment 64. The process of Embodiment 62 or 63, wherein the continuous level distillation is continuous level vacuum distillation.

Embodiment 65. The process of any of Embodiments 62 to 64, wherein the replacement solvent is charged in an amount sufficient to maintain at least about 15 relative volumes of total solvent per kilogram of the compound of Formula (VIII) during the distillation.

Embodiment 66. The process of any of Embodiments 62 to 64, wherein the replacement solvent is charged in an amount sufficient to maintain at least about 18 relative volumes of total solvent per kilogram of the compound of Formula (VIII) during the distillation.

Embodiment 67. The process of any of Embodiments 62 to 66, wherein the continuous level vacuum distillation is conducted at a temperature that does not exceed about 60° C.

Embodiment 68. The process of any of Embodiments 46 to 67, wherein the crystallization mixture is seeded with a crystalline form of the compound of Formula (VIII) and maintained at a temperature greater than about 40° C. for at least about five hours after seeding.

Embodiment 69. The process of any of Embodiments 46 to 68, wherein the crystallization mixture is cooled to a temperature of about 20° C. over a period of at least five hours before isolating the compound of Formula (VIII).

Embodiment 70. The process of any of Embodiments 1 to 69, wherein the stoichiometric process yield of the compound of Formula (VIII) is at least about 50%.

Embodiment 71. The process of any of Embodiments 1 to 69, wherein the stoichiometric process yield of the compound of Formula (VIII) is at least about 60%.

Embodiment 72. A crystalline form of a compound having the structure of Formula (VII):

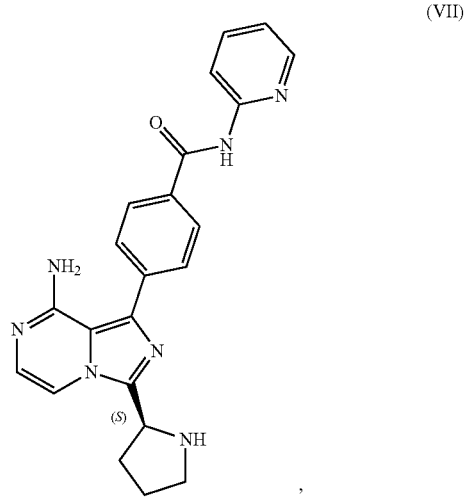

(VII)

wherein the crystalline form is characterized by a reflection X-ray powder diffraction pattern comprising at least three peaks selected from the group consisting of 9.9±0.2 °2θ, 11.1±0.2 °2θ, 12.8±0.2 °2θ, 14.1±0.2 °2θ, and 19.0±0.2 °2θ.

Embodiment 73. A process for preparing a compound having the structure of Formula (VII):

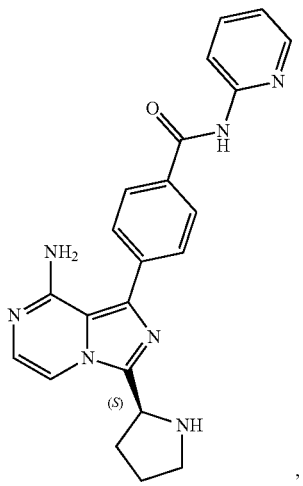

(VII)

or a salt thereof, wherein the process comprises:

contacting a compound having the structure of Formula (V):

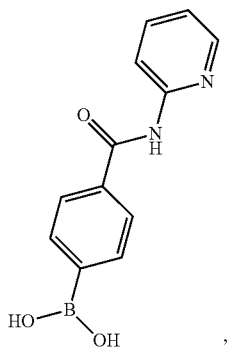

(V)

or a salt thereof, with a compound having the structure of Formula (VI):

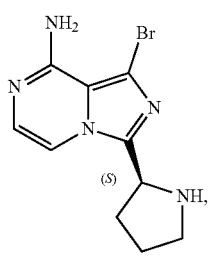

(VI)

or a salt thereof, in the presence of a base and a palladium catalyst in an aqueous reaction medium comprising an organic solvent to form a reaction mixture comprising the compound of Formula (VII), or salt thereof;

decreasing the amount of water present in the reaction mixture to form a substantially anhydrous mixture comprising the compound of Formula (VII), or salt thereof; and isolating the compound of Formula (VII), or salt thereof, from the substantially anhydrous mixture.

Embodiment 74. The process of Embodiment 73, wherein the isolating step comprises filtering the substantially anhydrous mixture.

Embodiment 75. The process of Embodiment 73 or 74, wherein the aqueous reaction medium further comprises an alkali metal halide.

Embodiment 76. The process of Embodiment 73 or 74, wherein the aqueous reaction medium further comprises an alkali metal iodide.

Embodiment 77. The process of Embodiment 73 or 74, wherein the aqueous reaction medium further comprises potassium iodide.

Embodiment 78. The process of any of Embodiments 73 to 77, wherein the organic solvent comprises at least one solvent selected from the group consisting of aromatic hydrocarbons, alcohols, ketones, ethers, esters, and nitriles.

Embodiment 79. The process of any of Embodiments 73 to 77, wherein the organic solvent comprises at least one solvent selected from the group consisting of methanol, ethanol, propanol, butanol, pentanol, dioxane, toluene, acetone, methyl ethyl ketone, methyl isobutyl ketone, tetrahydrofuran, 2-methyltetrahydrofuran, acetonitrile, ethyl acetate, isopropyl acetate, n-butyl acetate, and ethyl lactate.

Embodiment 80. The process of any of Embodiments 73 to 77, wherein the organic solvent comprises 2-butanol.

Embodiment 81. The process of any of Embodiments 73 to 80, wherein the base comprises at least one compound selected from the group consisting of triethylamine, potassium carbonate, potassium bicarbonate, sodium carbonate, sodium bicarbonate, cesium carbonate, tripropylamine, tributylamine, diiso-propylethylamine, N-methylmorpholine, N-methylpyrrolidine, methyldicyclohexylamine, and potassium phosphate.

Embodiment 82. The process of any of Embodiments 73 to 80, wherein the base comprises triethylamine.

Embodiment 83. The process of any of Embodiments 73 to 80, wherein the base comprises potassium carbonate.

Embodiment 84. The process of any of Embodiments 73 to 80, wherein the base comprises triethylamine and potassium carbonate.

Embodiment 85. The process of any of Embodiments 73 to 84, wherein the palladium catalyst comprises bis(tert-butyldicyclohexylphosphine)dichloropalladium(II).

Embodiment 86. The process of any of Embodiments 73 to 85, wherein the compound of Formula (VI) is contacted with about 0.5 to about 1.5 molar equivalents of the compound of Formula (V) relative to the compound of Formula (VI).

Embodiment 87. The process of any of Embodiments 73 to 85, wherein the compound of Formula (VI) is contacted with about 0.8 to about 1.2 molar equivalents of the compound of Formula (V) relative to the compound of Formula (VI).

Embodiment 88. The process of any of Embodiments 73 to 85, wherein the compound of Formula (VI) is contacted with about 0.9 to about 1.1 molar equivalents of the compound of Formula (V) relative to the compound of Formula (VI).

Embodiment 89. The process of any of Embodiments 77 to 88, wherein about 0.1 to about 1.0 molar equivalents of potassium iodide are charged to the aqueous reaction medium relative to the compound of Formula (VI).

Embodiment 90. The process of any of Embodiments 77 to 88, wherein about 0.2 to about 0.4 molar equivalents of potassium iodide are charged to the aqueous reaction medium relative to the compound of Formula (VI).

Embodiment 91. The process of any of Embodiments 73 to 90, wherein about 0.5 to about 10 molar equivalents of the base are charged to the aqueous reaction medium relative to the compound of Formula (VI).

Embodiment 92. The process of any of Embodiments 73 to 90, wherein the base comprises triethylamine and about 0.5 to about 10 molar equivalents of triethylamine are charged to the aqueous reaction medium relative to the compound of Formula (VI).

Embodiment 93. The process of any of Embodiments 73 to 90, wherein the base comprises triethylamine and about 1.0 to about 2.0 molar equivalents of triethylamine are charged to the aqueous reaction medium relative to the compound of Formula (VI).

Embodiment 94. The process of any of Embodiments 73 to 90, wherein the base comprises potassium carbonate and about 0.5 to about 10.0 molar equivalents of potassium carbonate are charged to the aqueous reaction medium relative to the compound of Formula (VI).

Embodiment 95. The process of any of Embodiments 73 to 90, wherein the base comprises potassium carbonate and about 2.0 to about 3.0 molar equivalents of potassium carbonate are charged to the aqueous reaction medium relative to the compound of Formula (VI).

Embodiment 96. The process of any of Embodiments 73 to 90, wherein the base comprises potassium carbonate and about 2.3 to about 2.7 molar equivalents of potassium carbonate are charged to the aqueous reaction medium relative to the compound of Formula (VI).

Embodiment 97. The process of any of Embodiments 73 to 96, wherein about 0.002 to about 0.05 molar equivalents of the palladium catalyst are charged to the aqueous reaction medium relative to the compound of Formula (VI).

Embodiment 98. The process of any of Embodiments 73 to 96, wherein about 0.007 to about 0.013 molar equivalents of the palladium catalyst are charged to the aqueous reaction medium relative to the compound of Formula (VI).

Embodiment 99. The process of any of Embodiments 73 to 98, wherein the aqueous reaction medium is maintained at a temperature from about 50° C. to about 100° C. during the contacting step.

Embodiment 100. The process of any of Embodiments 73 to 98, wherein the aqueous reaction medium is maintained at a temperature from about 70° C. to about 90° C. during the contacting step.

Embodiment 101. The process of any of Embodiments 73 to 100, wherein the volume of aqueous reaction medium is about 10 liters to about 20 liters of aqueous reaction medium per kilogram of the compound of Formula (VI) charged to the aqueous reaction medium.

Embodiment 102. The process of any of Embodiments 73 to 101, wherein the volume ratio of water to organic solvent for the aqueous reaction medium is about 1:3 to about 3:1.

Embodiment 103. The process of any of Embodiments 73 to 101, wherein the contacting step is carried out as a batch reaction.

Embodiment 104. The process of Embodiment 103, wherein at least about 25 kilograms of the compound of Formula (VI) are charged to the batch reaction.

Embodiment 105. The process of Embodiment 103, wherein at least about 50 kilograms of the compound of Formula (VI) are charged to the batch reaction.

Embodiment 106. The process of Embodiment 103, wherein at least about 75 kilograms of the compound of Formula (VI) are charged to the batch reaction.

Embodiment 107. The process of Embodiment 103, wherein at least about 100 kilograms of the compound of Formula (VI) are charged to the batch reaction.

Embodiment 108. The process of any of Embodiments 73 to 107, wherein the decreasing step comprises separating the reaction mixture into an aqueous discard phase and an organic phase comprising the compound of Formula (VII).

Embodiment 109. The process of Embodiment 108, wherein the decreasing step further comprises distilling the organic phase under conditions sufficient to decrease the amount of water present in the organic phase and provide the substantially anhydrous mixture.

Embodiment 110. The process of Embodiment 109 wherein the process further comprises washing the organic phase with water prior to distillation.

Embodiment 111. The process of any Embodiment 109 or 110, wherein the organic phase is treated with a silica scavenger prior to distillation.

Embodiment 112. The process of any of Embodiments 109 to 111, wherein the organic phase is treated with a silica scavenger prior to distillation for a period of at least two hours.

Embodiment 113. The process of Embodiment 111 or 112, wherein the silica scavenger comprises a propane thiol functionalized silica.

Embodiment 114. The process of Embodiment 111 or 112, wherein the silica scavenger comprises QuadraSil™ MP.

Embodiment 115. The process of any of Embodiments 111 to 114, wherein the process further comprises removing the silica scavenger from the organic phase prior to distillation.

Embodiment 116. The process of any of Embodiments 111 to 114, wherein the process further comprises removing the silica scavenger from the organic phase by filtration prior to distillation.

Embodiment 117. The process of Embodiment 115 or 116, wherein the process further comprises washing the organic phase with an aqueous brine solution after removing the catalyst and prior to distillation.

Embodiment 118. The process of any of Embodiments 109 to 117, wherein the decreasing step comprises:
  separating the reaction mixture into an aqueous discard phase and an organic phase comprising the compound of Formula (VII);
  washing the organic phase with water;
  treating the organic phase with a silica scavenger;
  removing the silica scavenger from the organic phase;
  washing the organic phase with an aqueous brine solution; and
  distilling the organic phase under conditions sufficient to decrease the amount of water present in the organic phase.

Embodiment 119. The process of any of Embodiments 109 to 118, wherein the organic phase is distilled by vacuum distillation.

Embodiment 120. The process of any of Embodiments 109 to 118, wherein the organic phase is distilled by continuous level vacuum distillation.

Embodiment 121. The process of any of Embodiments 109 to 120, wherein the organic phase is distilled at a temperature not exceeding about 60° C.

Embodiment 122. The process of any of Embodiments 109 to 120, wherein the organic phase is distilled at a temperature from about 50° C. to about 60° C.

Embodiment 123. The process of any of Embodiments 109 to 122, wherein the organic phase comprises an alcohol.

Embodiment 124. The process of Embodiment 123, wherein the organic phase is supplemented with alcohol during the distilling step.

Embodiment 125. The process of any of Embodiments 109 to 122, wherein the organic phase comprises 2-butanol.

Embodiment 126. The process of Embodiment 125, wherein the organic phase is supplemented with 2-butanol during the distilling step.

Embodiment 127. The process of any of Embodiments 73 to 126, wherein the substantially anhydrous mixture comprises less than about 5 weight % water.

Embodiment 128. The process of any of Embodiments 73 to 126, wherein the substantially anhydrous mixture comprises less than about 3 weight % water.

Embodiment 129. The process of any of Embodiments 73 to 128, wherein the isolating step comprises crystallizing the compound of Formula (VII) from the substantially anhydrous mixture.

Embodiment 130. The process of Embodiment 129, wherein the substantially anhydrous mixture is seeded with a crystalline form of the compound of Formula (VII).

Embodiment 131. The process of Embodiment 129 or 130, wherein the substantially anhydrous mixture is maintained at a temperature of at least about 70° C. for a period of at least two hours after crystallization initiates.

Embodiment 132. The process of Embodiment 129 or 130, wherein the substantially anhydrous mixture is maintained at a temperature of at least about 70° C. for a period of at least two hours after crystallization initiates and then cooled to crystallize the compound of Formula (VII).

Embodiment 133. The process of any of Embodiments 73 to 132, wherein the stoichiometric process yield of the compound of Formula (VII) is at least about 50%.

Embodiment 134. The process of any of Embodiments 73 to 132, wherein the stoichiometric process yield of the compound of Formula (VII) is at least about 65%.

Embodiment 135. The process of any of Embodiments 73 to 132, wherein the stoichiometric process yield of the compound of Formula (VII) is at least about 75%.

Embodiment 136. A process for preparing a compound having the structure of Formula (VI):

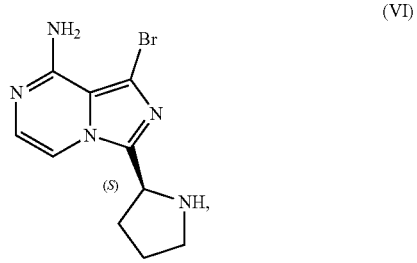

(VI)

or a salt thereof, wherein the process comprises:
contacting a compound of Formula (IV):

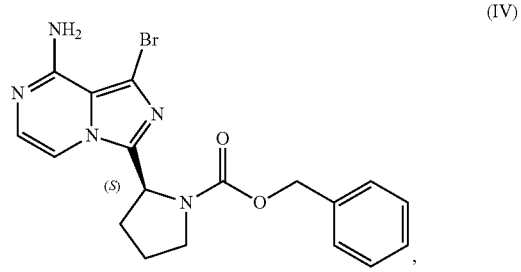

(IV)

or a salt thereof, with an acidic medium under conditions sufficient to deprotect the compound of Formula (IV) and form a reaction mixture comprising the compound of Formula (VI), or a salt thereof, and a benzyl halide by-product;
removing at least a portion of the benzyl halide by-product from the reaction mixture; and
isolating the compound of Formula (VI), or salt thereof, from the reaction mixture under conditions sufficient to substantially avoid the formation of an aminal impurity.

Embodiment 137. The process of Embodiment 136, wherein the isolating step comprises:
removing at least a portion of the benzyl halide by-product from the reaction mixture;
increasing the pH of the resulting reaction mixture to a basic pH to form a basic reaction medium comprising the compound of Formula (VI), or salt thereof; and
isolating the compound of Formula (VI), or salt thereof, from the basic reaction mixture.

Embodiment 138. The process of Embodiment 136, wherein the isolating step comprises:
extracting at least a portion of the benzyl halide by-product from the reaction mixture into a discard organic phase;
increasing the pH of the resulting reaction mixture to a basic pH to form a basic reaction medium comprising the compound of Formula (VI), or salt thereof;
extracting the compound of Formula (VI), or salt thereof, from the basic reaction medium into a product organic phase; and
isolating the compound of Formula (VI), or salt thereof, from the product organic phase.

Embodiment 139. The process of any of Embodiments 136 to 138, wherein the acidic medium is an aqueous acidic medium.

Embodiment 140. The process of any of Embodiments 136 to 139, wherein a sulfate salt of the compound of Formula (IV) is contacted with the acidic medium.

Embodiment 141. The process of any of Embodiments 136 to 140, wherein the acidic medium comprises a mineral acid.

Embodiment 142. The process of any of Embodiments 136 to 140, wherein the acidic medium comprises hydrochloric acid.

Embodiment 143. The process of any of Embodiments 136 to 142, wherein the acidic medium comprises at least about 10 molar equivalents of the acid relative to the compound of Formula (IV), or salt thereof.

Embodiment 144. The process of any of Embodiments 136 to 142, wherein the acidic medium comprises from about 10 to about 40 molar equivalents of the acid relative to the compound of Formula (IV), or salt thereof.

Embodiment 145. The process of any of Embodiments 136 to 142, wherein the acidic medium comprises from about 10 to about 25 molar equivalents of the acid relative to the compound of Formula (IV), or salt thereof.

Embodiment 146. The process of any of Embodiments 136 to 145, wherein the volume of acidic medium is about 2 liters to about 10 liters of acidic medium per kilogram of the compound of Formula (IV), or salt thereof, charged to the acidic medium.

Embodiment 147. The process of any of Embodiments 136 to 145, wherein the volume of acidic medium is about 3 liters to about 4 liters of acidic medium per kilogram of the compound of Formula (IV), or salt thereof, charged to the acidic medium.

Embodiment 148. The process of any of Embodiments 136 to 147, wherein the acidic medium is maintained at a temperature from about 25° C. to about 70° C. during the contacting step.

Embodiment 149. The process of any of Embodiments 136 to 147, wherein the acidic medium is maintained at a temperature from about 40° C. to about 50° C. during the contacting step.

Embodiment 150. The process of any of Embodiments 136 to 149, wherein the contacting step is carried out as a batch reaction.

Embodiment 151. The process of Embodiment 150, wherein at least about 50 kilograms of the compound of Formula (IV) are charged to the batch reaction.

Embodiment 152. The process of Embodiment 150, wherein at least about 100 kilograms of the compound of Formula (IV) are charged to the batch reaction.

Embodiment 153. The process of Embodiment 150, wherein at least about 200 kilograms of the compound of Formula (IV) are charged to the batch reaction.

Embodiment 154. The process of Embodiment 150, wherein at least about 300 kilograms of the compound of Formula (IV) are charged to the batch reaction.

Embodiment 155. The process of any of Embodiments 136 to 154, wherein the process comprises selectively extracting prior to the isolating step at least a portion of the benzyl halide by-product from the reaction mixture into a discard organic phase relative to the compound of Formula (VI).

Embodiment 156. The process of Embodiment 155, wherein at least about 80 weight % of the compound of benzyl halide by-product present in the reaction mixture is extracted into the discard organic phase.

Embodiment 157. The process of Embodiment 155, wherein less than about 20 weight % of the compound of Formula (VI) present in the reaction mixture is extracted into the discard organic phase.

Embodiment 158. The process of Embodiment 155, wherein at least about 80 weight % of the compound of benzyl halide by-product present in the reaction mixture and less than about 20 weight % of the compound of Formula (VI) present in the reaction mixture is extracted into the discard organic phase.

Embodiment 159. The process of Embodiment 155, wherein at least about 90 weight % of the compound of benzyl halide by-product present in the reaction mixture and less than about 10 weight % of the compound of Formula (VI) present in the reaction mixture is extracted into the discard organic phase.

Embodiment 160. The process of Embodiment 155, wherein at least about 95 weight % of the compound of benzyl halide by-product present in the reaction mixture and less than about 5 weight % of the compound of Formula (VI) present in the reaction mixture is extracted into the discard organic phase.

Embodiment 161. The process of any of Embodiments 155 to 160, wherein the discard organic phase comprises at least one solvent selected from the group consisting of alkyl hydrocarbons, aromatic hydrocarbons, chlorinated hydrocarbons, and ethers.

Embodiment 162. The process of any of Embodiments 155 to 160, wherein the discard organic phase comprises at least one compound selected from the group consisting of pentane, hexane, heptane, octane, nonane, toluene, dichloromethane, methyl tert-butyl ether, and 2-methyltetrahydrofuran.

Embodiment 163. The process of any of Embodiments 155 to 160, wherein the discard organic phase comprises heptane.

Embodiment 164. The process of any of Embodiments 155 to 163, wherein the process further comprises:

increasing the pH of the reaction mixture after the benzyl halide by-product extraction to form a basic reaction medium comprising the compound of Formula (VI), or salt thereof; and extracting the compound of Formula (VI), or salt thereof, from the basic reaction medium into a product organic phase.

Embodiment 165. The process of Embodiment 164, wherein the pH of the basic reaction mixture is at least about 8.0.

Embodiment 166. The process of Embodiment 164, wherein the pH of the basic reaction mixture is at least about 10.0.

Embodiment 167. The process of any of Embodiments 164 to 166, wherein the product organic phase comprises at least one solvent selected from the group consisting of alkyl hydrocarbons, aromatic hydrocarbons, chlorinated hydrocarbons, and ethers.

Embodiment 168. The process of any of Embodiments 164 to 166, wherein the product organic phase comprises at least one compound selected from the group consisting of dichloromethane, 2-methyltetrahydrofuran, and anisole.

Embodiment 169. The process of any of Embodiments 164 to 166, wherein the product organic phase comprises 2-methyltetrahydrofuran.

Embodiment 170. The process of any of Embodiments 164 to 169, wherein the process further comprises washing the product organic phase with water.

Embodiment 171. The process of any of Embodiments 164 to 170, wherein the process further comprises distilling the product organic phase under conditions sufficient to reduce the amount of water present in the product organic phase.

Embodiment 172. The process of Embodiment 171, wherein the product organic phase comprises 2-methyltetrahydrofuran and additional 2-methyltetrahydrofuran is charged to the product organic phase during the distilling step.

Embodiment 173. The process of Embodiment 171 or 172, wherein the product organic phase is distilled under atmospheric pressure.

Embodiment 174. The process of any of Embodiments 136 to 173, wherein the isolating step comprises crystallizing the compound of Formula (VI).

Embodiment 175. The process of Embodiment 174, wherein the isolating step further comprises seeding with a crystalline form of the compound of Formula (VI) to promote crystallization.

Embodiment 176. The process of Embodiment 174, wherein the isolating step comprises seeding with at least about 0.0005 relative weight of the crystalline form of the compound of Formula (VI) to promote crystallization.

Embodiment 177. The process of Embodiment 174, wherein the isolating step comprises seeding with at least about 0.001 relative weight of the crystalline form of the compound of Formula (VI) to promote crystallization.

Embodiment 178. The process of any of Embodiments 175 to 177, wherein the process further comprises charging an antisolvent to promote crystallization.

Embodiment 179. The process of Embodiment 178, wherein the anti-solvent is heptane.

Embodiment 180. The process of Embodiment 136, wherein the isolating step comprises:
selectively extracting at least a portion of the benzyl halide by-product from the reaction mixture into a discard organic phase relative to the compound of Formula (VI);
increasing the pH of the resulting reaction mixture to a pH greater than about 7.0 to form a basic reaction mixture;
selectively extracting prior at least a portion of the compound of Formula (VI) from the basic reaction mixture into a product organic phase; and
distilling the product organic phase under conditions sufficient to reduce the amount of water present in the product organic phase to form a distilled organic phase comprising the compound of Formula (VI).

Embodiment 181. The process of Embodiment 180, wherein the process further comprises crystallizing the compound of Formula (VI) from the distilled organic phase.

Embodiment 182. The process of any of Embodiments 136 to 181, wherein the aminal impurity comprises a compound having the structure of Formula (X):

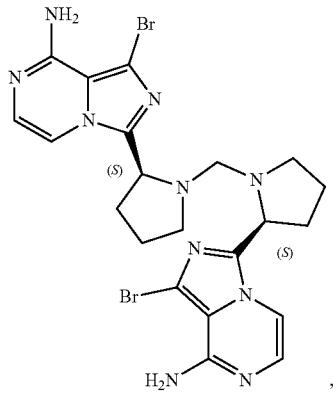

or a salt thereof.

Embodiment 183. The process of any of Embodiments 136 to 182, wherein the isolated compound of Formula (VI), or salt thereof, comprises less than 5 weight % of the aminal impurity.

Embodiment 184. The process of any of Embodiments 136 to 182, wherein the isolated compound of Formula (VI), or salt thereof, comprises less than 3 weight % of the aminal impurity.

Embodiment 185. The process of any of Embodiments 136 to 182, wherein the isolated compound of Formula (VI), or salt thereof, comprises less than 1 weight % of the aminal impurity.

Embodiment 186. The process of any of Embodiments 136 to 185, wherein the stoichiometric process yield of the compound of Formula (VI) is at least about 50%.

Embodiment 187. The process of any of Embodiments 136 to 185, wherein the stoichiometric process yield of the compound of Formula (VI) is at least about 65%.

Embodiment 188. The process of any of Embodiments 136 to 185, wherein the stoichiometric process yield of the compound of Formula (VI) is at least about 80%.

Embodiment 189. A process for preparing a compound having the structure of Formula (V):

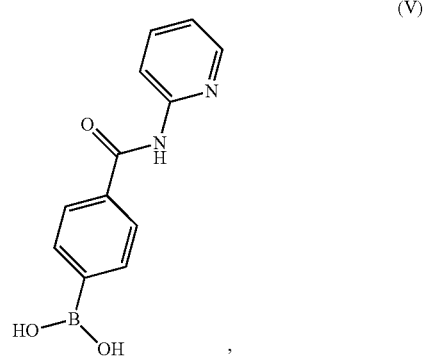 [SMILES: O=C(Nc1ccccn1)c1ccc(B(O)O)cc1]

or a salt thereof, wherein the process comprises contacting 4-carboxyphenylboronic acid, or a salt thereof, with thionyl chloride and a catalyst in a reaction medium comprising an organic solvent to form an acyl chloride intermediate which is then contacted in situ with 2-aminopyridine to form a reaction mixture comprising the compound of Formula (V), or salt thereof.

Embodiment 190. The process of Embodiment 189, wherein the process further comprises isolating the compound of Formula (V), or salt thereof, from the reaction mixture.

Embodiment 191. The process of Embodiment 189 or 190, wherein the catalyst comprises tetrabutylammonium chloride.

Embodiment 192. The process of Embodiment 189 or 190, wherein the catalyst comprises N-methylformanilide.

Embodiment 193. The process of Embodiment 189 or 190, wherein the catalyst does not comprise N,N-dimethylformamide.

Embodiment 194. The process of any of Embodiments 189 to 193, wherein the reaction medium does not comprise N,N-dimethylformamide.

Embodiment 195. The process of any of Embodiments 189 to 194, wherein the organic solvent comprises at least one solvent selected from the group consisting of aromatic hydrocarbons, aromatic heterocycles, and nitriles.

Embodiment 196. The process of any of Embodiments 189 to 194, wherein the organic solvent comprises a compound selected from the group consisting of toluene, acetonitrile, and pyridine.

Embodiment 197. The process of any of Embodiments 189 to 194, wherein the organic solvent comprises toluene.

Embodiment 198. The process of any of Embodiments 189 to 197, wherein the volume of reaction medium is about 3 liters to about 30 liters of reaction medium per kilogram of the 4-carboxyphenyl-boronic acid, or salt thereof, charged to the reaction medium.

Embodiment 199. The process of any of Embodiments 189 to 197, wherein the volume of reaction medium is about 5 liters to about 15 liters of reaction medium per kilogram of the 4-carboxyphenyl-boronic acid, or salt thereof, charged to the reaction medium.

Embodiment 200. The process of any of Embodiments 189 to 199, wherein the reaction medium is maintained at a temperature from about 50° C. to about 90° C. during the contacting step.

Embodiment 201. The process of any of Embodiments 189 to 199, wherein the reaction medium is maintained at a temperature from about 60° C. to about 80° C. during the contacting step.

Embodiment 202. The process of any of Embodiments 189 to 201, wherein the contacting step is carried out as a batch reaction.

Embodiment 203. The process of any of Embodiments 189 to 202, wherein the 4-carboxyphenylboronic acid, or salt thereof, is contacted with about 2 to about 5 molar equivalents of thionyl chloride relative to the 4-carboxyphenylboronic acid, or salt thereof.

Embodiment 204. The process of any of Embodiments 189 to 202, wherein the 4-carboxyphenylboronic acid, or salt thereof, is contacted with about 2 to about 3.5 molar equivalents of thionyl chloride relative to the 4-carboxyphenylboronic acid, or salt thereof.

Embodiment 205. The process of any of Embodiments 189 to 202, wherein the 4-carboxyphenylboronic acid, or salt thereof, is contacted with about 2.75 molar equivalents of thionyl chloride relative to the 4-carboxyphenylboronic acid, or salt thereof.

Embodiment 206. The process of any of Embodiments 189 to 205, wherein about 1.5 to about 5 molar equivalents of the 2-aminopyridine are charged to the reaction medium relative to the 4-carboxyphenylboronic acid, or salt thereof.

Embodiment 207. The process of any of Embodiments 189 to 205, wherein about 1.5 to about 3.5 molar equivalents of the 2-aminopyridine are charged to the reaction medium relative to the 4-carboxyphenylboronic acid, or salt thereof.

Embodiment 208. The process of any of Embodiments 189 to 205, wherein about 2 molar equivalents of the 2-aminopyridine are charged to the reaction medium relative to the 4-carboxyphenylboronic acid, or salt thereof.

Embodiment 209. The process of any of Embodiments 189 to 208, wherein the stoichiometric process yield of the compound of Formula (V) is at least about 50%.

Embodiment 210. The process of any of Embodiments 189 to 208, wherein the stoichiometric process yield of the compound of Formula (V) is at least about 70%.

Embodiment 211. A crystalline sulfate salt of a compound having the structure of Formula (IV):

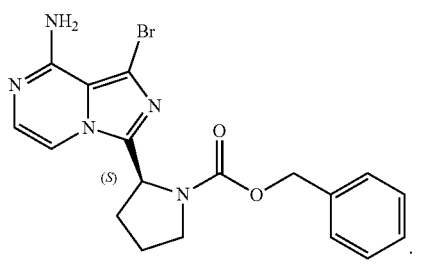

(IV)

Embodiment 212. The crystalline sulfate salt of Embodiment 211, wherein the crystalline sulfate salt has a stoichiometric ratio of one sulfate molecule and one hydrogen sulfate molecule to three freebase molecules.

Embodiment 213. The crystalline sulfate salt of Embodiment 211 or 212, wherein the crystalline sulfate salt is characterized by a reflection X-ray powder diffraction pattern comprising at least three peaks selected from the group consisting of 7.7±0.2 °2θ, 10.6±0.2 °2θ, 11.1±0.2 °2θ, 12.6±0.2 °2θ, and 13.5±0.2 °2θ.

Embodiment 214. A process for preparing a sulfate salt of a compound having the structure of Formula (IV):

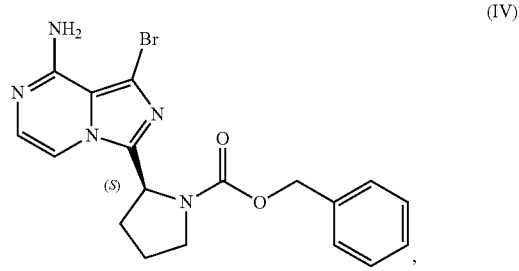

(IV)

wherein the process comprises:
contacting a compound having the structure of Formula (III):

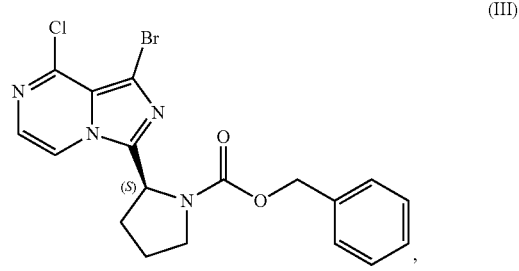

(III)

or a salt thereof, with an aminating agent in a reaction medium to form a reaction mixture comprising the compound of Formula (IV);
forming a sulfate salt of the compound of Formula (IV); and
isolating the sulfate salt.

Embodiment 215. The process of Embodiment 214, wherein the sulfate salt has a stoichiometric ratio of one sulfate molecule and one hydrogen sulfate molecule to three freebase molecules.

Embodiment 216. The process of Embodiment 214 or 215, wherein the process comprises isolating the compound of Formula (IV) from the reaction mixture as a freebase prior to the forming step.

Embodiment 217. The process of Embodiment 214 or 215, wherein the process comprises:
isolating the compound of Formula (IV) from the reaction medium as a freebase;
contacting the freebase with sulfuric acid to form the sulfate salt; and
isolating the sulfate salt.

Embodiment 218. The process of Embodiment 214 or 215, wherein the process comprises:
washing the reaction mixture to reduce the amount of ammonia present in the reaction mixture;
isolating the compound of Formula (IV) from the washed reaction medium as a freebase;
contacting the freebase with sulfuric acid to form the sulfate salt; and
isolating the sulfate salt.

Embodiment 219. The process of Embodiment 214 or 215, wherein the process comprises:
washing the reaction mixture with a brine solution;
distilling the washed reaction mixture to reduce the amount of ammonia present in the washed reaction mixture;
isolating the compound of Formula (IV) from the distilled reaction medium as a freebase;
contacting the freebase with sulfuric acid to form the sulfate salt; and
isolating the sulfate salt.

Embodiment 220. The process of any of Embodiments 214 to 219, wherein the process further comprises isolating the sulfate salt by filtration.

Embodiment 221. The process of any of Embodiments 214 to 220, wherein the aminating agent is ammonia.

Embodiment 222. The process of any of Embodiments 214 to 220, wherein the aminating agent is ammonium hydroxide.

Embodiment 223. The process of any of Embodiments 214 to 221, wherein the reaction medium comprises at least one solvent selected from the group consisting of alkyl hydrocarbons, aromatic hydrocarbons, chlorinated hydrocarbons, aromatic heterocycles, alcohols, ethers, and dipolar aprotic solvents.

Embodiment 224. The process of any of Embodiments 214 to 221, wherein the reaction medium comprises at least one compound selected from the group consisting of methanol, ethanol, propanol, butanol, pentanol, N-methylpyrrolidinone, and N,N-dimethylformamide.

Embodiment 225. The process of any of Embodiments 214 to 221, wherein the reaction medium comprises an aliphatic alcohol.

Embodiment 226. The process of any of Embodiments 214 to 221, wherein the reaction medium comprises butanol.

Embodiment 227. The process of any of Embodiments 214 to 221, wherein the reaction medium comprises 2-butanol.

Embodiment 228. The process of any of Embodiments 214 to 227, wherein the reaction medium is maintained at a temperature above 70° C. during the contacting step.

Embodiment 229. The process of any of Embodiments 214 to 227, wherein the reaction medium is maintained at a temperature above 90° C. during the contacting step.

Embodiment 230. The process of any of Embodiments 214 to 227, wherein the reaction medium is maintained at a temperature from about 50° C. to about 100° C. during the contacting step.

Embodiment 231. The process of any of Embodiments 214 to 227, wherein the reaction medium is maintained at a temperature from about 60° C. to about 95° C. during the contacting step.

Embodiment 232. The process of any of Embodiments 214 to 231, wherein the volume of reaction medium is about 1.5 liters to about 40 liters of reaction medium per kilogram of the compound of Formula (III), or salt thereof, charged to the reaction medium.

Embodiment 233. The process of any of Embodiments 214 to 231, wherein the volume of reaction medium is about 2.0 liters to about 30 liters of reaction medium per kilogram of the compound of Formula (III), or salt thereof, charged to the reaction medium.

Embodiment 234. The process of any of Embodiments 214 to 233, wherein the contacting step is carried out as a batch reaction.

Embodiment 235. The process of Embodiment 234, wherein at least about 50 kilograms of the compound of Formula (III) are charged to the batch reaction.

Embodiment 236. The process of Embodiment 234, wherein at least about 100 kilograms of the compound of Formula (III) are charged to the batch reaction.

Embodiment 237. The process of Embodiment 234, wherein at least about 200 kilograms of the compound of Formula (III) are charged to the batch reaction.

Embodiment 238. The process of Embodiment 234, wherein at least about 300 kilograms of the compound of Formula (III) are charged to the batch reaction.

Embodiment 239. The process of any of Embodiments 214 to 238, wherein the forming step comprises contacting the compound of Formula (IV) with sulfuric acid to form a sulfate salt mixture comprising the sulfate salt.

Embodiment 240. The process of Embodiment 239, wherein the compound of Formula (IV) is contacted with at least about 0.5 molar equivalents of sulfuric acid relative to the compound of Formula (III).

Embodiment 241. The process of Embodiment 239, wherein the compound of Formula (IV) is contacted with about 1.25 to about 1.75 molar equivalents of sulfuric acid relative to the compound of Formula (III).

Embodiment 242. The process of any of Embodiments 214 to 241, wherein the stoichiometric process yield of the sulfate salt of Formula (IV) is at least about 50%.

Embodiment 243. The process of any of Embodiments 214 to 241, wherein the stoichiometric process yield of the sulfate salt of Formula (IV) is at least about 65%.

Embodiment 244. The process of any of Embodiments 214 to 241, wherein the stoichiometric process yield of the sulfate salt of Formula (IV) is at least about 80%.

Embodiment 245. A process for preparing a compound having the structure of Formula (II):

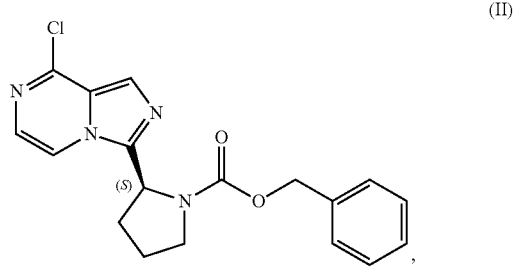

(II)

or a salt thereof, wherein the process comprises:
contacting a compound having the structure of Formula (I):

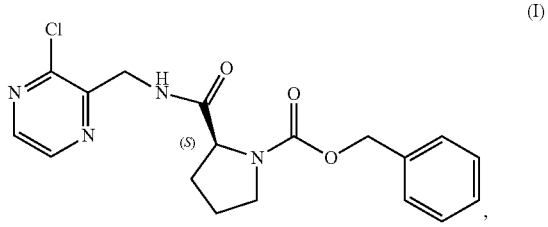

(I)

or a salt thereof, with a cyclizing agent in the presence of a catalyst in a reaction medium to form the compound of Formula (II), or salt thereof;

wherein the temperature of the reaction medium is controlled during the contacting step in a manner sufficient to maintain a chiral purity of at least about 80% for the compound of Formula (II), or salt thereof.

Embodiment 246. The process of Embodiment 245, wherein the cyclizing agent comprises phosphorus oxychloride.

Embodiment 247. The process of Embodiment 245 or 246, wherein the catalyst comprises a catalyst selected from the group consisting of N,N-dimethylformamide and N-methylformanilide.

Embodiment 248. The process of Embodiment 245 or 246, wherein the catalyst comprises N,N-dimethylformamide.

Embodiment 249. The process of any of Embodiments 245 to 248, wherein the reaction medium comprises at least one solvent selected from the group consisting of aromatic hydrocarbons, chlorinated hydrocarbons, ethers, and nitriles.

Embodiment 250. The process of any of Embodiments 245 to 248, wherein the reaction medium comprises at least one compound selected from the group consisting of acetonitrile, butyronitrile, dichloromethane, toluene, anisole, tetrahydrofuran, and 2-methyltetrahydrofuran.

Embodiment 251. The process of any of Embodiments 245 to 248, wherein the reaction medium comprises acetonitrile.

Embodiment 252. The process of any of Embodiments 245 to 251, wherein the compound of Formula (I), or salt thereof, is contacted with about 0.7 to about 10 molar equivalents of the cyclizing agent relative to the compound of Formula (I), or salt thereof.

Embodiment 253. The process of any of Embodiments 245 to 251, wherein the compound of Formula (I), or salt thereof, is contacted with about 1.5 to about 2.5 molar equivalents of the cyclizing agent relative to the compound of Formula (I), or salt thereof.

Embodiment 254. The process of any of Embodiments 245 to 251, wherein the compound of Formula (I), or salt thereof, is contacted with about 2.0 molar equivalents of the cyclizing agent relative to the compound of Formula (I), or salt thereof.

Embodiment 255. The process of any of Embodiments 245 to 254, wherein at least about 0.1 molar equivalents of the catalyst are charged to the reaction medium relative to the compound of Formula (I), or salt thereof.

Embodiment 256. The process of any of Embodiments 245 to 254, wherein about 0.1 to about 1.0 molar equivalents of the catalyst are charged to the reaction medium relative to the compound of Formula (I), or salt thereof.

Embodiment 257. The process of any of Embodiments 245 to 254, wherein at least about 0.4 molar equivalents of the catalyst are charged to the reaction medium relative to the compound of Formula (I), or salt thereof.

Embodiment 258. The process of any of Embodiments 245 to 254, wherein about 0.4 to about 1.0 molar equivalents of the catalyst are charged to the reaction medium relative to the compound of Formula (I), or salt thereof.

Embodiment 259. The process of any of Embodiments 245 to 254, wherein the catalyst comprises N,N-dimethylformamide, and at least about 0.1 molar equivalents of the catalyst are charged to the reaction medium relative to the compound of Formula (I), or salt thereof.

Embodiment 260. The process of any of Embodiments 245 to 254, wherein the catalyst comprises N,N-dimethylformamide, and from about 0.1 to about 1.0 molar equivalents of the catalyst are charged to the reaction medium relative to the compound of Formula (I), or salt thereof.

Embodiment 261. The process of any of Embodiments 245 to 254, wherein the catalyst comprises N,N-dimethylformamide, and at least about 0.4 molar equivalents of the catalyst are charged to the reaction medium relative to the compound of Formula (I), or salt thereof.

Embodiment 262. The process of any of Embodiments 245 to 254, wherein the catalyst comprises N,N-dimethylformamide, about 0.4 to about 1.0 molar equivalents of the catalyst are charged to the reaction medium relative to the compound of Formula (I), or salt thereof.

Embodiment 263. The process of any of Embodiments 245 to 254, wherein the catalyst comprises N,N-dimethylformamide, and at least about 0.6 molar equivalents of the catalyst are charged to the reaction medium relative to the compound of Formula (I), or salt thereof.

Embodiment 264. The process of any of Embodiments 245 to 254, wherein the catalyst comprises N,N-dimethylformamide, and about 0.6 molar equivalents of the catalyst are charged to the reaction medium relative to the compound of Formula (I), or salt thereof.

Embodiment 265. The process of any of Embodiments 245 to 264, wherein the temperature of the reaction medium is controlled during the contacting step in a manner sufficient to maintain a chiral purity of at least about 90% for the compound of Formula (II), or salt thereof.

Embodiment 266. The process of any of Embodiments 245 to 264, wherein the temperature of the reaction medium is controlled during the contacting step in a manner sufficient to maintain a chiral purity of at least about 95% for the compound of Formula (II), or salt thereof.

Embodiment 267. The process of any of Embodiments 245 to 266, wherein the reaction medium is maintained at a temperature less than about 80° C. during the contacting step.

Embodiment 268. The process of any of Embodiments 245 to 266, wherein the reaction medium is maintained at a temperature less than about 50° C. during the contacting step.

Embodiment 269. The process of any of Embodiments 245 to 266, wherein the reaction medium is maintained at a temperature from about 30° C. to about 50° C. during the contacting step.

Embodiment 270. The process of any of Embodiments 245 to 269, wherein the reaction medium is maintained at a temperature of about 40° C. during the contacting step.

Embodiment 271. The process of any of Embodiments 245 to 270, wherein the volume of reaction medium is about 2 liters to about 20 liters of reaction medium per kilogram of the compound of Formula (I), or salt thereof, charged to the reaction medium.

Embodiment 272. The process of any of Embodiments 245 to 270, wherein the volume of reaction medium is about 3 liters to about 10 liters of reaction medium per kilogram of the compound of Formula (I), or salt thereof, charged to the reaction medium.

Embodiment 273. The process of any of Embodiments 245 to 272, wherein the contacting step is carried out as a batch reaction.

Embodiment 274. The process of Embodiment 273, wherein at least about 50 kilograms of the compound of Formula (I) are charged to the batch reaction.

Embodiment 275. The process of Embodiment 273, wherein at least about 100 kilograms of the compound of Formula (I) are charged to the batch reaction.

Embodiment 276. The process of Embodiment 273, wherein at least about 200 kilograms of the compound of Formula (I) are charged to the batch reaction.

Embodiment 277. The process of Embodiment 273, wherein at least about 300 kilograms of the compound of Formula (I) are charged to the batch reaction.

Embodiment 278. The process of any of Embodiments 245 to 277, wherein the stoichiometric process yield of the compound of Formula (II) is at least about 50%.

Embodiment 279. The process of any of Embodiments 245 to 277, wherein the stoichiometric process yield of the compound of Formula (II) is at least about 65%.

Embodiment 280. The process of any of Embodiments 245 to 277, wherein the stoichiometric process yield of the compound of Formula (II) is at least about 80%.

Embodiment 281. A process for preparing a compound having the structure of Formula (III):

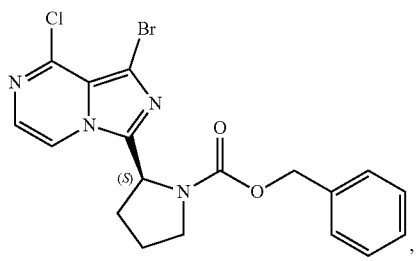

or a salt thereof, wherein the process comprises:

contacting a compound having the structure of Formula (I):

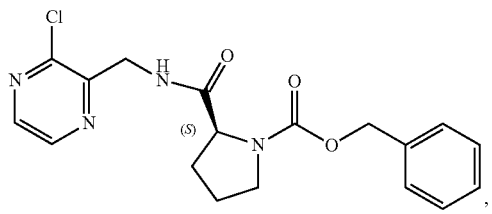

or a salt thereof, with a cyclizing agent in the presence of a catalyst in a reaction medium to form a compound of Formula (II):

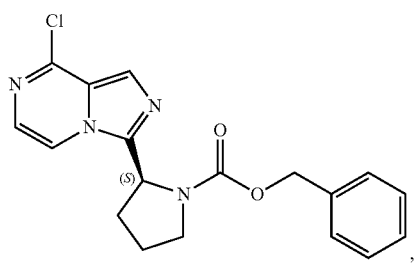

or salt thereof; and brominating the compound of Formula (II), or salt thereof, with a brominating agent to provide a compound having the structure of Formula (III):

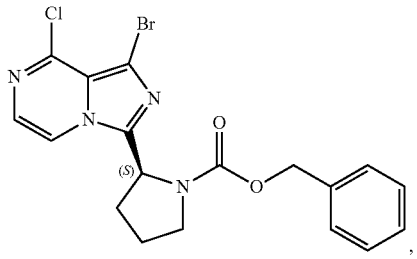

or a salt thereof;

wherein the temperature of the reaction medium is controlled during the contacting step in a manner sufficient to maintain a chiral purity of at least about 80% for the compound of Formula (II), or salt thereof.

Embodiment 282. The process of Embodiment 281, wherein the brominating agent comprises N-bromosuccinimide.

Embodiment 283. The process of Embodiment 281 or 282, wherein the compound of Formula (II), or salt thereof, is contacted with about 0.8 to about 1.2 molar equivalents of the brominating agent relative to the compound of Formula (II), or salt thereof.

Embodiment 284. The process of any of Embodiments 281 to 283, wherein the compound of Formula (II), or salt thereof, is isolated from the reaction medium prior to the brominating step.

Embodiment 285. The process of Embodiment 284, wherein the compound of Formula (II), or salt thereof, is contacted with the brominating agent in a bromination medium comprising at least one solvent selected from the group consisting of chlorinated hydrocarbons and polar aprotic solvents.

Embodiment 286. The process of Embodiment 284, wherein the compound of Formula (II), or salt thereof, is contacted with the brominating agent in a bromination medium comprising at least one solvent selected from the group consisting of N,N-dimethylformamide, N-methylpyrrolidinone, N-butylpyrrolidinone, dimethylsulphoxide, dimethylacetamide, and dichloromethane.

Embodiment 287. The process of Embodiment 284, wherein the compound of Formula (II), or salt thereof, is contacted with the brominating agent in a bromination medium comprising N,N-dimethylformamide.

Embodiment 288. The process of Embodiment 284, wherein the compound of Formula (II), or salt thereof, is contacted with the brominating agent in a bromination medium comprising N-methylpyrrolidinone.

Embodiment 289. The process of any of Embodiments 284 to 288, wherein the bromination medium is maintained at a temperature from about 5° C. to about 40° C. during the brominating step.

Embodiment 290. The process of any of Embodiments 284 to 288, wherein the bromination medium is maintained at a temperature of about 20° C. during the brominating step.

Embodiment 291. The process of any of Embodiments 284 to 290, wherein the brominating step is carried out as a batch reaction.

Embodiment 292. The process of Embodiment 291, wherein at least about 50 kilograms of the compound of Formula (II) are charged to the batch reaction.

Embodiment 293. The process of Embodiment 291, wherein at least about 100 kilograms of the compound of Formula (II) are charged to the batch reaction.

Embodiment 294. The process of Embodiment 291, wherein at least about 200 kilograms of the compound of Formula (II) are charged to the batch reaction.

Embodiment 295. The process of Embodiment 291, wherein at least about 300 kilograms of the compound of Formula (II) are charged to the batch reaction.

Embodiment 296. The process of any of Embodiments 284 to 295, wherein the process comprises isolating the compound of Formula (III), or salt thereof, from the bromination medium.

Embodiment 297. The process of Embodiment 296, wherein an aqueous solution is added to the bromination medium to isolate the compound of Formula (III), or salt thereof.

Embodiment 298. The process of Embodiment 296, wherein an aqueous solution having a basic pH is added to the bromination medium to isolate the compound of Formula (III), or salt thereof.

Embodiment 299. The process of Embodiment 296, wherein an aqueous sodium bicarbonate solution is added to the bromination mixture to isolate the compound of Formula (III), or salt thereof.

Embodiment 300. The process of Embodiment 299, wherein the sodium bicarbonate solution is about 1 weight % to 10 weight % sodium bicarbonate.

Embodiment 301. The process of Embodiment 299, wherein the sodium bicarbonate solution is about 2 weight % sodium bicarbonate.

Embodiment 302. The process of any of Embodiments 281 to 283, wherein the compound of Formula (III), or salt thereof, is prepared from the compound of Formula (II), or salt thereof, without isolating the compound of Formula (II), or salt thereof, from the reaction mixture.

Embodiment 303. The process of any of Embodiments 281 to 302, wherein the stoichiometric process yield of the compound of Formula (III) is at least about 50%.

Embodiment 304. The process of any of Embodiments 281 to 302, wherein the stoichiometric process yield of the compound of Formula (III) is at least about 65%.

Embodiment 305. The process of any of Embodiments 281 to 302, wherein the stoichiometric process yield of the compound of Formula (III) is at least about 80%.

Embodiment 306. The process of Embodiment 1, wherein the compound of Formula (VII), or salt thereof, is prepared by a process comprising:
contacting a compound having the structure of Formula (V):

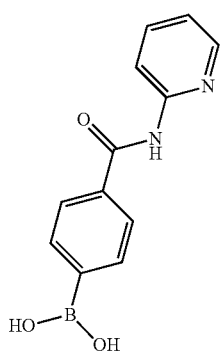

or a salt thereof, with a compound having the structure of Formula (VI):

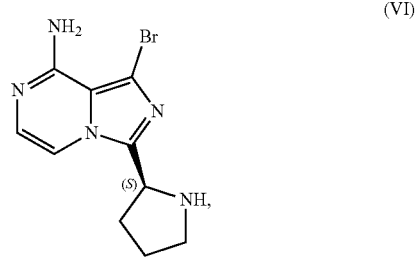

or a salt thereof, in the presence of a base and a palladium catalyst in a reaction medium comprising water and an organic solvent to form a reaction mixture comprising the compound of Formula (VII), or salt thereof;

decreasing the amount of water present in the reaction mixture to form a substantially anhydrous mixture comprising the compound of Formula (VII), or salt thereof; and isolating the compound of Formula (VII), or salt thereof, from the substantially anhydrous mixture.

Embodiment 307. The process of Embodiment 306, wherein the compound of Formula (VI), or salt thereof, is prepared by a process comprising:
contacting the compound of Formula (IV),

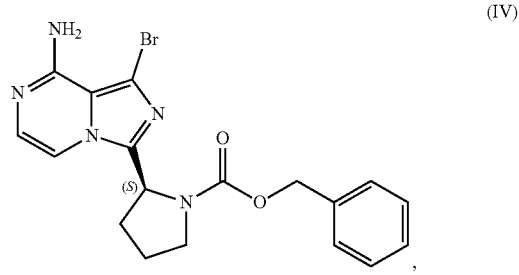

or a salt thereof, with an acidic medium under conditions sufficient to deprotect the compound of Formula (IV), or salt thereof, and form a reaction mixture comprising the compound Formula (VI), or a salt thereof, and a benzyl halide by-product; and isolating the compound of Formula (VI), or salt thereof, from the reaction mixture under conditions sufficient to substantially avoid the formation of an aminal impurity.

Embodiment 308. The process of Embodiment 306, wherein the compound of Formula (V), or salt thereof, is prepared by a process comprising contacting 4-carboxyphenylboronic acid, or a salt thereof, with thionyl chloride and a catalyst in a reaction medium comprising an organic solvent to form an acyl chloride intermediate which is then contacted in situ with 2-aminopyridine to form a reaction mixture comprising the compound of Formula (V), or salt thereof.

Embodiment 309. The process of Embodiment 306, wherein:

the compound of Formula (VI), or salt thereof, is prepared by a process comprising:

contacting the compound of Formula (IV):

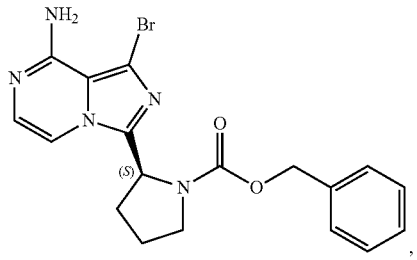

(IV)

or a salt thereof, with an acidic medium under conditions sufficient to deprotect the compound of Formula (IV), or salt thereof, and form a reaction mixture comprising a compound having the structure of Formula (VI), or a salt thereof, and a benzyl halide by-product; and isolating the compound of Formula (VI), or salt thereof, from the reaction mixture under conditions sufficient to substantially avoid the formation of an aminal impurity; and the compound of Formula (V), or salt thereof, is prepared by a process comprising contacting 4-carboxyphenylboronic acid, or a salt thereof, with thionyl chloride and a catalyst in a reaction medium comprising an organic solvent to form an acyl chloride which is then contacted in situ with 2-aminopyridine to form a reaction mixture comprising the compound of Formula (V), or salt thereof.

Embodiment 310. The process of any of Embodiments 306 to 309, wherein the compound of Formula (IV), or salt thereof, is a sulfate salt; and the sulfate salt is prepared by a process comprising:

contacting a compound having the structure of Formula (III):

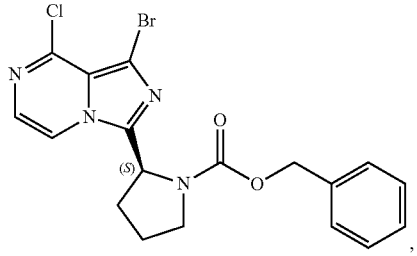

(III)

or a salt thereof, with an aminating agent in a reaction medium to form a reaction mixture comprising the compound of Formula (IV);

forming a sulfate salt of the compound of Formula (IV); and isolating the sulfate salt.

Embodiment 311. The process of Embodiment 310, wherein the compound of Formula (III), or salt thereof, is prepared by a process comprising:

contacting a compound having the structure of Formula (I):

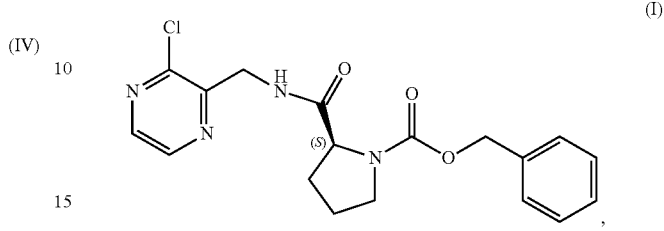

(I)

or a salt thereof, with a cyclizing agent in the presence of a catalyst in a reaction medium to form a compound of Formula (II):

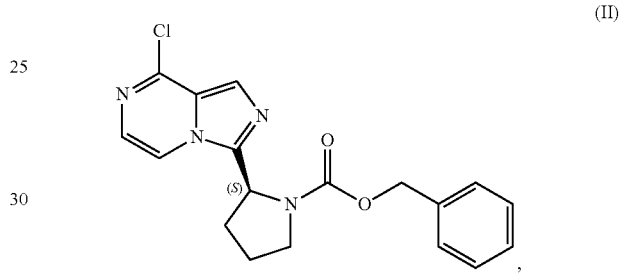

(II)

or salt thereof; and brominating the compound of Formula (II), or salt thereof, with a brominating agent to provide a compound having the structure of Formula (III), or salt thereof;

wherein the temperature of the reaction medium is controlled during the contacting step in a manner sufficient to maintain a chiral purity of at least about 80% for the compound of Formula (II), or salt thereof.

Embodiment 312. A process for preparing a compound having the structure of Formula (VIII):

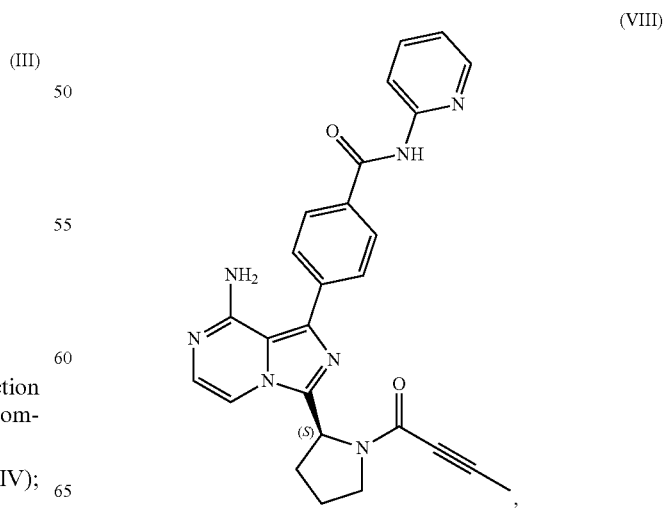

(VIII)

or a salt thereof, wherein the process comprises:
contacting a compound having the structure of Formula (V):

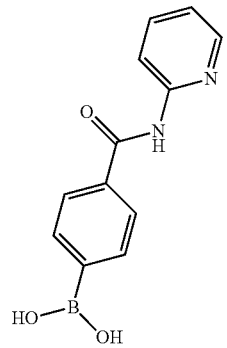
(V)

or a salt thereof, with a compound having the structure of Formula (VI):

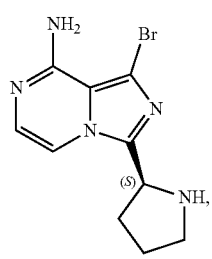
(VI)

or a salt thereof, in the presence of a base and a palladium catalyst in an aqueous reaction medium comprising an organic solvent to form a reaction mixture comprising a compound having the structure of Formula (VII):

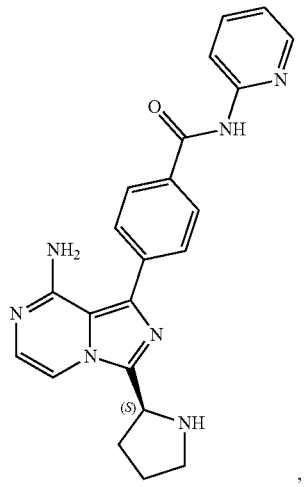
(VII)

or a salt thereof;
decreasing the amount of water present in the reaction mixture to form a substantially anhydrous mixture comprising the compound of Formula (VII), or salt thereof;
isolating the compound of Formula (VII), or salt thereof, from the substantially anhydrous mixture; and
converting the compound of Formula (VII), or salt thereof, to the compound of Formula (VIII).

Embodiment 313. A process for preparing a compound having the structure of Formula (VIII):

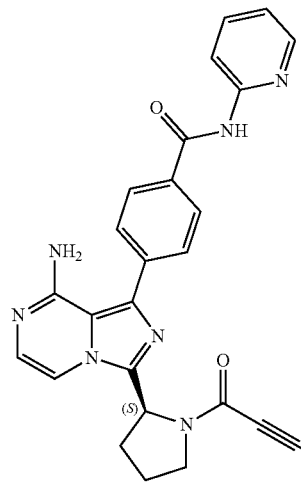
(VIII)

or a salt thereof, wherein the process comprises:
contacting a compound of having the structure of Formula (IV):

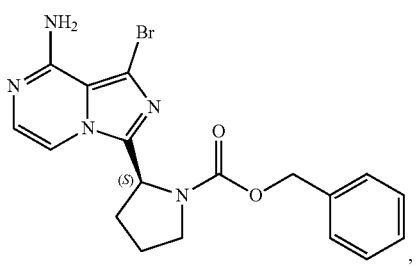
(IV)

or a salt thereof, with an acidic medium under conditions sufficient to deprotect the compound of Formula (IV) and form a reaction mixture comprising a compound having the structure of Formula (VI):

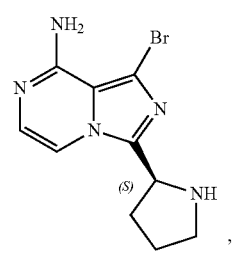
(VI)

or a salt thereof, and a benzyl halide by-product;
isolating the compound of Formula (VI), or salt thereof, from the reaction mixture under conditions sufficient to substantially avoid the formation of an aminal impurity; and converting the compound of Formula (VI), or salt thereof, to the compound of Formula (VIII), or salt thereof.

Embodiment 314. A process for preparing a compound having the structure of Formula (VIII):

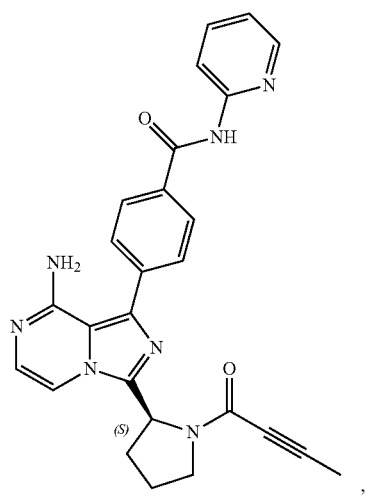

(VIII)

or a salt thereof, wherein the process comprises:

contacting a compound having the structure of Formula (III):

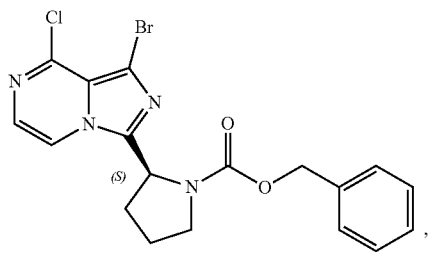

(III)

or a salt thereof, with an aminating agent in a reaction medium to form a reaction mixture comprising a compound having the structure of Formula (IV):

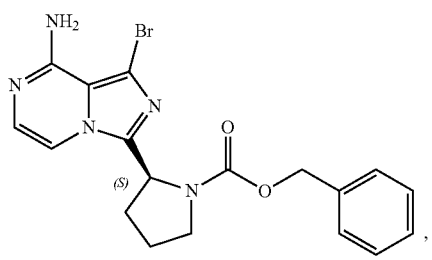

(IV)

forming a sulfate salt of the compound of Formula (IV);
isolating the sulfate salt; and
converting the sulfate salt to the compound of Formula (VIII), or salt thereof.

Embodiment 315. A process for preparing a compound having the structure of Formula (VIII):

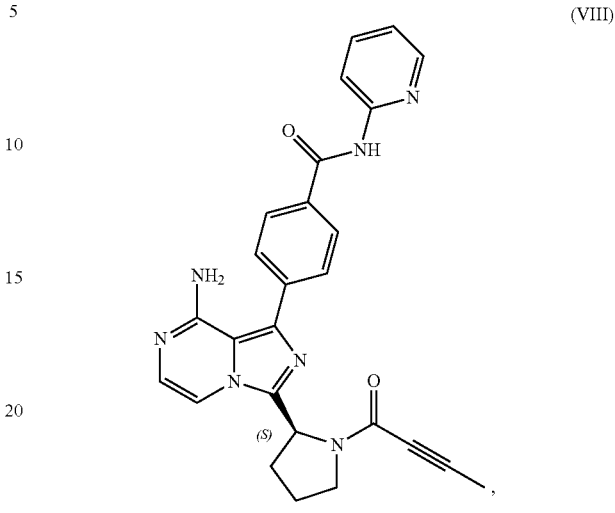

(VIII)

or a salt thereof, wherein the process comprises:

contacting a compound having the structure of Formula (I):

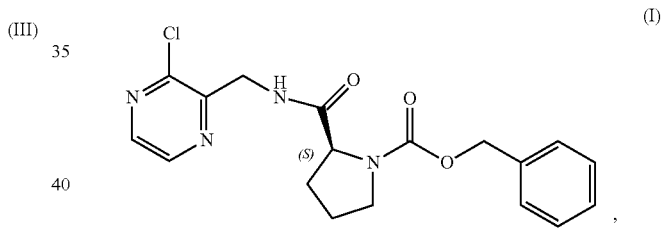

(I)

or a salt thereof, with a cyclizing agent in the presence of a catalyst in a reaction medium to form a compound of Formula (II):

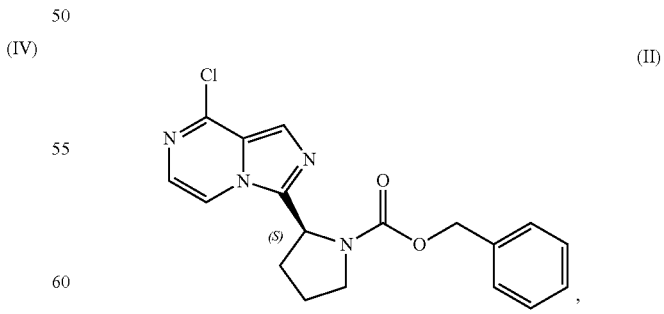

(II)

or salt thereof;

brominating the compound of Formula (II), or salt thereof, with a brominating agent to provide a compound having the structure of Formula (III):

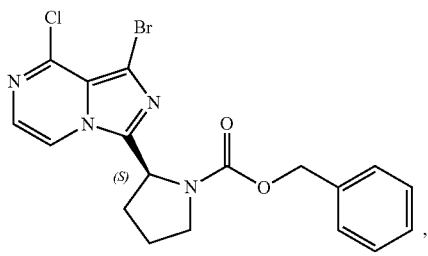

or salt thereof; and converting the compound of Formula (III), or salt thereof, to the compound of Formula (VIII), or salt thereof;

wherein the temperature of the reaction medium is controlled during the contacting step in a manner sufficient to maintain a chiral purity of at least about 80% for the compound of Formula (II), or salt thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:

1. A process for preparing a compound having the structure of Formula (VIII):

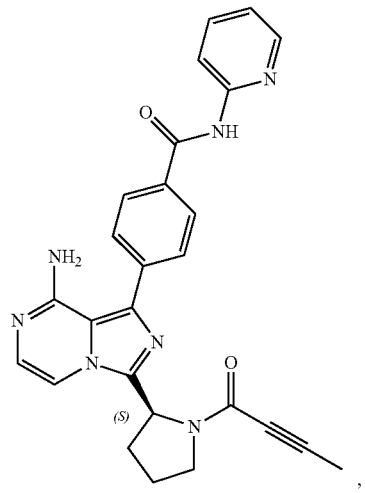

or a salt thereof, wherein the process comprises:
contacting a compound having the structure of Formula (VII):

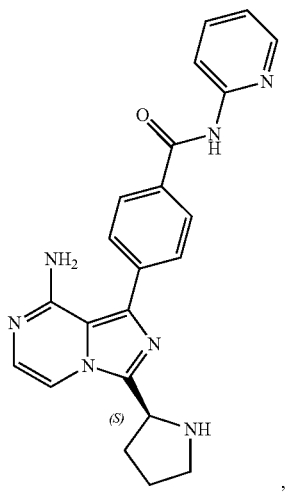

or a salt thereof, with 2-butynoic acid, or a salt thereof, in the presence of 1-propylphosphonic anhydride and a base in a reaction medium to form a reaction mixture comprising the compound of Formula (VIII), or salt thereof, and a reaction by-product comprising a compound having the structure of Formula (XIV):

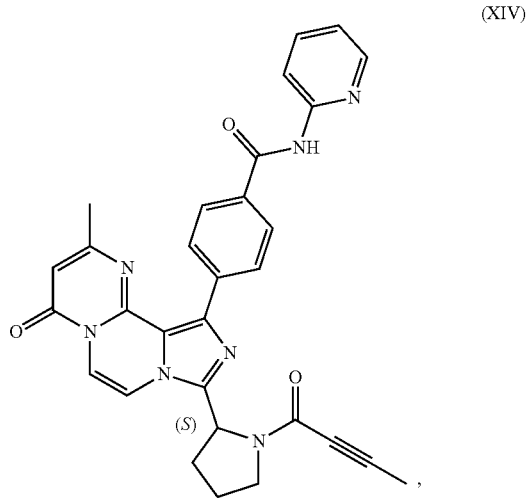

or a salt thereof; and
selectively isolating the compound of Formula (VIII), or salt thereof, from the reaction mixture relative to the compound having the structure of Formula (XIV).

2. The process of claim 1, wherein the contacting step comprises:
adding the compound of Formula (VII), or salt thereof, and the base to the reaction medium;
adding the 2-butynoic acid, or salt thereof, to the reaction medium comprising the compound of Formula (VII), or salt thereof, and the base; and adding the 1-propylphosphonic anhydride to the reaction medium comprising the compound of Formula (VII), or salt thereof; 2-butynoic acid, or salt thereof; and the base.

3. The process of claim 1, wherein the process comprises:
contacting the compound of Formula (VII), or salt thereof, with the 2-butynoic acid, or salt thereof, in the presence of the 1-propylphosphonic anhydride and the base in the reaction medium to form a reaction mixture comprising the compound of Formula (VIII), or salt thereof; unreacted compound of Formula (VII), or salt thereof; and the reaction by-product comprising the compound of Formula (XIV), or a salt thereof; and
selectively isolating the compound of Formula (VIII), or salt thereof, from the reaction mixture relative to the compound of Formula (VII), or salt thereof, and the compound of Formula (XIV), or salt thereof.

4. The process of claim 1, wherein the process comprises:
contacting the compound of Formula (VII), or a salt thereof, with the 2-butynoic acid, or salt thereof, in the presence of the 1-propylphosphonic anhydride and the base in the reaction medium to form a reaction mixture comprising the compound of Formula (VIII), or salt thereof; unreacted compound of Formula (VII), or salt thereof; and the reaction by-product comprising the compound of Formula (XIV), or a salt thereof;
extracting at least a portion of the compound of Formula (VIII), or salt thereof, from the reaction mixture into an aqueous phase, wherein the compound of Formula (VIII), or salt thereof, is selectively extracted into the aqueous phase relative to the compound of Formula (XIV), or salt thereof;
adjusting the pH of the aqueous phase; and
extracting at least a portion of the compound of Formula (VIII), or salt thereof, from the aqueous phase into an organic phase, wherein the compound of Formula (VIII), or salt thereof, is selectively extracted into the organic phase relative to the compound of Formula (VII), or salt thereof.

5. The process of claim 4, wherein the process further comprises isolating the compound of Formula (VIII) from the organic phase into which the compound of Formula (VIII) has been selectively extracted.

6. The process of claim 4, wherein the aqueous phase has a pH less than about 2.5 during the aqueous phase extracting step.

7. The process of claim 4, wherein the aqueous phase has a pH greater than about 4.0 during the organic phase extracting step.

8. The process of claim 6, wherein the aqueous phase comprises greater than about 75 area % of the compound of Formula (VIII) and less than about 2.0 area % of the compound of Formula (XIV) as measured by high-performance liquid chromatography upon completion of the aqueous phase extraction.

9. The process of claim 7, wherein the organic phase comprises at least about 75 area % of the compound of Formula (VIII) and less than about 2.0 area % of the compound of Formula (VII) as measured by high-performance liquid chromatography upon completion of the organic phase extraction.

10. The process of claim 4, wherein:
the aqueous phase has a pH less than about 2.5 during the aqueous phase extracting step; and
the aqueous phase has a pH greater than about 4.0 during the organic phase extracting step.

11. The process of claim 4, wherein:
the aqueous phase has a pH from about 1.8 to about 2.2 during the aqueous phase extracting step; and
the aqueous phase has a pH from about 4.5 to about 5.0 during the organic phase extracting step.

12. The process of claim 4, wherein the base comprises at least one compound selected from the group consisting of triethylamine, tripropylamine, tributylamine, diisopropylethylamine, N-methylmorpholine, N-methylpyrrolidine, sodium carbonate, sodium bicarbonate, potassium carbonate, and potassium bicarbonate.

13. The process of claim 12, wherein the base comprises triethylamine.

14. The process of claim 4, wherein the reaction medium comprises at least one solvent selected from the group consisting of dichloromethane, tetrahydrofuran, 2-methyltetrahydrofuran, tert-amyl alcohol, acetone, methyl iso-butyl ketone, 2-butanol, methyl ethyl ketone, acetonitrile, and ethyl acetate.

15. The process of claim 14, wherein the reaction medium comprises dichloromethane.

16. The process of claim 4, wherein the organic phase comprises at least one compound selected from the group consisting of dichloromethane, methyltetrahydrofuran, and 2-methyltetrahydrofuran, tert-amyl alcohol, methyl iso-butyl ketone, 2-butanol, methyl ethyl ketone, ethyl acetate, isopropylacetate, N-butylacetate, butyronitrile, toluene, xylene, heptane, hexane, isohexane, and chloroform.

17. The process of claim 16, wherein the organic phase comprises dichloromethane.

18. The process of claim 4, wherein the compound of Formula (VII) is contacted with about 0.5 to about 5.0 molar equivalents of 2-butynoic acid relative to the compound of Formula (VII).

19. The process of claim 4, wherein about 0.3 to about 3.0 molar equivalents of 1-propylphosphonic anhydride are charged to the reaction medium relative to the compound of Formula (VII).

20. The process of claim 4, wherein about 1.0 to about 10.0 molar equivalents of the base are charged to the reaction medium relative to the compound of Formula (VII).

21. The process of claim 4, wherein the reaction medium is maintained at a temperature from about 10° C. to about 30° C. during the contacting step.

22. The process of claim 4, wherein the organic phase comprises an organic phase solvent, and the process further comprises exchanging the organic phase solvent with a replacement solvent to form a crystallization mixture comprising the compound of Formula (VIII).

23. The process of claim 22, wherein:
the organic phase solvent is exchanged with the replacement solvent by continuous level distillation; and
the continuous level vacuum distillation is conducted at a temperature that does not exceed about 60° C.

24. The process of claim 22, wherein the replacement solvent comprises an alcohol.

25. The process of claim 22, wherein the replacement solvent comprises ethanol.

26. The process of claim 22, wherein the organic phase solvent comprises dichloromethane and the replacement solvent comprises ethanol.

27. The process of claim 22, wherein the crystallization mixture is maintained at a temperature greater than about 40° C. for at least about five hours after crystallization initiates.

28. The process of claim 27, wherein the crystallization mixture is cooled to a temperature of about 20° C. over a period of at least five hours before isolating the compound of Formula (VIII).

29. The process of claim 1, wherein the compound of Formula (VII) is prepared by a process comprising isolating the compound as a crystalline form characterized by a reflection X-ray powder diffraction pattern comprising at least three peaks selected from the group consisting of 9.9±0.2 °2θ, 11.1±0.2 °2θ, 12.8±0.2 °2θ, 14.1±0.2 °2θ, and 19.0±0.2 °2θ.

* * * * *